United States Patent
Graham et al.

(10) Patent No.: US 10,428,063 B2
(45) Date of Patent: *Oct. 1, 2019

(54) 4H-PYRROLO[3,2-C]PYRIDIN-4-ONE DERIVATIVES

(71) Applicant: Bayer Pharma Aktiengesellschaft, Berlin (DE)

(72) Inventors: Keith Graham, Berlin (DE); Ulrich Klar, Berlin (DE); Hans Briem, Berlin (DE); Volker Schulze, OT Bergf (DE); Gerhard Siemeister, Berlin (DE); Philip Lienau, Berlin (DE); René Tempel, Berlin (DE); Jozsef Bálint, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,032

(22) PCT Filed: Jan. 25, 2016

(86) PCT No.: PCT/EP2016/051432
§ 371 (c)(1),
(2) Date: Jul. 27, 2017

(87) PCT Pub. No.: WO2016/120196
PCT Pub. Date: Aug. 4, 2016

(65) Prior Publication Data
US 2018/0016272 A1    Jan. 18, 2018

(30) Foreign Application Priority Data

Jan. 28, 2015 (EP) .................................. 15152944
Dec. 16, 2015 (EP) .................................. 15200407

(51) Int. Cl.
| | |
|---|---|
| *C07D 471/04* | (2006.01) |
| *C07D 405/14* | (2006.01) |
| *C07D 401/12* | (2006.01) |
| *A61K 31/437* | (2006.01) |
| *A61K 31/444* | (2006.01) |
| *A61K 45/06* | (2006.01) |
| *C07D 519/00* | (2006.01) |

(52) U.S. Cl.
CPC .......... *C07D 471/04* (2013.01); *A61K 31/437* (2013.01); *A61K 31/444* (2013.01); *A61K 45/06* (2013.01); *C07D 401/12* (2013.01); *C07D 405/14* (2013.01); *C07D 519/00* (2013.01)

(58) Field of Classification Search
CPC .................................................. C07D 471/04
See application file for complete search history.

(56) References Cited

U.S. PATENT DOCUMENTS

| | | |
|---|---|---|
| 2011/0021498 A1 | 1/2011 | Stokes et al. |
| 2017/0101391 A1 | 4/2017 | Graham et al. |

FOREIGN PATENT DOCUMENTS

| | | |
|---|---|---|
| WO | WO-2010-145998 A1 | 12/2010 |
| WO | WO-2013/050438 A1 | 4/2013 |
| WO | WO-2013/092512 A1 | 6/2013 |
| WO | WO-2013/167698 A1 | 11/2013 |
| WO | WO-2014-147203 A1 | 9/2014 |
| WO | WO-2014/147204 A1 | 9/2014 |
| WO | WO-2014/202583 A1 | 12/2014 |
| WO | WO-2014/202588 A1 | 12/2014 |
| WO | WO-2014/202590 A1 | 12/2014 |
| WO | WO-2015-193339 A1 | 12/2015 |
| WO | WO-2016/202755 A1 | 12/2016 |
| WO | WO-2017/021348 A1 | 2/2017 |
| WO | WO-2017/102649 A1 | 6/2017 |
| WO | WO-2014/202584 A1 | 12/2017 |

OTHER PUBLICATIONS

Johnson, A. W. Invitation to Organic Chemistry 1999 Jones and Bartlett: Mississauga, Canada, p. 24.*
Silverman, R.B. The Organic Chemistry of Drug Design and Drug Action 1992, Academic: New York, p. 19.*
Wermuth, Camille G. "Molecular Variation Based on Isosteric Replacements" in Chapter 13, The Practice of Medicinal Chemistry, Academic: 1996, pp. 203-237.*
Noel "Synthesis and SAR of 4-(pyrazol-3-yl)-pyridines as novel c-jun N-terminal kinase inhibitors" Bioorganic & Medicinal Chemistry Letters 21 (2011) 2732-2735.*
Fabian et. al. Nature Biotechnology 2005, 23, 329-336.*
Bain "The selectivity of protein kinase inhibitors: a further update" Biochem. J. (2007) 408, 297-315.*

(Continued)

*Primary Examiner* — David K O'Dell
(74) *Attorney, Agent, or Firm* — Morrison & Foerster LLP

(57) ABSTRACT

Compound of formula (I), processes for their production and their use as pharmaceuticals.

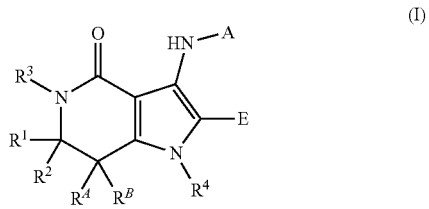

15 Claims, No Drawings

(56) References Cited

OTHER PUBLICATIONS

Ricke et. al. "Bub1 kinase activity drives error correction and mitotic checkpoint control but not tumor suppression" J. Cell Biol. vol. 199 No. 6 931-949.*
Baron et. al. "Probing the catalytic functions of Bub1 kinase using the small molecule inhibitors BAY-320 and BAY-524". eLife 2016; 5:e12187.*
Vardiman "The World Health Organization (WHO) classification of the myeloid neoplasms" Blood (2002), 100(7), 2292-2302.*
Simone, Oncology: Introduction, Cecil Textbook of Medicine, 20th Edition, 1996 vol. 1, pp. 1004-1010.*
Howington "Treatment of Stage I and II Non-small Cell Lung Cancer Diagnosis and Management of Lung Cancer, 3rd ed: American College of Chest Physicians Evidence-Based Clinical Practice Guidelines" Chest 2013; 143(5)(Suppl):e278S-e313S.*
Socinski "Treatment of Stage IV Non-small Cell Lung Cancer Diagnosis and Management of Lung Cancer, 3rd ed: American College of Chest Physicians Evidence-Based Clinical Practice Guideline" Chest 2013; 143(5)(Suppl):e341S-e368S.*
Jett Treatment of Small Cell Lung Cancer Diagnosis and Management of Lung Cancer, 3rd ed: American College of Chest Physicians Evidence-Based Clinical Practice Guidelines Chest 2013; 143(5)(Suppl):e400S-e419S.*
Sanz-Garcia, "Current and advancing treatments for metastatic colorectal cancer" Expert Opinion on Biological Therapy, 16:1, 2016 , 93-110.*
Garson "Models of ovarian cancer—Are we there yet?" Molecular and Cellular Endocrinology 239 (2005) 15-26.*
Sale "Models of ovarian cancer metastasis: Murine models" Drug Discovery Today: Disease Models 2006, 3, 150-154.*
Schober "New Advances in the Treatment of Metastatic Pancreatic Cancer" Digestion 2015;92:175-184.*
Boniface "Multidisciplinary management for esophageal and gastric cancer" Cancer Management and Research 2016:8 39-44.*
Gerratana "Do platinum salts fit all triple negative breast cancers?" Cancer Treatment Reviews 48 (2016) 34-41.*
Yoo "New drugs in prostate cancer" Prostate Int 4 (2016) 37-42.*
Muller and Kräusslich in "Antiviral Strategies" Handbook of Experimental Pharmacology vol. 189 Chapter 1, pp. 1-24.*
Pui "Treatment of Acute Lymphoblastic Leukemia" New England Journal of Medicine 2006, 354, 166-78.*
Krishnan "Multiple myeloma and persistence of drug resistance in the age of novel drugs (Review)" International Journal of Oncology 49: 33-50, 2016.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*
Argollo "Novel therapeutic targets for inflammatory bowel disease" Journal of Autoimmunity (2017), 85, 103-116.*
A.M. Bendele "Animal models of rheumatoid arthritis" J Musculoskel Neuron Interact 2001; 1(4):377-385.*
Bendele, "Animal Models of Arthritis: Relevance to Human Disease" Toxicol Pathol 1999 27: 134-142.*
J. Kang et. al.: "Structure and Substrate Recruitment of the Human Spindle Checkpoint Kinase Bub1 ", Molecular Cell, vol. 32, No. 3, Nov. 7, 2008 (Nov. 7, 2008), pp. 394-405, XP055041762, DOI: 10.1016/j.molcel.2008.09.017.
U.S. Appl. No. 15/317,924, filed Dec. 9, 2016, Keith Graham et al.

* cited by examiner

4H-PYRROLO[3,2-C]PYRIDIN-4-ONE DERIVATIVES

CROSS REFERENCE TO RELATED APPLICATIONS

This application is the national stage of International Application No. PCT/EP2016/051432, filed internationally on Jan. 25, 2016, which claims the benefit of European Application No. 15200407.3, filed Dec. 16, 2015, and European Application No.15152944.3, filed Jan. 28, 2015, the disclosures of which are hereby incorporated by reference in their entireties for all purposes.

FIELD OF APPLICATION OF THE INVENTION

The invention relates to substituted 4H-pyrrolo[3,2-c]pyridin-4-one compounds, a process for their production and uses thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The eukaryotic cell division cycle (or cell cycle) ensures the duplication of the genome and its distribution to the daughter cells by passing through a coordinated and regulated sequence of events. The cell cycle is divided into four successive phases:
1. The G1 phase represents the time before the DNA replication, in which the cell grows and is sensitive to external stimuli.
2. In the S phase the cell replicates its DNA, and
3. in the G2 phase preparations are made for entry into mitosis.
4. In mitosis (M phase), the duplicated chromosomes get separated supported by a spindle device built from microtubules, and cell division into two daughter cells is completed.

To ensure the extraordinary high fidelity required for an accurate distribution of the chromosomes to the daughter cells, the passage through the cell cycle is strictly regulated and controlled. The enzymes that are necessary for the progression through the cycle must be activated at the correct time and are also turned off again as soon as the corresponding phase is passed. Corresponding control points ("checkpoints") stop or delay the progression through the cell cycle if DNA damage is detected, or the DNA replication or the creation of the spindle device is not yet completed. The mitotic checkpoint (also known as spindle checkpoint or spindle assembly checkpoint) controls the accurate attachment of mircrotubules of the spindle device to the kinetochors (the attachment site for microtubules) of the duplicated chromosomes. The mitotic checkpoint is active as long as unattached kinetochores are present and generates a wait-signal to give the dividing cell the time to ensure that each kinetochore is attached to a spindle pole, and to correct attachment errors. Thus the mitotic checkpoint prevents a mitotic cell from completing cell division with unattached or erroneously attached chromosomes [Suijkerbuijk S J and Kops G J, Biochem. Biophys. Acta 1786, 24, 2008; Musacchio A and Salmon E D, Nat. Rev. Mol. Cell. Biol. 8, 379, 2007]. Once all kinetochores are attached with the mitotic spindle poles in a correct bipolar (amphitelic) fashion, the checkpoint is satisfied and the cell enters anaphase and proceeds through mitosis.

The mitotic checkpoint is established by a complex network of a number of essential proteins, including members of the MAD (mitotic arrest deficient, MAD 1-3) and Bub (Budding uninhibited by benzimidazole, Bub 1-3) families, Mps1 kinase, cdc20, as well as other components [reviewed in Bolanos-Garcia V M and Blundell T L, Trends Biochem. Sci. 36, 141, 2010], many of these being over-expressed in proliferating cells (e.g. cancer cells) and tissues [Yuan B et al., Clin. Cancer Res. 12, 405, 2006]. The major function of an unsatisfied mitotic checkpoint is to keep the anaphase-promoting complex/cyclosome (APC/C) in an inactive state. As soon as the checkpoint gets satisfied the APC/C ubiquitin-ligase targets cyclin B and securin for proteolytic degradation leading to separation of the paired chromosomes and exit from mitosis.

Inactive mutations of the Ser/Thr kinase Bub1 prevented the delay in progression through mitosis upon treatment of cells of the yeast *S. cerevisiae* with microtubule-destabilizing drugs, which led to the identification of Bub1 as a mitotic checkpoint protein [Roberts B T et al., Mol. Cell Biol., 14, 8282, 1994]. A number of recent publications provide evidence that Bub1 plays multiple roles during mitosis which, have been reviewed by Elowe [Elowe S, Mol. Cell. Biol. 31, 3085, 2011. In particular, Bub1 is one of the first mitotic checkpoint proteins that binds to the kinetochores of duplicated chromosomes and probably acts as a scaffolding protein to constitute the mitotic checkpoint complex. Furthermore, via phosphorylation of histone H2A, Bub1 localizes the protein shugoshin to the centromeric region of the chromosomes to prevent premature segregation of the paired chromosomes [Kawashima et al. Science 327, 172, 2010]. In addition, together with a Thr-3 phosphorylated Histone H3 the shugoshin protein functions as a binding site for the chromosomal passenger complex which includes the proteins survivin, borealin, INCENP and Aurora B. The chromosomal passenger complex is seen as a tension sensor within the mitotic checkpoint mechanism, which dissolves erroneously formed microtubule-kinetochor attachments such as syntelic (both sister kinetochors are attached to one spindle pole) or merotelic (one kinetochor is attached to two spindle poles) attachments [Watanabe Y, Cold Spring Harb. Symp. Quant. Biol. 75, 419, 2010]. Recent data suggest that the phosphorylation of histone H2A at Thr 121 by Bub1 kinase is sufficient to localize AuroraB kinase to fulfill the attachment error correction checkpoint [Ricke et al. J. Cell Biol. 199, 931-949, 2012].

Incomplete mitotic checkpoint function has been linked with aneuploidy and tumourigenesis [Weaver B A and Cleveland D W, Cancer Res. 67, 10103, 2007; King R W, Biochim Biophys Acta 1786, 4, 2008]. In contrast, complete inhibition of the mitotic checkpoint has been recognised to result in severe chromosome missegregation and induction of apoptosis in tumour cells [Kops G J et al., Nature Rev. Cancer 5, 773, 2005; Schmidt M and Medema R H, Cell Cycle 5, 159, 2006; Schmidt M and Bastians H, Drug Res. Updates 10, 162, 2007]. Thus, mitotic checkpoint abrogation through pharmacological inhibition of components of the mitotic checkpoint, such as Bub1 kinase, represents a new approach for the treatment of proliferative disorders, including solid tumours such as carcinomas, sarcomas, leukaemias and lymphoid malignancies or other disorders, associated with uncontrolled cellular proliferation.

The present invention relates to chemical compounds that inhibit Bub1 kinase.

Established anti-mitotic drugs such as *vinca* alkaloids, taxanes or epothilones activate the mitotic checkpoint, inducing a mitotic arrest either by stabilising or destabilising microtubule dynamics. This arrest prevents separation of the duplicated chromosomes to form the two daughter cells. Prolonged arrest in mitosis forces a cell either into mitotic exit without cytokinesis (mitotic slippage or adaption) or into mitotic catastrophe leading to cell death [Rieder C L and Maiato H, Dev. Cell 7, 637, 2004].

In contrast, inhibitors of Bub1 prevent the establishment and/or functionality of the mitotic checkpoint and/or microtubule-kinetochor attachment error correction mechanisms, which finally results in severe chromosomal missegregation, induction of apoptosis and cell death.

These findings suggest that Bub1 inhibitors should be of therapeutic value for the treatment of proliferative disorders associated with enhanced uncontrolled proliferative cellular processes such as, for example, cancer, inflammation, arthritis, viral diseases, cardiovascular diseases, or fungal diseases in a warm-blooded animal such as man.

WO 2013/050438, WO 2013/092512, WO 2013/167698, WO 2014/147203, WO 2014/147204, WO2014202590, WO2014202588, WO2014202584, WO2014202583 disclose substituted indazoles substituted pyrazoles, substituted cycloalkylpyrazoles, which are Bub1 kinase inhibitors.

WO 2010/145998 discloses pyrimidinylpyrrolopyridinone derivatives, which may be useful as kinase inhibitors.

Due to the fact that especially cancer disease as being expressed by uncontrolled proliferative cellular processes in tissues of different organs of the human- or animal body still is not considered to be a controlled disease in that sufficient drug therapies already exist, there is a strong need to provide further new therapeutically useful drugs, preferably inhibiting new targets and providing new therapeutic options (e.g. drugs with improved pharmacological properties).

DESCRIPTION OF THE INVENTION

Therefore, inhibitors of Bub1 represent valuable compounds that should complement therapeutic options either as single agents or in combination with other drugs.

In accordance with a first aspect, the invention relates to compounds of formula (I), (I)

in which:
$R^1$ represents hydrogen, $C_1$-$C_6$-alkyl or $C_1$-$C_6$-haloalkyl;
$R^2$ represents hydrogen, $C_1$-$C_6$-alkyl or $C_1$-$C_6$-haloalkyl; or
$R^1$ and $R^2$ together with the carbon atom to which they are attached form a 3- to 6-membered cycloalkyl ring;
$R^3$ represents hydrogen, $C_1$-$C_4$-alkyl, $R^{11}$—C(O)—, $R^{11}$O—C(O)— or phenyl-$C_1$-$C_3$-alkyl-, wherein said phenyl group is optionally substituted, one or more times, independently of each other, with $R^5$;
$R^4$ represents hydrogen, $C_1$-$C_4$-alkyl or $C_1$-$C_4$-alkoxy-$C_2$-$C_4$-alkyl-;
$R^A$ represents hydrogen, hydroxy or $C_1$-$C_4$-alkyl;
$R^B$ represents hydrogen; or
$R^B$ and $R^2$ together form an additional bond;
A represents a group selected from:

wherein * indicates the point of attachment of said group with the rest of the molecule and said group is optionally substituted, one or more times, independently of each other, with $R^5$;
$R^5$ represents hydroxy, halogen, cyano, $C_1$-$C_4$-alkyl, $C_1$-$C_4$-alkoxy, $C_1$-$C_4$-haloalkyl or $C_1$-$C_4$-haloalkoxy;
E represents a group selected from:

wherein * indicates the point of attachment of said group with the rest of the molecule;
$R^5$ represents, independently of each other, halogen, hydroxy, nitro, cyano, $C_1$-$C_4$-alkyl, $C_1$-$C_4$-haloalkyl, $C_1$-$C_6$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—,
wherein said $C_1$-$C_6$-alkoxy is optionally substituted one, two or three times, independently of each other, with halogen and is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally substituted one or more times, independently of each other, with $R^5$;
$R^9$, $R^{10}$ represent, independently of each other, hydrogen, $C_1$-$C_4$-alkyl, $C_3$-$C_6$-cycloalkyl, $C_1$-$C_4$-halocycloalkyl or phenyl, wherein said phenyl group is optionally substituted, one or more times, independently of each other, with $R^5$, or
$R^9$ and $R^{19}$ together with the nitrogen atom to which they are attached form a 3- to 6-membered nitrogen containing heterocyclic ring, optionally containing one additional heteroatom or heteroatom containing group selected from O, NH and S, and which may be optionally substituted, one or more times, independently of each other, with $R^5$;

$R^{11}$ represents, independently of each other, $C_1$-$C_4$-alkyl, $C_3$-$C_6$-cycloalkyl, $C_1$-$C_4$-haloalkyl or $C_3$-$C_6$-halocycloalkyl;

m represents 0, 1, 2 or 3;

n represents 0, 1, or 2;

or an N-oxide, a salt, a tautomer or a stereoisomer of said compound, or a salt of said N-oxide, tautomer or stereoisomer.

In a second aspect, the invention relates to compounds of formula (I) as described supra, wherein $R^1$ represents hydrogen, $C_1$-$C_4$-alkyl or $C_1$-$C_4$-haloalkyl;

$R^2$ represents hydrogen, $C_1$-$C_4$-alkyl or $C_1$-$C_4$-haloalkyl; or $R^1$ and $R^2$ together with the carbon atom to which they are attached form a 3- to 6-membered cycloalkyl ring;

$R^3$ represents hydrogen, $C_1$-$C_4$-alkyl, $C_1$-$C_4$haloalky, $R^{11}$—C(O)— or $R^{11}$O—C(O)—;

$R^4$ represents hydrogen, $C_1$-$C_4$-alkyl or $C_1$-$C_4$-alkoxy-$C_2$-$C_4$-alkyl-;

$R^A$ represents hydrogen, hydroxy or $C_1$-$C_4$-alkyl;

$R^B$ represents hydrogen; or $R^B$ and $R^2$ together form an additional bond;

A represents a group

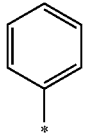

wherein * indicates the point of attachment of said group with the rest of the molecule and said group is optionally substituted, one or more times, independently of each other, with $R^5$;

$R^5$ represents hydroxy, halogen, cyano, $C_1$-$C_4$-alkyl, $C_1$-$C_4$-alkoxy, $C_1$-$C_4$-haloalkyl or $C_1$-$C_4$-haloalkoxy;

E represents a group selected from:

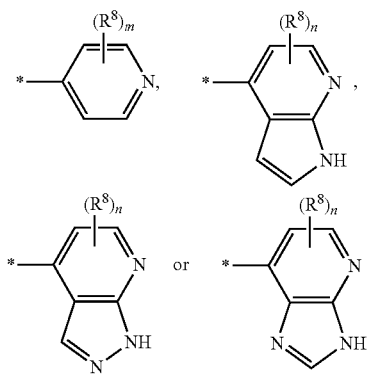

wherein * indicates the point of attachment of said group with the rest of the molecule;

$R^8$ represents, independently of each other, halogen, hydroxy, nitro, cyano, $C_1$-$C_4$-alkyl, $C_1$-$C_4$-haloalkyl, $C_1$-$C_6$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—, wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally substituted, one or more times, independently of each other, with $R^5$;

$R^9$, $R^{10}$ represent, independently of each other, hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally substituted, one or more times, independently of each other, with $R^5$, or $R^9$ and $R^{10}$ together with the nitrogen atom to which they are attached form a 3- to 6-membered nitrogen containing heterocyclic ring, optionally containing one additional heteroatom or heteroatom containing group selected from O, NH or S, and which may be optionally substituted, one or more times, independently of each other, with $R^5$;

$R^{11}$ represents, independently of each other, $C_1$-$C_4$-alkyl, $C_3$-$C_6$-cycloalkyl, $C_1$-$C_4$-haloalkyl or $C_3$-$C_6$-halocycloalkyl;

m represents 0, 1, 2 or 3;

n represents 0, or 1;

or an N-oxide, a salt, a tautomer or a stereoisomer of said compound, or a salt of said N-oxide, tautomer or stereoisomer.

In a third aspect, the invention relates to compounds of formula (I) as described supra, wherein:

$R^1$ represents hydrogen, $C_1$-$C_4$-alkyl or $C_1$-$C_4$-haloalkyl;

$R^2$ represents hydrogen, $C_1$-$C_4$-alkyl or $C_1$-$C_4$-haloalkyl; or $R^1$ and $R^2$ together with the carbon atom to which they are attached form a 3- to 6-membered cycloalkyl ring;

$R^3$ represents hydrogen, $C_1$-$C_4$-alkyl, $C_1$-$C_4$-haloalkyl, $R^{11}$—C(O)— or $R^{11}$O—C(O)—;

$R^4$ represents hydrogen, $C_1$-$C_4$-alkyl or $C_1$-$C_4$-alkoxy-$C_2$-$C_4$-alkyl;

$R^A$ represents hydrogen, hydroxy or $C_1$-$C_4$-alkyl;

$R^B$ represents hydrogen; or $R^B$ and $R^2$ together form an additional bond;

A represents a group

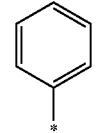

wherein * indicates the point of attachment of said group with the rest of the molecule and said group is optionally substituted, one or more times, independently of each other, with $R^5$;

$R^5$ represents hydroxy, halogen, cyano, $C_1$-$C_4$-alkyl, $C_1$-$C_4$-alkoxy, $C_1$-$C_4$-haloalkyl or $C_1$-$C_4$-haloalkoxy;

E represents a group selected from:

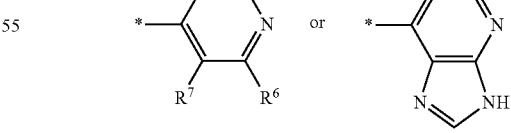

wherein * indicates the point of attachment of said group with the rest of the molecule;

$R^6$, $R^7$ represents, independently of each other, hydrogen, halogen, hydroxy, cyano, $C_1$-$C_4$-alkyl, $C_1$-$C_6$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—, wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N—$, $C_3$-$C_6$-cycloalkyl, 5- to 6-membered heterocycloalkyl or phenyl, which is optionally substituted, one or more times, independently of each other, with $R^5$;
$R^9$, $R^{10}$ represent, independently of each other, hydrogen or $C_1$-$C_4$-alkyl;
$R^{11}$ represents, independently of each other, $C_1$-$C_4$-alkyl, $C_3$-$C_6$-cycloalkyl or $C_3$-$C_6$-halocycloalkyl;
or an N-oxide, a salt, a tautomer or a stereoisomer of said compound, or a salt of said N-oxide, tautomer or stereoisomer.

In a fourth aspect, the invention relates to compounds of formula (I) as described supra, wherein:
$R^1$ represents hydrogen or $C_1$-$C_4$-alkyl;
$R^2$ represents hydrogen or $C_1$-$C_4$-alkyl; or
$R^1$ and $R^2$ together with the carbon atom to which they are attached form a 3- to 6-membered cycloalkyl ring;
$R^3$ represents hydrogen, $C_1$-$C_4$-alkyl, $R^{11}$—C(O)— or $R^{11}$O—C(O)—;
$R^4$ represents hydrogen, $C_1$-$C_4$-alkyl or $C_1$-$C_4$-alkoxy-$C_2$-$C_4$-alkyl;
$R^A$ represents hydrogen;
$R^B$ represents hydrogen; or
$R^B$ and $R^2$ together form an additional bond;
A represents a group

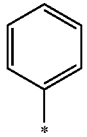 [SMILES: *c1ccccc1]

wherein * indicates the point of attachment of said group with the rest of the molecule and said group is optionally substituted, one or more times, independently of each other, with $R^5$;
$R^5$ represents halogen;
E represents a group selected from:

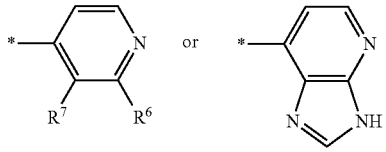

wherein * indicates the point of attachment of said group with the rest of the molecule;
$R^6$, $R^7$ represents, independently of each other, hydrogen, halogen, $C_1$-$C_4$-alkyl, $C_1$-$C_6$-alkoxy, $R^9R^{10}N—$, $R^{11}$—C(O)—NH— or $R^9R^{10}N$—C(O)—NH—,
wherein said $C_1$-$C_6$-alkoxy is optionally substituted one, two or three times, independently of each other, with halogen or is optionally substituted one time with hydroxy, methoxy, $(CH_3)_2N—$, cyclopropyl, 5-membered heterocycloalkyl or phenyl, which is optionally substituted once with $R^5$;
$R^9$, $R^{10}$ represent, independently of each other, hydrogen or $C_1$-$C_4$-alkyl;
$R^{11}$ represents, independently of each other, $C_1$-$C_4$-alkyl, $C_3$-$C_6$-cycloalkyl or $C_3$-$C_6$-halocycloalkyl;
or an N-oxide, a salt, a tautomer or a stereoisomer of said compound, or a salt of said N-oxide, tautomer or stereoisomer.

In accordance with a fifth aspect, the invention relates to compounds of formula (I) as described supra, wherein:
$R^1$ represents hydrogen or methyl;
$R^2$ represents hydrogen or methyl;
$R^3$ represents hydrogen, methyl, iso-propyl-C(O)— or tert-butyl-O—C(O)—;
$R^4$ represents hydrogen, ethyl or 2-methoxy-ethyl;
$R^A$ represents hydrogen;
$R^B$ represents hydrogen; or
$R^B$ and $R^2$ together form an additional bond;
A represents phenyl, which is optionally substituted with one or two fluorine atoms;
E represents a group selected from:

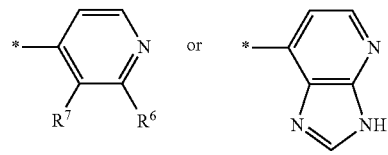

wherein * indicates the point of attachment of said group with the rest of the molecule;
$R^6$ represents hydrogen, methyl, $H_2N—$, $R^{11}$—C(O)—NH— or $R^9R^{10}N$—C(O)—NH—;
$R^7$ represents hydrogen, fluoro, methyl, methoxy, cyclopropylmethoxy, tetrahydrofuran-3-ylmethoxy, 2-hydroxyethoxy, 2-methoxyethoxy, 2,2-difluoroethoxy, 2,2,2-trifluoroethoxy, 2-(dimethylamino)ethoxy, propoxy 3,3,3-trifluoropropoxy, butoxy, 3,3-dimethylbutoxy or benzyloxy,
$R^9$, $R^{10}$ represent, independently of each other, hydrogen or ethyl;
$R^{11}$ represents, independently of each other, methyl, iso-propyl, tert-butyl, cyclopropyl or fluorocyclopropyl;
or an N-oxide, a salt, a tautomer or a stereoisomer of said compound, or a salt of said N-oxide, tautomer or stereoisomer.

In accordance with a sixth aspect, the invention relates to compounds of formula (I) as described supra, which have formula (Ia),

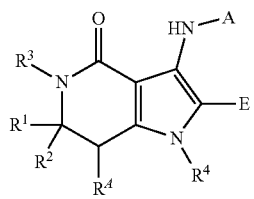

(Ia)

wherein
$R^1$ represents hydrogen or methyl;
$R^2$ represents hydrogen or methyl;
$R^3$ represents hydrogen, methyl, iso-propyl-C(O)— or tert-butyl-O—C(O)—;
$R^4$ represents hydrogen, ethyl or 2-methoxy-ethyl;
$R^A$ represents hydrogen;
A represents phenyl, which is optionally substituted with one or two fluorine atoms;

E represents a group selected from:

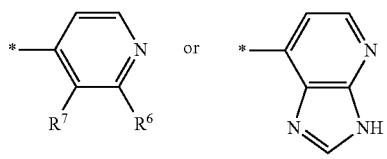 or 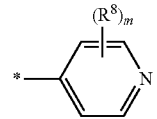

wherein * indicates the point of attachment of said group with the rest of the molecule;

$R^6$ represents hydrogen, methyl, $H_2N-$, $R^{11}-C(O)-NH-$ or $R^9R^{10}N-C(O)-NH-$;

$R^7$ represents hydrogen, fluoro, methyl, methoxy, cyclopropylmethoxy, tetrahydrofuran-3-ylmethoxy, 2-hydroxyethoxy, 2-methoxyethoxy, 2,2-difluoroethoxy, 2,2,2-trifluoroethoxy, 2-(dimethylamino)ethoxy, propoxy 3,3,3-trifluoropropoxy, butoxy, 3,3-dimethylbutoxy or benzyloxy, $R^9$, $R^{10}$ represent, independently of each other, hydrogen or ethyl;

$R^{11}$ represents, independently of each other, methyl, isopropyl, tert-butyl, cyclopropyl or fluorocyclopropyl;

or an N-oxide, a salt, a tautomer or a stereoisomer of said compound, or a salt of said N-oxide, tautomer or stereoisomer.

In a seventh aspect, the invention relates to compounds of formula (I) as defined supra, which have formula (Ic),

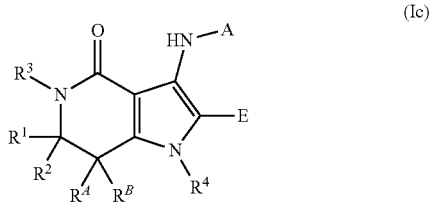

(Ic)

in which:

$R^1$ represents hydrogen, $C_1$-$C_6$-alkyl or $C_1$-$C_6$-haloalkyl;

$R^2$ represents hydrogen, $C_1$-$C_6$-alkyl or $C_1$-$C_6$-haloalkyl; or $R^1$ and $R^2$ together with the carbon atom to which they are attached form a 3- to 6-membered cycloalkyl ring;

$R^3$ represents hydrogen, $C_1$-$C_4$-alkyl, $C_1$-$C_4$-haloalkyl, $R^{11}-C(O)-$, $R^{11}O-C(O)-$ or phenyl-$C_1$-$C_3$-alkyl, wherein said phenyl group is optionally substituted, one or more times, independently of each other, with $R^5$;

$R^4$ represents hydrogen, $C_1$-$C_4$-alkyl or $C_1$-$C_4$-alkoxy-$C_2$-$C_4$-alkyl;

$R^A$ represents hydrogen, hydroxy or $C_1$-$C_4$-alkyl;

$R^B$ represents hydrogen; or $R^B$ and $R^2$ together form an additional bond;

A represents a group

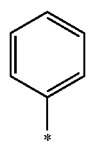 [SMILES: *c1ccccc1]

wherein * indicates the point of attachment of said group with the rest of the molecule and said group is optionally substituted, one or more times, independently of each other, with $R^5$;

$R^5$ represents hydroxy, halogen, cyano, $C_1$-$C_4$-alkyl, $C_1$-$C_4$-alkoxy, $C_1$-$C_4$-haloalkyl or $C_1$-$C_4$-haloalkoxy;

E represents a group:

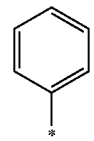

wherein * indicates the point of attachment of said group with the rest of the molecule;

$R^8$ represents, independently of each other, halogen, hydroxy, nitro, cyano, $C_1$-$C_4$-alkyl, $C_1$-$C_4$-haloalkyl, $C_1$-$C_4$-alkoxy, $C_3$-$C_6$-cycloalkyl, $C_3$-$C_6$-halocycloalkyl, $R^9R^{10}N-$, $R^{11}-C(O)-NH-$, $R^{11}O-C(O)-NH-$ or $R^9R^{10}N-C(O)-NH-$;

$R^9$, $R^{10}$ represent, independently of each other, hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally substituted, one or more times, independently of each other, with $R^5$, or $R^9$ and $R^{10}$ together with the nitrogen atom to which they are attached form a 3- to 6-membered nitrogen containing heterocyclic ring, optionally containing one additional heteroatom or heteroatom containing group selected from O, NH and S, and which may be optionally substituted, one or more times, independently of each other, with $R^5$;

$R^{11}$ represents, independently of each other, $C_1$-$C_4$-alkyl, $C_3$-$C_6$-cycloalkyl, $C_1$-$C_4$-haloalkyl or $C_3$-$C_6$-halocycloalkyl;

m represents 0, 1, 2 or 3;

or an N-oxide, a salt, a tautomer or a stereoisomer of said compound, or a salt of said N-oxide, tautomer or stereoisomer.

In another aspect, the invention relates to compounds of formula (I) as defined supra, which have formula (Ic) supra, wherein $R^1$ represents hydrogen, $C_1$-$C_4$-alkyl or $C_1$-$C_4$-haloalkyl;

$R^2$ represents hydrogen, $C_1$-$C_4$-alkyl or $C_1$-$C_4$-haloalkyl; or $R^1$ and $R^2$ together with the carbon atom to which they are attached form a 3- to 6-membered cycloalkyl ring;

$R^3$ represents hydrogen, $C_1$-$C_4$-alkyl, $R^{11}-C(O)-$ or $R^{11}O-C(O)-$;

$R^4$ represents hydrogen, $C_1$-$C_4$-alkyl or $C_1$-$C_4$-alkoxy-$C_2$-$C_4$-alkyl;

$R^A$ represents hydrogen, hydroxy or $C_1$-$C_4$-alkyl;

$R^B$ represents hydrogen; or $R^B$ and $R^2$ together form an additional bond;

A represents a group selected from:

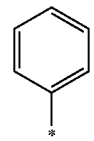

wherein * indicates the point of attachment of said group with the rest of the molecule and said group is optionally substituted, one or more times, independently of each other, with $R^5$;

$R^5$ represents hydroxy, halogen, cyano, $C_1$-$C_4$-alkyl, $C_1$-$C_4$-alkoxy, $C_1$-$C_4$-haloalkyl or $C_1$-$C_4$-haloalkoxy;

E represents a group:

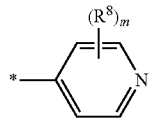

wherein * indicates the point of attachment of said group with the rest of the molecule;

$R^8$ represents, independently of each other, halogen, hydroxy, nitro, cyano, $C_1$-$C_4$-alkyl, $C_1$-$C_4$-haloalkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—;

$R^9$, $R^{10}$ represent, independently of each other, hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally substituted, one or more times, independently of each other, with $R^5$, or $R^9$ and $R^{10}$ together with the nitrogen atom to which they are attached form a 3- to 6-membered nitrogen containing heterocyclic ring, optionally containing one additional heteroatom or heteroatom containing group selected from O, NH or S, and which may be optionally substituted, one or more times, independently of each other, with $R^5$;

$R^{11}$ represents, independently of each other, $C_1$-$C_4$-alkyl, $C_3$-$C_6$-cycloalkyl, $C_1$-$C_4$-haloalkyl or $C_3$-$C_6$-halocycloalkyl;

m represents 0, 1, 2 or 3;

or an N-oxide, a salt, a tautomer or a stereoisomer of said compound, or a salt of said N-oxide, tautomer or stereoisomer.

In another aspect, the invention relates to compounds of formula (I) as defined supra, which have formula (Ic) supra, wherein:

$R^1$ represents hydrogen, $C_1$-$C_4$-alkyl or $C_1$-$C_4$-haloalkyl;

$R^2$ represents hydrogen, $C_1$-$C_4$-alkyl or $C_1$-$C_4$-haloalkyl; or $R^1$ and $R^2$ together with the carbon atom to which they are attached form a 3- to 6-membered cycloalkyl ring;

$R^3$ represents hydrogen, $C_1$-$C_4$-alkyl, $C_1$-$C_4$-haloalky, $R^{11}$—C(O)— or $R^{11}$O—C(O)—;

$R^4$ represents hydrogen, $C_1$-$C_4$-alkyl or $C_1$-$C_4$-alkoxy-$C_2$-$C_4$-alkyl;

$R^A$ represents hydrogen, hydroxy or $C_1$-$C_4$-alkyl;

$R^B$ represents hydrogen; or $R^B$ and $R^2$ together form an additional bond;

A represents a group selected from:

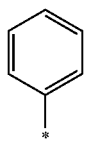 [SMILES: *c1ccccc1]

wherein * indicates the point of attachment of said group with the rest of the molecule and said group is optionally substituted, one or more times, independently of each other, with $R^5$;

$R^5$ represents hydroxy, halogen, cyano, $C_1$-$C_4$-alkyl, $C_1$-$C_4$-alkoxy, $C_1$-$C_4$-haloalkyl or $C_1$-$C_4$-haloalkoxy;

E represents a group:

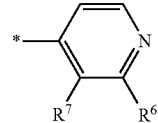

wherein * indicates the point of attachment of said group with the rest of the molecule;

$R^6$, $R^7$ represent, independently of each other, hydrogen, halogen, hydroxy, cyano, $C_1$-$C_4$-alkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)— NH— or $R^9R^{10}N$—C(O)—NH—;

$R^9$, $R^{10}$ represent, independently of each other, hydrogen or $C_1$-$C_4$-alkyl;

$R^{11}$ represents, independently of each other, $C_1$-$C_4$-alkyl;

or an N-oxide, a salt, a tautomer or a stereoisomer of said compound, or a salt of said N-oxide, tautomer or stereoisomer.

In another aspect, the invention relates to compounds of formula (I) as defined supra, which have formula (Ic) supra, wherein, $R^1$ represents hydrogen or $C_1$-$C_4$-alkyl;

$R^2$ represents hydrogen or $C_1$-$C_4$-alkyl; or $R^1$ and $R^2$ together with the carbon atom to which they are attached form a 3- to 6-membered cycloalkyl ring;

$R^3$ represents hydrogen, $C_1$-$C_4$-alkyl, $R^{11}$—C(O)— or $R^{11}$O—C(O)—;

$R^4$ represents hydrogen, $C_1$-$C_4$-alkyl or $C_1$-$C_4$-alkoxy-$C_2$-$C_4$-alkyl;

$R^A$ represents hydrogen;

$R^B$ represents hydrogen; or $R^B$ and $R^2$ together form an additional bond;

A represents a group selected from:

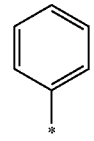 [SMILES: *c1ccccc1]

wherein * indicates the point of attachment of said group with the rest of the molecule and said group is optionally substituted, one or more times, independently of each other, with $R^5$;

$R^5$ represents halogen;

E represents a group:

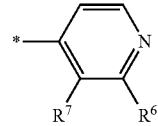

wherein * indicates the point of attachment of said group with the rest of the molecule;

$R^6$, $R^7$ represent, independently of each other, hydrogen, halogen, $C_1$-$C_4$-alkyl, $R^9R^{10}N$—, $R^{11}$—C(O)—NH— or $R^9R^{10}N$—C(O)—NH—;

$R^9$, $R^{10}$ represent, independently of each other, hydrogen or $C_1$-$C_4$-alkyl;

$R^{11}$ represents, independently of each other, $C_1$-$C_4$-alkyl;

or an N-oxide, a salt, a tautomer or a stereoisomer of said compound, or a salt of said N-oxide, tautomer or stereoisomer.

In another aspect, the invention relates to compounds of formula (I) as defined supra, which have formula (Ic) supra, wherein $R^1$ represents hydrogen or methyl;
$R^2$ represents hydrogen or methyl;
$R^3$ represents hydrogen, methyl, iso-propyl-C(O)— or tert-butyl-O—C(O)—;
$R^4$ represents hydrogen, ethyl or 2-methoxy-ethyl;
$R^A$ represents hydrogen;
$R^B$ represents hydrogen; or
$R^B$ and $R^2$ together form an additional bond;
A represents phenyl, which is optionally substituted with one fluorine atom;
E represents a group:

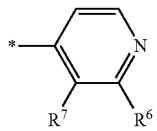

wherein * indicates the point of attachment of said group with the rest of the molecule; and
$R^6$ represents hydrogen, methyl, $H_2N$—, $R^{11}$—C(O)—NH— or $R^9R^{10}N$—C(O)—NH—;
$R^7$ represents hydrogen, fluorine or methyl;
$R^9$, $R^{10}$ represent, independently of each other, hydrogen or ethyl;
$R^{11}$ represents methyl or iso-propyl;
or an N-oxide, a salt, a tautomer or a stereoisomer of said compound, or a salt of said N-oxide, tautomer or stereoisomer.

In a further aspect of the invention the compounds of formula (I) as described above are selected from the group consisting of:
6,6-dimethyl-3-(phenylamino)-2-(pyridin-4-yl)-1,5,6,7-tetrahydro-4H-pyrrolo[3,2-c]pyridin-4-one,
3-(phenylamino)-2-(pyridin-4-yl)-1,5,6,7-tetrahydro-4H-pyrrolo[3,2-c]pyridin-4-one,
2-(3-methylpyridin-4-yl)-3-(phenylamino)-1,5,6,7-tetrahydro-4H-pyrrolo[3,2-c]pyridin-4-one,
1-ethyl-6,6-dimethyl-3-(phenylamino)-2-(pyridin-4-yl)-1,5,6,7-tetrahydro-4H-pyrrolo[3,2-c]pyridin-4-one,
1-ethyl-3-(phenylamino)-2-(pyridin-4-yl)-1,5,6,7-tetrahydro-4H-pyrrolo[3,2-c]pyridin-4-one,
tert-butyl 4-oxo-3-(phenylamino)-2-(pyridin-4-yl)-1,4,6,7-tetrahydro-5H-pyrrolo[3,2-c]pyridine-5-carboxylate,
3-[(4-fluorophenyl)amino]-2-(pyridin-4-yl)-1,5,6,7-tetrahydro-4H-pyrrolo[3,2-c]pyridin-4-one,
2-(2-aminopyridin-4-yl)-3-(phenylamino)-1,5,6,7-tetrahydro-4H-pyrrolo[3,2-c]pyridin-4-one,
1-(2-methoxyethyl)-3-(phenylamino)-2-(pyridin-4-yl)-1,5,6,7-tetrahydro-4H-pyrrolo[3,2-c]pyridin-4-one,
1-ethyl-3-[(4-fluorophenyl)amino]-2-(pyridin-4-yl)-1,5,6,7-tetrahydro-4H-pyrrolo[3,2-c]pyridin-4-one,
2-(2-methylpyridin-4-yl)-3-(phenylamino)-1,5,6,7-tetrahydro-4H-pyrrolo[3,2-c]pyridin-4-one,
1-ethyl-2-(2-methylpyridin-4-yl)-3-(phenylamino)-1,5,6,7-tetrahydro-4H-pyrrolo[3,2-c]pyridin-4-one,
N-{4-[4-oxo-3-(phenylamino)-4,5,6,7-tetrahydro-1H-pyrrolo[3,2-c]pyridin-2-yl]pyridin-2-yl}acetamide,
N-{4-[1-ethyl-4-oxo-3-(phenylamino)-4,5,6,7-tetrahydro-1H-pyrrolo[3,2-c]pyridin-2-yl]pyridin-2-yl}acetamide,
2-(3-fluoropyridin-4-yl)-3-(phenylamino)-1,5-dihydro-4H-pyrrolo[3,2-c]pyridin-4-one,
2-(3-fluoropyridin-4-yl)-3-(phenylamino)-1,5,6,7-tetrahydro-4H-pyrrolo[3,2-c]pyridin-4-one,
1-ethyl-3-{4-[4-oxo-3-(phenylamino)-4,5,6,7-tetrahydro-1H-pyrrolo[3,2-c]pyridin-2-yl]pyridin-2-yl}urea,
5-methyl-3-(phenylamino)-2-(pyridin-4-yl)-1,5,6,7-tetrahydro-4H-pyrrolo[3,2-c]pyridin-4-one,
2-(2-aminopyridin-4-yl)-5-methyl-3-(phenylamino)-1,5,6,7-tetrahydro-4H-pyrrolo[3,2-c]pyridin-4-one,
2-methyl-N-{4-[5-(2-methylpropanoyl)-4-oxo-3-(phenylamino)-4,5,6,7-tetrahydro-1H-pyrrolo[3,2-c]pyridin-2-yl]pyridin-2-yl}propanamide,
2-(3-fluoropyridin-4-yl)-5-methyl-3-(phenylamino)-1,5,6,7-tetrahydro-4H-pyrrolo[3,2-c]pyridin-4-one,
2-(3-methoxypyridin-4-yl)-5-methyl-3-(phenylamino)-1,5,6,7-tetrahydro-4H-pyrrolo[3,2-c]pyridin-4-one,
N-{4-[5-methyl-4-oxo-3-(phenylamino)-4,5,6,7-tetrahydro-1H-pyrrolo[3,2-c]pyridin-2-yl]pyridin-2-yl}acetamide,
N-{4-[5-methyl-4-oxo-3-(phenylamino)-4,5,6,7-tetrahydro-1H-pyrrolo[3,2-c]pyridin-2-yl]pyridin-2-yl}cyclopropanecarboxamide,
(1R,2R)-2-fluoro-N-{4-[5-methyl-4-oxo-3-(phenylamino)-4,5,6,7-tetrahydro-1H-pyrrolo[3,2-c]pyridin-2-yl]pyridin-2-yl}cyclopropanecarboxamide,
2-[3-(2-hydroxyethoxy)pyridin-4-yl]-5-methyl-3-(phenylamino)-1,5,6,7-tetrahydro-4H-pyrrolo[3,2-c]pyridin-4-one,
2-[3-(cyclopropylmethoxy)pyridin-4-yl]-5-methyl-3-(phenylamino)-1,5,6,7-tetrahydro-4H-pyrrolo[3,2-c]pyridin-4-one,
5-methyl-3-(phenylamino)-2-(3-propoxypyridin-4-yl)-1,5,6,7-tetrahydro-4H-pyrrolo[3,2-c]pyridin-4-one,
2-[3-(2,2-difluoroethoxy)pyridin-4-yl]-5-methyl-3-(phenylamino)-1,5,6,7-tetrahydro-4H-pyrrolo[3,2-c]pyridin-4-one,
5-methyl-3-(phenylamino)-2-[3-(2,2,2-trifluoroethoxy)pyridin-4-yl]-1,5,6,7-tetrahydro-4H-pyrrolo[3,2-c]pyridin-4-one,
2-[3-(2-methoxyethoxy)pyridin-4-yl]-5-methyl-3-(phenylamino)-1,5,6,7-tetrahydro-4H-pyrrolo[3,2-c]pyridin-4-one,
2-[3-(benzyloxy)pyridin-4-yl]-5-methyl-3-(phenylamino)-1,5,6,7-tetrahydro-4H-pyrrolo[3,2-c]pyridin-4-one,
5-methyl-3-(phenylamino)-2-[3-(3,3,3-trifluoropropoxy)pyridin-4-yl]-1,5,6,7-tetrahydro-4H-pyrrolo[3,2-c]pyridin-4-one,
5-methyl-3-(phenylamino)-2-{3-[(3S)-tetrahydrofuran-3-ylmethoxy]pyridin-4-yl}-1,5,6,7-tetrahydro-4H-pyrrolo[3,2-c]pyridin-4-one,
2-[3-(3,3-dimethylbutoxy)pyridin-4-yl]-5-methyl-3-(phenylamino)-1,5,6,7-tetrahydro-4H-pyrrolo[3,2-c]pyridin-4-one,
2-(3H-imidazo[4,5-b]pyridin-7-yl)-5-methyl-3-(phenylamino)-1,5,6,7-tetrahydro-4H-pyrrolo[3,2-c]pyridin-4-one,
2-[3-(cyclopropylmethoxy)pyridin-4-yl]-3-[(3,4-difluorophenyl)amino]-1,5,6,7-tetrahydro-4H-pyrrolo[3,2-c]pyridin-4-one,
2-[3-(cyclopropyl methoxy)pyridin-4-yl]-3-[(4-fluorophenyl)amino]-1,5,6,7-tetrahydro-4H-pyrrolo[3,2-c]pyridin-4-one,
2-[3-(cyclopropyl methoxy)pyridin-4-yl]-3-[(3-fluorophenyl)amino]-1,5,6,7-tetrahydro-4H-pyrrolo[3,2-c]pyridin-4-one, (1S,2S)-2-fluoro-N-{4-[5-methyl-4-oxo-3-(phenylamino)-4,5,6,7-tetrahydro-1H-pyrrolo[3,2-c]pyridin-2-yl]pyridin-2-yl}cyclopropanecarboxamide, 2-[3-(2,2-difluoroethoxy)pyridin-4-yl]-3-[(3-fluorophenyl)amino]-1,5,6,7-tetrahydro-4H-pyrrolo[3,2-c]pyridin-4-one, 2-[3-(2,2-difluoroethoxy)pyridin-4-yl]-3-[(4-fluorophenyl)amino]-1,5,6,7-tetrahydro-4H-pyrrolo[3,2-c]pyridin-4-one, 2-[3-(2,2-difluoroethoxy)pyridin-4-yl]-3-[(3,4-difluorophenyl)amino]-1,5,6,7-tetrahydro-4H-pyrrolo[3,2-c]pyridin-4-one, 2-{3-[2-(dimethylamino)ethoxy]pyridin-4-yl}-3-[(4-fluorophenyl)amino]-1,5,6,7-tetrahydro-4H-pyrrolo[3,2-c]pyridin-4-one, 3-[(3,4-difluorophenyl)amino]-2-[3-(2-methoxyethoxy)pyridin-4-yl]-1,5,6,7-tetrahydro-4H-pyrrolo[3,2-c]pyridin-4-one, 3-[(4-fluorophenyl)amino]-2-[3-(2-methoxyethoxy)pyridin-4-yl]-1,5,6,7-tetrahydro-4H-pyrrolo[3,2-c]pyridin-4-one, and 3-[(3-fluorophenyl)amino]-2-[3-(2-methoxyethoxy)pyridin-4-yl]-1,5,6,7-tetrahydro-4H-pyrrolo[3,2-c]pyridin-4-one, or an N-oxide, a salt, a tautomer or a stereoisomer of said compound, or a salt of said N-oxide, tautomer or stereoisomer.

One aspect of the invention are compounds of formula (I) as described in the examples, as characterized by their names in the title, as claimed in claim 6, and/or their structures as well as the subcombinations of all residues specifically disclosed in the compounds of the examples.

Another aspect of the present invention are the intermediates as used for their synthesis. One special aspect of the invention is intermediate (1-2),

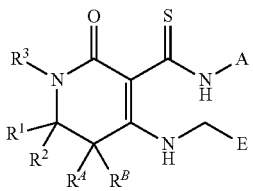

1-2 wherein $R^1$, $R^2$, $R^3$, $R^A$, $R^B$, A and E have the meaning provided in the aspects and embodiments described herein or according to any of claims 1 to 6.

Another aspect of the invention relates to the use of intermediate (1-2)

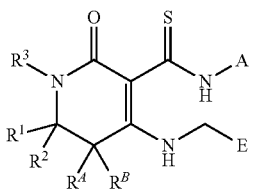

1-2 wherein $R^1$, $R^2$, $R^3$, $R^A$, $R^B$, A and E have the meaning provided in the aspects and embodiments described herein or according to any of claims 1 to 6 for preparing a compound of formula (I) as defined herein or an N-oxide, a salt, a tautomer or a stereoisomer of said compound, or a salt of said N-oxide, tautomer or stereoisomer.

Another aspect of the invention relates to the use of any of the intermediates described herein for preparing a compound of formula (I) as defined herein or an N-oxide, a salt, a tautomer or a stereoisomer of said compound, or a salt of said N-oxide, tautomer or stereoisomer.

Another aspect of the invention are compounds of formula (I),

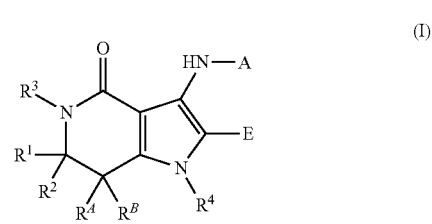

(I)

in which:
$R^1$ represents hydrogen, $C_1$-$C_6$-alkyl;
$R^2$ represents hydrogen, $C_1$-$C_6$-alkyl;
$R^3$ represents hydrogen, $C_1$-$C_4$-alkyl, $R^{11}$—C(O)— or $R^{11}$O—C(O)—;
$R^4$ represents hydrogen, $C_1$-$C_4$-alkyl or $C_1$-$C_4$-alkoxy-$C_2$-$C_4$-alkyl;
$R^A$ represents hydrogen;
$R^B$ represents hydrogen; or
$R^B$ and $R^2$ together form an additional bond;
A represents a group

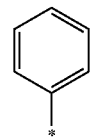 [SMILES: *c1ccccc1]

wherein * indicates the point of attachment of said group with the rest of the molecule and said group is optionally substituted, one or more times, independently of each other, with $R^5$;
$R^5$ represents halogen;
E represents a group:

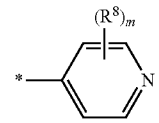

wherein * indicates the point of attachment of said group with the rest of the molecule;
$R^8$ represents, independently of each other, halogen, hydroxy, nitro, cyano, $C_1$-$C_4$-alkyl, $C_1$-$C_4$-haloalkyl, $C_1$-$C_6$-alkoxy, $R^9R^{10}$N—, $R^{11}$—C(O)—NH—, $R^{11}$O—C(O)—NH— or $R^9R^{10}$N—C(O)—NH—;
$R^9$, $R^{10}$ represent, independently of each other, hydrogen or $C_1$-$C_4$-alkyl,
$R^{11}$ represents, independently of each other, $C_1$-$C_4$-alkyl, $C_3$-$C_6$-cycloalkyl or $C_3$-$C_6$-halocycloalkyl;
m represents 0 or 1;
or an N-oxide, a salt, a tautomer or a stereoisomer of said compound, or a salt of said N-oxide, tautomer or stereoisomer.

In a further embodiment of the above-mentioned aspects, the invention relates to compounds of formula (I), wherein:
$R^1$ represents hydrogen, $C_1$-$C_6$-alkyl or $C_1$-$C_6$-haloalkyl;
$R^2$ represents hydrogen, $C_1$-$C_6$-alkyl or $C_1$-$C_6$-haloalkyl; or
$R^1$ and $R^2$ together with the carbon atom to which they are attached form a 3- to 6-membered cycloalkyl ring.

In a further embodiment of the above-mentioned aspects, the invention relates to compounds of formula (I), wherein:
$R^1$ represents hydrogen, $C_1$-$C_4$-alkyl or $C_1$-$C_4$-haloalkyl;
$R^2$ represents hydrogen, $C_1$-$C_4$-alkyl or $C_1$-$C_4$-haloalkyl; or
$R^1$ and $R^2$ together with the carbon atom to which they are attached form a 3- to 6-membered cycloalkyl ring.

In a further embodiment of the above-mentioned aspects, the invention relates to compounds of formula (I), wherein:
$R^1$ represents hydrogen, $C_1$-$C_6$-alkyl or $C_1$-$C_6$-haloalkyl.

In a further embodiment of the above-mentioned aspects, the invention relates to compounds of formula (I), wherein:
$R^1$ represents hydrogen, $C_1$-$C_4$-alkyl or $C_1$-$C_4$-haloalkyl.

In a further embodiment of the above-mentioned aspects, the invention relates to compounds of formula (I), wherein:
$R^1$ represents hydrogen or $C_1$-$C_4$-alkyl.

In a further embodiment of the above-mentioned aspects, the invention relates to compounds of formula (I), wherein:
$R^1$ represents hydrogen or methyl.

In a further embodiment of the above-mentioned aspects, the invention relates to compounds of formula (I), wherein:
$R^2$ represents hydrogen, $C_1$-$C_6$-alkyl or $C_1$-$C_6$-haloalkyl.

In a further embodiment of the above-mentioned aspects, the invention relates to compounds of formula (I), wherein:
$R^2$ represents hydrogen, $C_1$-$C_4$-alkyl or $C_1$-$C_4$-haloalkyl.

In a further embodiment of the above-mentioned aspects, the invention relates to compounds of formula (I), wherein:
$R^2$ represents hydrogen or $C_1$-$C_4$-alkyl.

In a further embodiment of the above-mentioned aspects, the invention relates to compounds of formula (I), wherein:
$R^2$ represents hydrogen or methyl.

In a further embodiment of the above-mentioned aspects, the invention relates to compounds of formula (I), wherein:
$R^1$ and $R^2$ together with the carbon atom to which they are attached form a 3- to 6-membered cycloalkyl ring, preferably a 3- to 4-membered cycloalkyl ring.

In a further embodiment of the above-mentioned aspects, the invention relates to compounds of formula (I), wherein:
$R^3$ represents hydrogen, $C_1$-$C_4$-alkyl, $C_1$-$C_4$-haloalkyl, $R^{11}$—C(O)—, $R^{11}$O—C(O)— or phenyl-$C_1$-$C_3$-alkyl, wherein said phenyl group is optionally substituted, one or more times, independently of each other, with $R^5$.

In a further embodiment of the above-mentioned aspects, the invention relates to compounds of formula (I), wherein:
$R^3$ represents hydrogen, $C_1$-$C_4$-alkyl, $C_1$-$C_4$-haloalkyl, $R^{11}$—C(O)— or $R^{11}$O—C(O)—.

In a further embodiment of the above-mentioned aspects, the invention relates to compounds of formula (I), wherein:
$R^3$ represents hydrogen, $C_1$-$C_4$-alkyl, $R^{11}$—C(O)— or $R^{11}$O—C(O)—.

In a further embodiment of the above-mentioned aspects, the invention relates to compounds of formula (I), wherein:
$R^3$ represents hydrogen, methyl, iso-propyl-C(O)— or tert-butyl-O—C(O)—.

In a further embodiment of the above-mentioned aspects, the invention relates to compounds of formula (I), wherein:
$R^4$ represents hydrogen, $C_1$-$C_4$-alkyl or $C_1$-$C_4$-alkoxy-$C_2$-$C_4$-alkyl.

In a further embodiment of the above-mentioned aspects, the invention relates to compounds of formula (I), wherein:
$R^4$ represents hydrogen, $C_1$-$C_3$-alkyl or $C_1$-$C_2$-alkoxy-$C_2$-$C_3$-alkyl.

In a further embodiment of the above-mentioned aspects, the invention relates to compounds of formula (I), wherein:
$R^4$ represents hydrogen, ethyl or 2-methoxy-ethyl-.

In a further embodiment of the above-mentioned aspects, the invention relates to compounds of formula (I), wherein:
$R^A$ represents hydrogen, hydroxy or $C_1$-$C_4$-alkyl;
$R^B$ represents hydrogen; or
$R^B$ and $R^2$ together form an additional bond.

In a further embodiment of the above-mentioned aspects, the invention relates to compounds of formula (I), wherein:
$R^A$ represents hydrogen;
$R^B$ represents hydrogen; or
$R^B$ and $R^2$ together form an additional bond.

In a further embodiment of the above-mentioned aspects, the invention relates to compounds of formula (I), wherein:
$R^A$ represents hydrogen, hydroxy or $C_1$-$C_4$-alkyl.

In a further embodiment of the above-mentioned aspects, the invention relates to compounds of formula (I), wherein:
$R^A$ represents hydrogen or $C_1$-$C_4$-alkyl.

In a further embodiment of the above-mentioned aspects, the invention relates to compounds of formula (I), wherein:
$R^A$ represents hydrogen or hydroxy.

In a further embodiment of the above-mentioned aspects, the invention relates to compounds of formula (I), wherein:
$R^A$ represents hydrogen.

In a further embodiment of the above-mentioned aspects, the invention relates to compounds of formula (I), wherein:
$R^B$ represents hydrogen.

In a further embodiment of the above-mentioned aspects, the invention relates to compounds of formula (I), wherein:
$R^B$ and $R^2$ together form an additional bond.

In a further embodiment of the above-mentioned aspects, the invention relates to compounds of formula (I), wherein:
A represents a group:

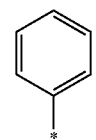 [SMILES: *c1ccccc1]

wherein * indicates the point of attachment of said group with the rest of the molecule and said group is optionally substituted, one or more times, independently of each other, with $R^5$.

In a further embodiment of the above-mentioned aspects, the invention relates to compounds of formula (I), wherein:
A represents phenyl, which is optionally substituted with one or more fluorine atoms, preferably optionally substituted with one fluorine atom.

In a further embodiment of the above-mentioned aspects, the invention relates to compounds of formula (I), wherein:
A represents phenyl, which is optionally substituted with one or more fluorine atoms, preferably optionally substituted with one or two fluorine atoms.

In a further embodiment of the above-mentioned aspects, the invention relates to compounds of formula (I), wherein:
$R^5$ represents hydroxy, halogen, cyano, $C_1$-$C_4$-alkyl, $C_1$-$C_4$-alkoxy, $C_1$-$C_4$-haloalkyl or $C_1$-$C_4$-haloalkoxy.

In a further embodiment of the above-mentioned aspects, the invention relates to compounds of formula (I), wherein:
$R^5$ represents halogen.

In a further embodiment of the above-mentioned aspects, the invention relates to compounds of formula (I), wherein:
$R^5$ represents fluorine.

In a further embodiment of the above-mentioned aspects, the invention relates to compounds of formula (I), wherein:
E represents a group selected from:

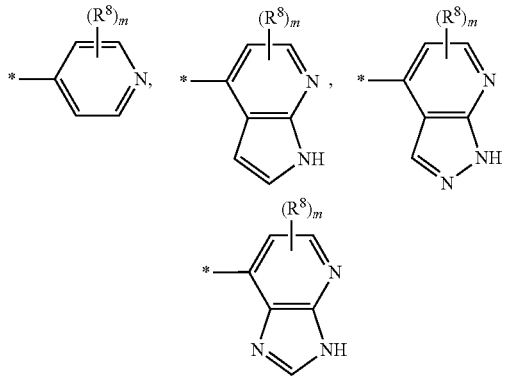

wherein * indicates the point of attachment of said group with the rest of the molecule;

In a further embodiment of the above-mentioned aspects, the invention relates to compounds of formula (I), wherein:
E represents a group selected from:

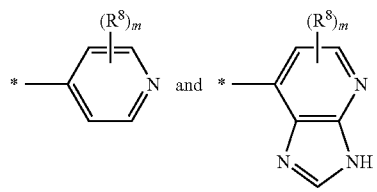

wherein * indicates the point of attachment of said group with the rest of the molecule;

In a further embodiment of the above-mentioned aspects, the invention relates to compounds of formula (I), wherein:
E represents a group selected from:

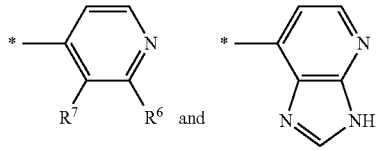

wherein * indicates the point of attachment of said group with the rest of the molecule;

In a further embodiment of the above-mentioned aspects, the invention relates to compounds of formula (I), wherein:
E represents a group:

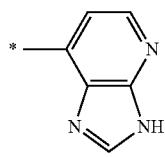

wherein * indicates the point of attachment of said group with the rest of the molecule;

In a further embodiment of the above-mentioned aspects, the invention relates to compounds of formula (I), wherein:
E represents a group:

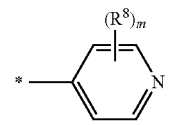

wherein * indicates the point of attachment of said group with the rest of the molecule.

In a further embodiment of the above-mentioned aspects, the invention relates to compounds of formula (I), wherein:
E represents a group:

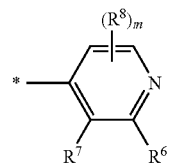

wherein * indicates the point of attachment of said group with the rest of the molecule; in which $R^6$, $R^7$ have the meaning as given for general formula (I) in any of claims 3 to 6, $R^8$, independently of each other, have the meaning as given for general formula (I) in claim 1 or 2, and m is 0, 1 or 2.

In a further embodiment of the above-mentioned aspects, the invention relates to compounds of formula (I), wherein:
E represents a group:

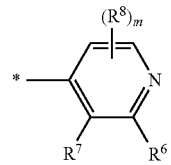

wherein * indicates the point of attachment of said group with the rest of the molecule; in which $R^6$, $R^7$ represent, independently of each other, hydrogen, halogen, hydroxy, cyano, $C_1$-$C_4$-alkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—;

$R^8$ represents, independently of each other, halogen, hydroxy, nitro, cyano, $C_1$-$C_4$-alkyl, $C_1$-$C_4$-haloalkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—;

m is 0, 1 or 2.

In a further embodiment of the above-mentioned aspects, the invention relates to compounds of formula (I), wherein:
E represents a group:

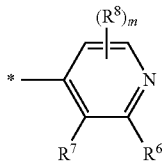

wherein * indicates the point of attachment of said group with the rest of the molecule; in which
$R^6$, $R^7$ represent, independently of each other, hydrogen, halogen, $C_1$-$C_4$-alkyl, $R^9R^{10}N$—, $R^{11}$—C(O)—NH— or $R^9R^{10}N$—C(O)—NH—;
$R^8$ represents, independently of each other, halogen, hydroxy, nitro, cyano, $C_1$-$C_4$-alkyl, $C_1$-$C_4$-haloalkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—;
m is 0, 1 or 2.

In a further embodiment of the above-mentioned aspects, the invention relates to compounds of formula (I), wherein:
E represents a group:

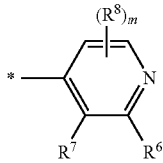

wherein * indicates the point of attachment of said group with the rest of the molecule; in which
$R^6$ represents hydrogen, methyl, $H_2N$—, $R^{11}$—C(O)—NH— or $R^9R^{10}N$—C(O)—NH—;
$R^7$ represents hydrogen, fluorine or methyl;
$R^8$ represents, independently of each other, halogen, hydroxy, nitro, cyano, $C_1$-$C_4$-alkyl, $C_1$-$C_4$-haloalkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—;
m is 0, 1 or 2.

In a further embodiment of the above-mentioned aspects, the invention relates to compounds of formula (I), wherein:
E represents a group:

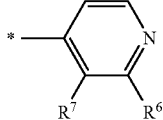

wherein * indicates the point of attachment of said group with the rest of the molecule.

In a further embodiment of the above-mentioned aspects, the invention relates to compounds of formula (I), wherein:
$R^6$, $R^7$ represent, independently of each other, hydrogen, halogen, hydroxy, cyano, $C_1$-$C_4$-alkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—.

In a further embodiment of the above-mentioned aspects, the invention relates to compounds of formula (I), wherein:
$R^6$, $R^7$ represent, independently of each other, hydrogen, halogen, $C_1$-$C_4$-alkyl, $R^9R^{10}N$—, $R^{11}$—C(O)—NH— or $R^9R^{10}N$—C(O)—NH—.

In a further embodiment of the above-mentioned aspects, the invention relates to compounds of formula (I), wherein:
$R^6$, $R^7$ represent, independently of each other, hydrogen, halogen, hydroxy, cyano, $C_1$-$C_4$-alkyl, $C_1$-$C_6$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)— NH— or $R^9R^{10}N$—C(O)—NH—.
wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally substituted one or more times, independently of each other, with $R^5$;

In a further embodiment of the above-mentioned aspects, the invention relates to compounds of formula (I), wherein:
$R^6$, $R^7$ represent, independently of each other, hydrogen, halogen, $C_1$-$C_4$-alkyl, $C_1$-$C_6$-alkoxy, $R^9R^{10}N$—, $R^{11}$—C(O)—NH— or $R^9R^{10}N$—C(O)—NH—.
wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally substituted one or more times, independently of each other, with $R^5$;

In a further embodiment of the above-mentioned aspects, the invention relates to compounds of formula (I), wherein:
$R^6$ represents hydrogen, halogen, hydroxy, cyano, $C_1$-$C_4$-alkoxy, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—.

In a further embodiment of the above-mentioned aspects, the invention relates to compounds of formula (I), wherein:
$R^6$ represents, independently of each other, hydrogen, $C_1$-$C_4$-alkyl, $R^9R^{10}N$—, $R^{11}$—C(O)—NH— or $R^9R^{10}N$—C(O)—NH—.

In a further embodiment of the above-mentioned aspects, the invention relates to compounds of formula (I), wherein:
$R^6$ represents hydrogen, methyl, $H_2N$—, $R^{11}$—C(O)—NH— or $R^9R^{10}N$—C(O)—NH—.

In a further embodiment of the above-mentioned aspects, the invention relates to compounds of formula (I), wherein:
$R^7$ represents hydrogen, halogen, hydroxy, cyano, $C_1$-$C_4$-alkoxy, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—.

In a further embodiment of the above-mentioned aspects, the invention relates to compounds of formula (I), wherein:
$R^7$ represents, independently of each other, hydrogen, halogen or $C_1$-$C_4$-alkyl.

In a further embodiment of the above-mentioned aspects, the invention relates to compounds of formula (I), wherein:
$R^7$ represents hydrogen, fluorine or methyl.

In a further embodiment of the above-mentioned aspects, the invention relates to compounds of formula (I), wherein:
$R^7$ represents hydrogen, halogen, hydroxy, cyano, $C_1$-$C_6$-alkoxy, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)— NH— or $R^9R^{10}N$—C(O)—NH—.
wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally substituted one or more times, independently of each other, with $R^5$;

In a further embodiment of the above-mentioned aspects, the invention relates to compounds of formula (I), wherein:
$R^7$ represents, independently of each other, hydrogen, halogen, $C_1$-$C_4$-alkyl or $C_1$-$C_6$-alkoxy,
wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N$—, $C_3$-$C_6$-cycloalkyl, 5- to 6-membered heterocycloalkyl or phenyl, which is optionally substituted, one or more times, independently of each other, with $R^5$;

In a further embodiment of the above-mentioned aspects, the invention relates to compounds of formula (I), wherein:
$R^7$ represents hydrogen, fluorine, methyl or $C_1$-$C_6$-alkoxy, wherein said $C_1$-$C_6$-alkoxy is optionally substituted one, two or three times with fluoro or is optionally substituted one time with hydroxy, methoxy, $(CH_3)_2N$—, cyclopropyl, tetrahydrofuran-3-yl or phenyl;

In a further embodiment of the above-mentioned aspects, the invention relates to compounds of formula (I), wherein:
$R^7$ represents hydrogen, fluoro, methyl, methoxy, cyclopropylmethoxy-, tetrahydrofuran-3-ylmethoxy-, 2-hydroxyethoxy-, 2-m ethoxyethoxy-, 2,2-difluoroethoxy, 2,2,2-trifluoroethoxy, 2-(dimethylamino)ethoxy-, 3,3,3-trifluoropropoxy, propoxy, butoxy, 3,3-dimethylbutoxy or benzyloxy, In a further embodiment of the above-mentioned aspects, the invention relates to compounds of formula (I), wherein:
$R^8$ represents, independently of each other, halogen, hydroxy, nitro, cyano, $C_1$-$C_4$-alkyl, $C_1$-$C_4$-haloalkyl, $C_1$-$C_4$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—.

In a further embodiment of the above-mentioned aspects, the invention relates to compounds of formula (I), wherein:
$R^8$ represents, independently of each other, hydrogen, halogen, $C_1$-$C_4$-alkyl, $R^9R^{10}N$—, $R^{11}$—C(O)—NH— or $R^9R^{10}N$—C(O)—NH—.

In a further embodiment of the above-mentioned aspects, the invention relates to compounds of formula (I), wherein:
$R^8$ represents, independently of each other, halogen, hydroxy, nitro, cyano, $C_1$-$C_4$-alkyl, $C_1$-$C_4$-haloalkyl, $C_1$-$C_6$-alkoxy, $C_3$-$C_6$-cycloalkyl, $C_3$-$C_6$-halocycloalkyl, $R^9R^{10}N$—, $R^{11}$—C(O)—NH—, $R^{11}$O—C(O)—NH— or $R^9R^{10}N$—C(O)—NH—.
wherein said $C_1$-$C_6$-alkoxy is optionally substituted one, two or three times, independently of each other, with halogen and is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally substituted one or more times, independently of each other, with $R^5$.

In a further embodiment of the above-mentioned aspects, the invention relates to compounds of formula (I), wherein:
$R^8$ represents, independently of each other, halogen, $C_1$-$C_4$-alkyl, $C_1$-$C_6$-alkoxy, $R^9R^{10}N$—, $R^{11}$—C(O)—NH— or $R^9R^{10}N$—C(O)—NH—.
wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally substituted, one or more times, independently of each other, with $R^5$.

In a further embodiment of the above-mentioned aspects, the invention relates to compounds of formula (I), wherein:
$R^8$ represents, independently of each other, halogen, $C_1$-$C_4$-alkyl, $C_1$-$C_6$-alkoxy, $R^9R^{10}N$—, $R^{11}$—C(O)—NH— or $R^9R^{10}N$—C(O)—NH—.
wherein said $C_1$-$C_6$-alkoxy is optionally substituted one, two or three times, independently of each other, with halogen or is optionally substituted one time with hydroxy, $C_1$-$C_4$-alkoxy, $R^9R^{10}N$—, $C_3$-$C_6$-cycloalkyl, 5- to 6-membered heterocycloalkyl or phenyl.

In a further embodiment of the above-mentioned aspects, the invention relates to compounds of formula (I), wherein:
$R^9$, $R^{10}$ represent, independently of each other, hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally substituted, one or more times, independently of each other, with $R^5$, or
$R^9$ and $R^{10}$ together with the nitrogen atom to which they are attached form a 3- to 6-membered nitrogen containing heterocyclic ring, optionally containing one additional heteroatom or heteroatom containing group selected from O, NH and S, and which may be optionally substituted, one or more times, independently of each other, with $R^5$.

In a further embodiment of the above-mentioned aspects, the invention relates to compounds of formula (I), wherein:
$R^9$, $R^{10}$ represent, independently of each other, hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally substituted with $R^5$.

In a further embodiment of the above-mentioned aspects, the invention relates to compounds of formula (I), wherein:
$R^9$, $R^{10}$ represent, independently of each other, hydrogen, $C_1$-$C_4$-alkyl, $C_3$-$C_6$-cycloalkyl, $C_3$-$C_6$-halocycloalkyl or $C_1$-$C_4$-haloalkyl.

In a further embodiment of the above-mentioned aspects, the invention relates to compounds of formula (I), wherein:
$R^9$, $R^{10}$ represent, independently of each other, hydrogen or $C_1$-$C_4$-alkyl.

In a further embodiment of the above-mentioned aspects, the invention relates to compounds of formula (I), wherein:
$R^9$, $R^{10}$ represent, independently of each other, hydrogen or ethyl.

In a further embodiment of the above-mentioned aspects, the invention relates to compounds of formula (I), wherein:
$R^9$ and $R^{10}$ together with the nitrogen atom to which they are attached form a 3- to 6-membered nitrogen containing heterocyclic ring, optionally containing one additional heteroatom or heteroatom containing group selected from O, NH or S, and which may be optionally substituted, one or more times, independently of each other, with $R^5$.

In a further embodiment of the above-mentioned aspects, the invention relates to compounds of formula (I), wherein:
$R^9$ represents, independently of each other, hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally substituted with $R^5$.

In a further embodiment of the above-mentioned aspects, the invention relates to compounds of formula (I), wherein:
$R^9$ represents, independently of each other, hydrogen or $C_1$-$C_4$-alkyl.

In a further embodiment of the above-mentioned aspects, the invention relates to compounds of formula (I), wherein:
$R^9$ represents, independently of each other, hydrogen, $C_1$-$C_4$-alkyl, $C_3$-$C_6$-cycloalkyl, $C_3$-$C_6$-halocycloalkyl or $C_1$-$C_4$-haloalkyl.

In a further embodiment of the above-mentioned aspects, the invention relates to compounds of formula (I), wherein:
$R^{10}$ represents, independently of each other, hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally substituted with $R^5$.

In a further embodiment of the above-mentioned aspects, the invention relates to compounds of formula (I), wherein:
$R^{10}$ represents, independently of each other, hydrogen or $C_1$-$C_4$-alkyl.

In a further embodiment of the above-mentioned aspects, the invention relates to compounds of formula (I), wherein:
$R^{10}$ represents, independently of each other, hydrogen, $C_1$-$C_4$-alkyl, $C_3$-$C_6$-cycloalkyl, $C_3$-$C_6$-halocycloalkyl or $C_1$-$C_4$-haloalkyl.

In a further embodiment of the above-mentioned aspects, the invention relates to compounds of formula (I), wherein:
$R^{11}$ represents, independently of each other, $C_1$-$C_4$-alkyl, $C_3$-$C_6$-cycloalkyl, $C_1$-$C_4$-haloalkyl or $C_3$-$C_6$-halocycloalkyl.

In a further embodiment of the above-mentioned aspects, the invention relates to compounds of formula (I), wherein:
$R^{11}$ represents, independently of each other, $C_1$-$C_4$-alkyl, $C_3$-$C_6$-cycloalkyl or $C_3$-$C_6$-halocycloalkyl.

In a further embodiment of the above-mentioned aspects, the invention relates to compounds of formula (I), wherein:
$R^{11}$ represents, independently of each other, $C_1$-$C_4$-alkyl, cyclopropyl or fluorocyclopropyl.

In a further embodiment of the above-mentioned aspects, the invention relates to compounds of formula (I), wherein:
$R^{11}$ represents, independently of each other, methyl, isopropyl, tert-butyl, cyclopropyl or fluorocyclopropyl;

In a further embodiment of the above-mentioned aspects, the invention relates to compounds of formula (I), wherein:
$R^{11}$ represents, independently of each other, $C_1$-$C_4$-alkyl.

In a further embodiment of the above-mentioned aspects, the invention relates to compounds of formula (I), wherein:
$R^{11}$ represents, independently of each other, methyl or isopropyl.

In a further embodiment of the above-mentioned aspects, the invention relates to compounds of formula (I), wherein:
$R^{11}$ represents, independently of each other, methyl, isopropyl or tert-butyl.

In a further embodiment of the above-mentioned aspects, the invention relates to compounds of formula (I), wherein:
m represents 0, 1, 2 or 3.

In a further embodiment of the above-mentioned aspects, the invention relates to compounds of formula (I), wherein:
m represents 0, 1 or 2.

In a further embodiment of the above-mentioned aspects, the invention relates to compounds of formula (I), wherein:
m represents 0 or 1.

In a further embodiment of the above-mentioned aspects, the invention relates to compounds of formula (I), wherein:
m represents 0.

In a further embodiment of the above-mentioned aspects, the invention relates to compounds of formula (I), wherein:
n represents 0, 1, or 2;

In a further embodiment of the above-mentioned aspects, the invention relates to compounds of formula (I), wherein:
n represents 0, or 1.

In a further embodiment of the above-mentioned aspects, the invention relates to compounds of formula (I), wherein:
n represents 0.

Another aspect of the invention are compounds of formula (I) supra, wherein said compounds of formula (I) are compounds of formula (Ia)

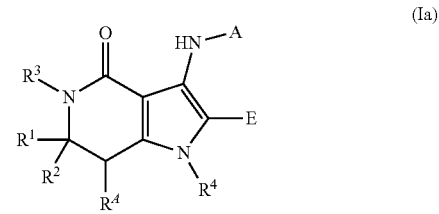

wherein $R^1$, $R^2$, $R^3$, $R^4$, $R^A$, A and E have the meaning as described in the aspects and embodiments supra; or an N-oxide, a salt, a tautomer or a stereoisomer of said compound, or a salt of said N-oxide, tautomer or stereoisomer.

Another aspect of the invention are compounds of formula (I) supra, wherein said compounds of formula (I) are compounds of formula (Ib)

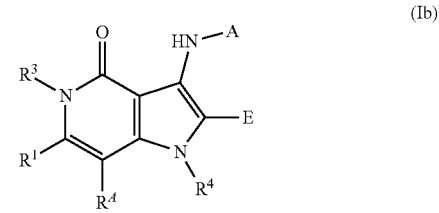

wherein $R^1$, $R^3$, $R^4$, $R^A$, A and E have the meaning as described in the aspects and embodiments supra; or an N-oxide, a salt, a tautomer or a stereoisomer of said compound, or a salt of said N-oxide, tautomer or stereoisomer.

Another aspect of the invention relates to compounds of formula (Ib) supra in which:
$R^1$ represents hydrogen; and
$R^3$ represents hydrogen; and
$R^4$ represents hydrogen; and
A represents a phenyl group; and
E represents a group:

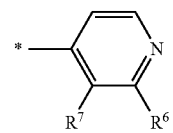

wherein * indicates the point of attachment of said group with the rest of the molecule; and
$R^6$, $R^7$ represent, independently of each other, hydrogen or halogen;
or an N-oxide, a salt, a tautomer or a stereoisomer of said compound, or a salt of said N-oxide, tautomer or stereoisomer.

A further aspect of the invention are compounds of formula (I), which are present as their salts.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

Another embodiment of the invention are compounds according to the claims as disclosed in the Claims section wherein the definitions are limited according to the preferred or more preferred definitions as disclosed below or specifically disclosed residues of the exemplified compounds and subcombinations thereof.

Definitions

Constituents which are optionally substituted as stated herein, may be substituted, unless otherwise noted, one or more times, independently of one another at any possible position. When any variable occurs more than one time in any constituent, each definition is independent. For example, when $R^1$, $R^2$, $R^3$, $R^4$, $R^5$, $R^6$, $R^7$, $R^8$, $R^9$, $R^{10}$ and/or $R^{11}$, occur more than one time in any compound of formula (I) each definition of $R^1$, $R^2$, $R^3$, $R^4$, $R^5$, $R^6$, $R^7$, $R^8$, $R^9$, $R^{10}$ and $R^{11}$ is independent.

Should a constituent be composed of more than one part, e.g. $C_1$-$C_4$-alkoxy-$C_2$-$C_4$-alkyl, the position of a possible substituent can be at any of these parts at any suitable position. A hyphen at the beginning or at the end of the constituent marks the point of attachment to the rest of the molecule. Should a ring be substituted the substituent could be at any suitable position of the ring, also on a ring nitrogen atom if suitable.

The term "comprising" when used in the specification includes "consisting of".

If it is referred to "as mentioned above" or "mentioned above", "supra" within the description it is referred to any of the disclosures made within the specification in any of the preceding pages.

If it is referred to "as mentioned herein", "described herein", "provided herein" or "stated herein" within the description it is referred to any of the disclosures made within the specification in any of the preceding or subsequent pages.

"suitable" within the sense of the invention means chemically possible to be made by methods within the knowledge of a skilled person.

The terms as mentioned in the present text have preferably the following meanings:

The term "halogen atom", "halo-" or "Hal-" is to be understood as meaning a fluorine, chlorine, bromine or iodine atom, preferably a fluorine, chlorine, bromine or iodine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl or iso-propyl group.

The term "$C_1$-$C_6$-haloalkyl" is to be understood as meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said $C_1$-$C_6$-haloalkyl group is, for example, —$CF_3$, —$CHF_2$, —$CH_2F$, —$CF_2CF_3$, —$CH_2CH_2F$, —$CH_2CHF_2$, —$CH_2CF_3$, —$CH_2CH_2CF_3$, or —$CH(CH_2F)_2$. Particularly, said group has 1, 2, 3 or 4 carbon atoms ("$C_1$-$C_4$-haloalkyl").

The term "$C_1$-$C_4$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy or sec-butoxy group, or an isomer thereof.

The term "$C_1$-$C_4$-haloalkoxy" is to be understood as meaning a linear or branched, saturated, monovalent $C_1$-$C_4$-alkoxy group, as defined supra, in which one or more of the hydrogen atoms is replaced, in identically or differently, by a halogen atom. Particularly, said halogen atom is F. Said $C_1$-$C_4$-haloalkoxy group is, for example, —$OCF_3$, —$OCHF_2$, —$OCH_2F$, —$OCF_2CF_3$, or —$OCH_2CF_3$.

The term "$C_1$-$C_4$-alkoxy-$C_2$-$C_4$-alkyl" is to be understood as meaning a linear or branched, saturated, monovalent alkyl group, as defined supra, in which one or more of the hydrogen atoms is replaced, in identically or differently, by a $C_1$-$C_4$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl or sec-butoxyalkyl group, in which the term "$C_2$-$C_4$-alkyl" is defined supra, or an isomer thereof.

The term "$C_3$-$C_6$-cycloalkyl" is to be understood as meaning a saturated, monovalent, mono- or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl, or a bicyclic hydrocarbon ring.

The term "$C_3$-$C_6$-halocycloalkyl" is to be understood as meaning a saturated, monovalent, mono- or bicyclic hydrocarbon ring which contains 3, 4, 5 or 6 carbon atoms in which the term "$C_3$-$C_6$-cycloalkyl" is defined supra, and in which one or more hydrogen atoms are replaced by a halogen atom, identically or differently, i.e. one halogen atom being independent from another. Particularly, said halogen atom is F, Cl, Br or I. More particularly, said halogen is F.

The term "3- to 6-membered cycloalkyl ring" is to be understood as meaning a saturated, monovalent, mono- or bicyclic hydrocarbon ring which contains 3, 4, 5 or 6 carbon atoms. Said 3- to 6-membered cycloalkyl ring is for example, a monocyclic hydrocarbon ring, e.g. a cyclopropyl, cyclobutyl, cyclopentyl or cyclohexyl, or a bicyclic hydrocarbon ring.

The term "3- to 6-membered nitrogen containing heterocyclic ring", is to be understood as meaning a saturated or partially unsaturated, monovalent, mono- or bicyclic hydrocarbon ring which contains 2, 3, 4, 5 or 5, carbon atoms, and one nitrogen atom, optionally containing one further heteroatom (or a heteroatom-containing group) selected from the group consisting of O, S, and NH. When $R^9$ and $R^{10}$ together with the nitrogen atom to which they are attached form a 3- to 6-membered nitrogen containing heterocyclic ring, said heterocyclocic ring is connected to the rest of the molecule via a nitrogen atom.

Particularly, said 3- to 6-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, or a 5-membered ring, such as tetrahydrofuranyl, pyrrolidinyl, imidazolidinyl, pyrazolidinyl, pyrrolinyl, or a 6-membered ring, such as tetrahydropyranyl, piperidinyl, morpholinyl, thiomorpholinyl or piperazinyl. Optionally, said heterocycloalkyl can be benzo fused.

The term "4- to 7-membered heterocycloalkyl" or "4- to 7-membered heterocyclic ring", is to be understood as meaning a saturated or partially unsaturated, monovalent, mono- or bicyclic hydrocarbon ring which contains 3, 4, 5 or 6, carbon atoms, and one or more heteroatom-containing groups selected from O, S, S(=O), S(=O)$_2$, and NR10, in which $R^{11}$ is as defined herein; optionally one ring carbon atom is replaced with a C(=O) group, it being possible for said heterocycloalkyl group to be attached to the rest of the molecule via any one of the carbon atoms or, if present, the nitrogen atom.

Particularly, said 4- to 7-membered heterocycloalkyl can contain 3, 4, or 5 carbon atoms, and one or more of the above-mentioned heteroatom-containing groups (a "4- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl or 4H-[1,4]thiazinyl ring, for example, or it may be benzo-fused, such as, without being limited thereto, a dihydroisoquinolinyl ring, for example.

The term "C$_1$-C$_6$", as used throughout this text, e.g. in the context of the definition of "C$_1$-C$_6$-alkyl" or "C$_1$-C$_6$-haloalkyl" is to be understood as meaning an alkyl group having a finite number of carbon atoms of 1 to 6, i.e. 1, 2, 3, 4, 5 or 6 carbon atoms. It is to be understood further that said term "C$_1$-C$_6$" is to be interpreted as any sub-range comprised therein, e.g. C$_1$-C$_6$, C$_2$-C$_6$, C$_3$-C$_6$, C$_1$-C$_2$, C$_1$-C$_3$, particularly C$_1$-C$_2$, C$_1$-C$_3$, C$_1$-C$_4$, The term "C$_1$-C$_4$", as used throughout this text, e.g. in the context of the definition of "C$_1$-C$_4$-alkyl", "C$_1$-C$_4$-haloalkyl", "C$_1$-C$_4$-alkoxy", or "C$_1$-C$_4$-haloalkoxy" is to be understood as meaning an alkyl group having a finite number of carbon atoms of 1 to 4, i.e. 1, 2, 3 or 4 carbon atoms. It is to be understood further that said term "C$_1$-C$_4$" is to be interpreted as any sub-range comprised therein, e.g. C$_1$-C$_4$, C$_2$-C$_4$, C$_3$-C$_4$, C$_1$-C$_2$, C$_1$-C$_3$, particularly C$_1$-C$_2$, C$_1$-C$_3$, C$_1$-C$_4$, in the case of "C$_1$-C$_6$-haloalkyl" or "C$_1$-C$_4$-haloalkoxy" even more particularly C$_1$-C$_2$.

Further, as used herein, the term "C$_3$-C$_6$", as used throughout this text, e.g. in the context of the definition of "C$_3$-C$_6$-cycloalkyl", is to be understood as meaning a cycloalkyl group having a finite number of carbon atoms of 3 to 6, i.e. 3, 4, 5 or 6 carbon atoms. It is to be understood further that said term "C$_3$-C$_6$" is to be interpreted as any sub-range comprised therein, e.g. C$_3$-C$_6$, C$_4$-C$_5$, C$_3$-C$_5$, C$_3$-C$_4$, C$_4$-C$_6$, C$_5$-C$_6$ particularly C$_3$-C$_6$.

For the avoidance of doubt, in chemical formulas a methyl group present at the end of an alkyl residue or as a substitutent may be represented by *—CH$_3$ or by *—, in which * represents the point of attachment with the rest of the molecule (or alkyl moiety), as it is known by a skilled person, For the avoidance of doubt, when $R^1$ and $R^2$ together with the carbon atom to which they are attached form a 3- to 6-membered cycloalkyl ring, $R^B$ represents hydrogen (i.e. $R^B$ and $R^2$ together do not form an additional bond).

For the avoidance of doubt, when $R^B$ and $R^2$ together form an additional bond the compound of formula (I) is a compound of formula (Ib)

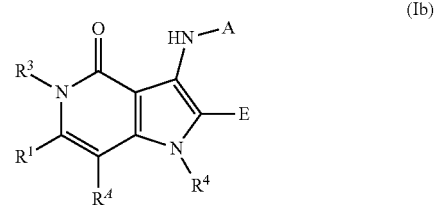

(Ib)

wherein $R^1$, $R^3$, $R^4$, $R^A$, A and E have the meaning as described in the aspects and embodiments supra; or an N-oxide, a salt, a tautomer or a stereoisomer of said compound, or a salt of said N-oxide, tautomer or stereoisomer.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The compounds of general formula (I) may exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I)

exhibiting an unnatural proportion of one or more of the isotopes that constitute such a compound.

The expression "unnatural proportion" is to be understood as meaning a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865) is a rapid route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1993; J. Atzrodt et al., Angew. Chem., Int. Ed. 2007, 46, 7744; K. Matoishi et al., J. Chem. Soc, Chem. Commun. 2000, 1519-1520; K. Kassahun et al., WO2012/112363. The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [A. Streitwieser et al., J. Am. Chem. Soc., 1963, 85, 2759; C. L. Perrin, et al., J. Am. Chem. Soc., 2007, 129, 4490], basicity [C. L. Perrin, et al., J. Am. Chem. Soc., 2003, 125, 15008; C. L. Perrin in Advances in Physical Organic Chemistry, 44, 144; C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, Calif., Oct. 12-16, 2008), ML-337 (C. J. Wenthur et al., J. Med. Chem., 2013, 56, 5208), and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

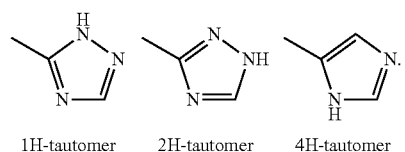

1H-tautomer    2H-tautomer    4H-tautomer

An example of tautomers of the present invention is shown below (these can exist alone or in any mixture of the three tautomers in any ratio).

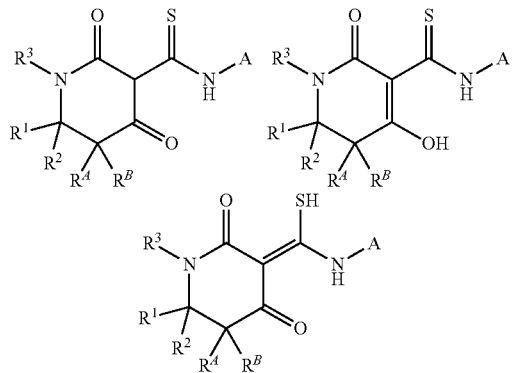

An example of tautomers of the present invention is shown below (these can exist alone or in any mixture of the three tautomers in any ratio).

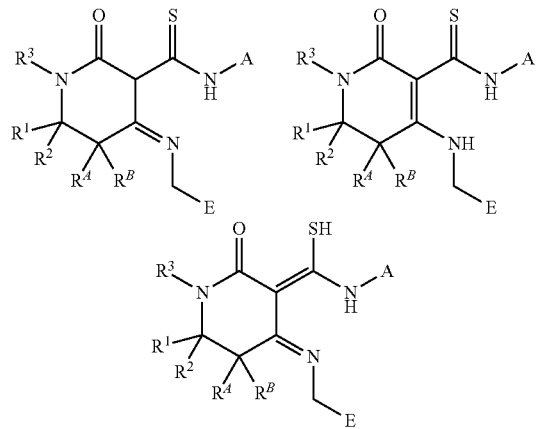

An example of tautomers of the present invention is shown below (these can exist alone or in any mixture of the three tautomers in any ratio).

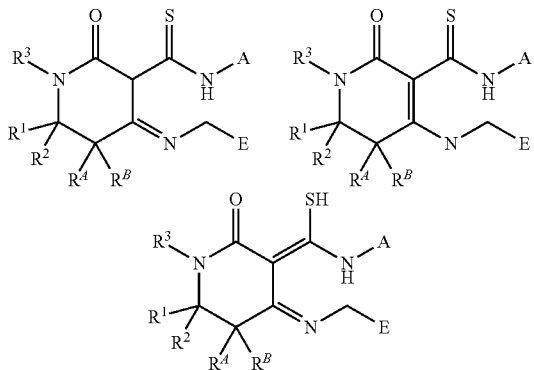

Another example of tautomers of the present invention is shown below for compounds of the present invention in which E represents:

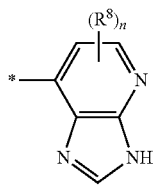

Compounds containing the above E group can exist alone or in any mixture of the below tautomers in any ratio:

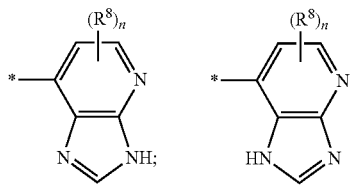

wherein * indicates the point of attachment of said group with the rest of the molecule.

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, C$_1$-C$_6$ alkoxymethyl esters, e.g. methoxymethyl, C$_1$-C$_6$ alkanoyloxymethyl esters, e.g. pivaloyloxymethyl, phthalidyl esters, C$_3$-C$_8$ cycloalkoxy-carbonyloxy-C$_1$-C$_6$ alkyl esters, e.g. 1-cyclohexylcarbonyloxyethyl, 1,3-dioxolen-2-onylmethyl esters, e.g. 5-methyl-1,3-dioxolen-2-onylmethyl, and C$_1$-C$_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of formula (I) of the present invention with an anti-cancer agent as defined below is an embodiment of the invention.

The term "(chemotherapeutic) anti-cancer agents" includes but is not limited to 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, paliferm in, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

It has now been found, and this constitutes the basis of the present invention, that said compounds of the present invention have surprising and advantageous properties.

In particular, said compounds of the present invention have surprisingly been found to effectively inhibit Bub1 kinase and may therefore be used for the treatment and prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The intermediates used for the synthesis of the compounds of claims 1-6 as described below, as well as their use for the synthesis of the compounds of claims 1-6, are one further aspect of the present invention. Preferred intermediates are the Intermediate Examples as disclosed below.

General Procedures

The compounds according to the invention can be prepared according to the following Schemes 1 through 4.

The Schemes and procedures described below illustrate synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents $R^1$, $R^2$, $R^3$, $R^4$, $R^A$ and $R^B$ can be achieved before and/or after the exemplified transformations. These modifications can be such as the introduction of protecting groups, cleavage of protecting groups, reduction or oxidation of functional groups, dehydrogenation, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in *Protective Groups in Organic Synthesis*, 3$^{rd}$ edition, Wiley 1999). Specific examples are described in the subsequent paragraphs.

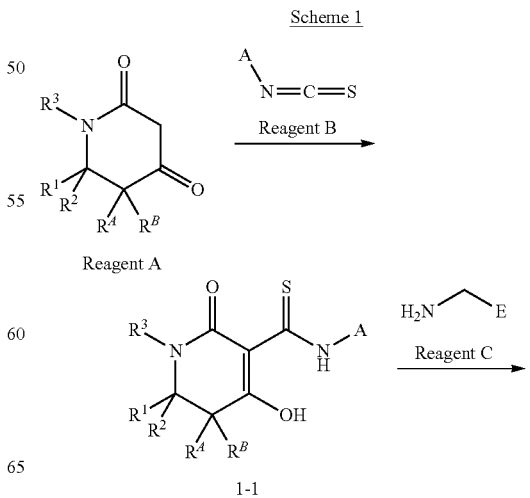

Scheme 1

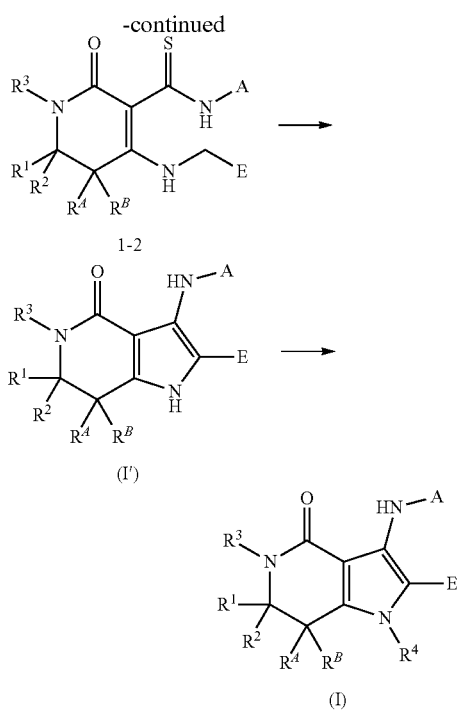

(I')

(I)

Scheme 1: Route for the preparation of compounds of general formula (I), wherein $R^1$, $R^2$, $R^3$, $R^4$, $R^A$, $R^B$, A and E have the meaning as given for general formula (I), supra. Reagent A, reagent B and reagent C are either commercially available or can be prepared according to procedures available from the public domain, as understandable to the person skilled in the art. Specific examples are described in the subsequent paragraphs.

A suitably substituted piperidine-2,4-dione of general formula (reagent A), such as, for example, piperidine-2,4-dione, can be reacted with a suitably substituted isothiocyanate (reagent B), such as, for example, phenylisothiocyanate, in a suitable solvent system, such as, for example, acetonitrile, in the presence of a suitable base, such as, for example, triethylamine or DBU, at temperatures ranging from −78° C. to +100° C. Preferably the reaction is carried out at 0° C. or +100° C. to furnish compounds of general formula (1-1). Similar reactions have been performed in the literature (D. E. Worrall, J. Am. Chem. Soc., 1940, 62, 675).

Intermediates of general formula (1-1) can be converted to Intermediates of general formula (1-2) by reaction with a suitable amine, such as, for example 1-(pyridin-4-yl)methanamine, in a suitable solvent system, such as, for example, ethanol and ethyl acetate, at a temperature between room temperature and the boiling point of the respective solvents, preferably the reaction is carried out at the boiling point of the respective solvents, whereby the water formed in the reaction is removed from the reaction by methods known to those skilled in the art, such as, for example, azeotropic removal of water (Dean-Stark conditions) or with molecular sieves, to furnish intermediates of general formula (1-2).

Intermediates of general formula (1-2) are reacted with a base and/or oxidizing reagent, preferably an oxidizing agent, such as, for example hydrogen peroxide or SIBX (stabilized iodoxybenzoic acid, in a suitable solvent system, such as, for example, methanol, in a temperature range from −30° C. to the boiling point of the respective solvent. Preferably the reaction is carried out at the boiling point of the respective solvent, to furnish intermediates of general formula (I').

Intermediates of general formula (I') are reacted with an alkylating agent which contain a suitable leaving group, such as, for example, Cl, Br, aryl sulfonate such as for example p-toluene sulfonate, or alkyl sulfonate such as for example methane sulfonate or trifluoromethane sulfonate, in the presence of a base, such as, for example sodium hydride, potassium carbonate, caesium carbonate, in a suitable solvent system, such as, for example, dimethylformamide, in a temperature range from 0° C. to the boiling point of the respective solvent, to furnish compounds of general formula (I).

Scheme 2

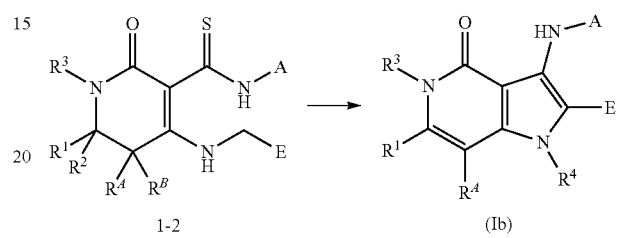

1-2      (Ib)

Scheme 2: Route for the preparation of compounds of general formula (Ib), wherein $R^1$, $R^2$, $R^3$, $R^4$, $R^A$, $R^B$, A and E have the meaning as given for general formula (I), supra.

Intermediates of general formula (1-2) are reacted under dehydrogenation conditions, such reactions are known (J. H. Hutchinson, et al., J. Med. Chem., 1996, 39, 4583-4591, N. L. Subasinghe, et al., Bioorg. Med. Chem. Lett., 2013, 23, 1063-1069, C. F. Jones, et al., Synlett, 2010, 654-658, M. Noguchi, et al., Bull. Chem. Soc. Japan, 1986, 59, 1355-1362). These conditions can be carried out using, for example, metal catalysis such as, for example, palladium on charcoal, in a suitable solvent system, such as, for example, dimethylacetamide, in a temperature range from 0° C. to 200° C. of the respective solvent, preferably at elevated temperatures, to furnish compounds of general formula (Ib).

Scheme 3

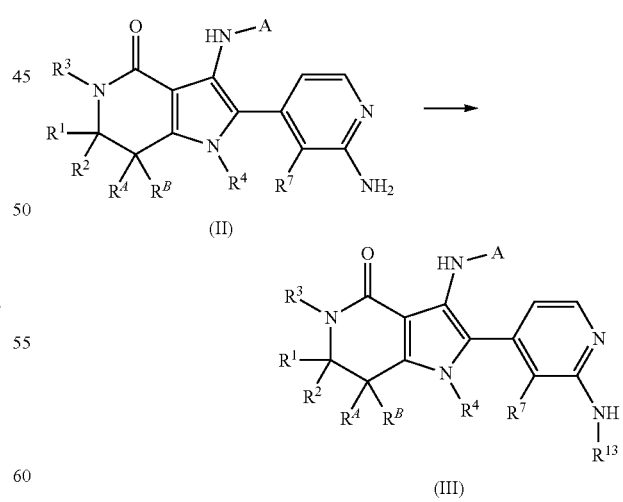

(II)

(III)

Scheme 3: Route for the preparation of compounds of general formula (III), wherein $R^1$, $R^2$, $R^3$, $R^4$, $R^A$, $R^B$, $R^7$ and A have the meaning as given for general formula (I), supra and $R^{13}$ represents $R^{11}$—C(O)—, $R^{11}$O—C(O)— or $R^9R^{10}$N—C(O)—.

Intermediates of general formula (II) are reacted with an acylating reagent, an acylating agent which can be generated in situ, to furnish compounds of general formula (III). These types of reactions are well-known (selected literature examples are: S. Miwatashi, et al., J. Med. Chem., 2005, 48, 5966-5979; J. Zhao, et al., Bioorg. Med. Chem. Lett., 2014, 24, 2802-2806; M. P. Hay, et al., J. Med. Chem., 2010, 53, 787-797; J. M. Keith, et al., Med. Chem. Lett, 2012, 3, 823-827; J. Liang, et al., Eur. J. Med. Chem., 2013, 67, 175-187).

Not-limiting examples of these types of reagents are:
i) carboxylic acid with dehydrating reagents typically used in amide bond formation, such as, for example (HBTU, HATU, PyBOP, BOP, T3P, EDC, DIC, DCC)
ii) acid fluorides, acid chlorides, acid bromides, preferably in the presence of a base
iii) acid anhydrides, preferably in the presence of a base
iv) chloroformates, preferably in the presence of a base
v) isocyanates, preferably in the presence of a base
vi) isothiocyanates, preferably in the presence of a base attached to each other to represent, for example, pincacol boronic esters. The substituent Z in the intermediates of general formulae 4-1, 4-4 and 4-6 can be a suitable leaving group, such as, for example, Cl, Br, I, aryl sulfonates such as for example p-toluene sulfonate, or alkyl sulfonates such as for example methane sulfonate or trifluoromethane sulfonate.

These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in Protective Groups in Organic Synthesis, 3rd edition, Wiley 1999). Specific examples are described in the subsequent paragraphs.

Intermediates of general formula (IV) are commercially available or are reported in the public domain, see the

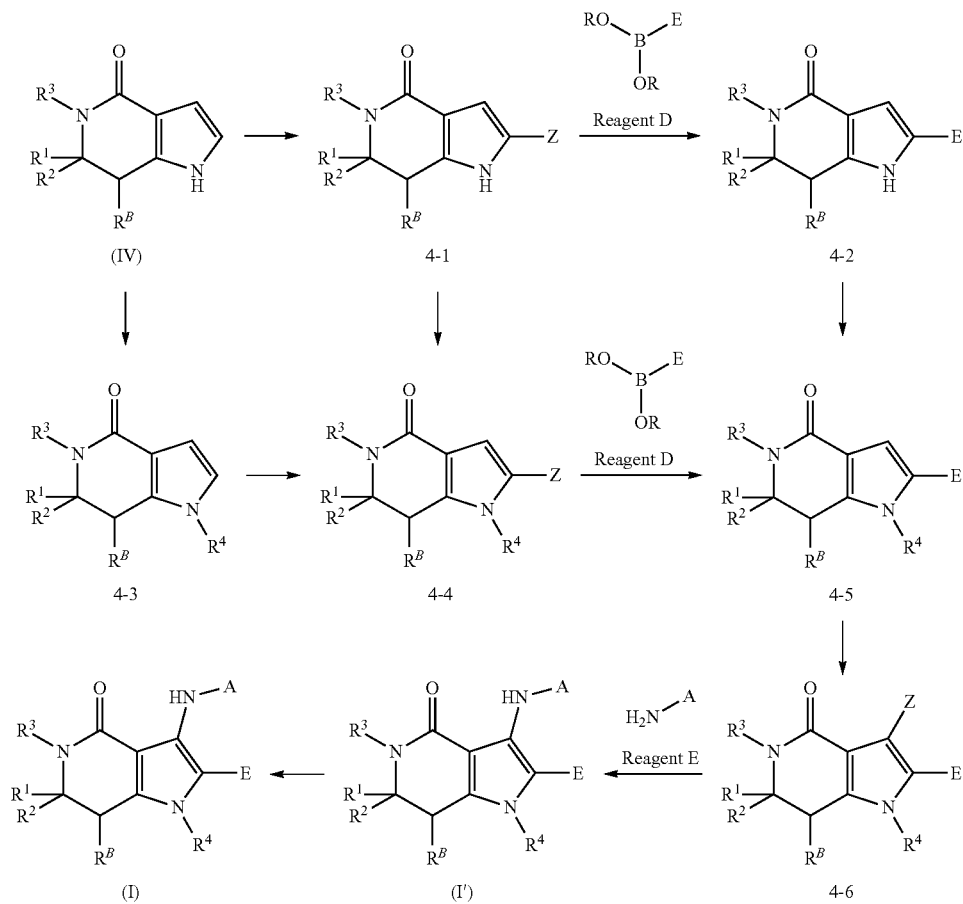

Scheme 4

Scheme 4: Route for the preparation of compounds of general formula (I), wherein $R^1$, $R^2$, $R^3$, $R^4$, $R^5$, $R^B$, A and E have the meaning as given for general formula (I), supra. In addition, interconversion of any of the substituents, $R^1$, $R^2$, $R^3$, $R^4$, $R^5$, $R^B$, A and E can be achieved before and/or after the exemplified transformation. The R in reagent D can be hydrogen to represent boronic acids or alkyl groups to represent boronic esters, optionally both R groups can be teachings of, for example, Menichincheri et al., WO2014/72220 A1; Clark et al., J. Heterocyclic Chem., 1993, 30, 829-831; Clark et al., J. Med. Chem., 1993, 36, 2645-2657; Schneller et al., J. Med. Chem., 1978, 21, 990-993.

Intermediates of general formula (IV) or intermediates of the formula 4-3 can be reacted to introduce a substituent Z, which is preferably a halide, such reactions are known to those skilled in the art (see Menichincheri et al., WO2014/

72220 A1 (introduction of bromide and iodide); Smith et al., Bioorg. Med. Chem. Lett., 2007, 17, 673-678 (introduction of bromide) Cee et al., WO2014/22752 A1 (introduction of bromide)) to furnish intermediates of the formula 4-1 from formula (IV) or intermediates of the formula 4-4 from formula 4-3.

Intermediates of general formula (IV) or intermediates of the formula 4-2 can be reacted to introduce the $R^4$ group, such as, for example, an alkyl group via alkylation under basic conditions (Marchionni et al., WO2009/40399 A1) or using the Mitsunobu reaction (US2007/142414 A1) or a tert-butoxycarbonyl (Boc) group (Kim et al., WO2013/62344 A1; Voss et al., WO2015/22073 A1) to furnish intermediates of the formula 4-3 from general formula (IV) or intermediates of the formula 4-4 from formula 4-1 or intermediates of the formula 4-5 from formula 4-2.

Intermediates of general formula 4-1 or intermediates of the formula 4-4 can be reacted to introduce the substituent E, such as, for example, an aryl or heteroaryl group using metal-catalyzed reactions, such as, for example, the Suzuki reaction. Such reactions are known to those skilled in the art (WO2007/39740 A2; Cee et al., WO2014/22752 A1; Smith et al., Bioorg. Med. Chem. Lett., 2007, 17, 673-678) and can be used to furnish intermediates of the formula 4-2 from general formula 4-1 or intermediates of the formula 4-5 from formula 4-4.

Intermediates of general formula (4-5) can be reacted with a suitable halogenating reagent, such as, for example, copper (I) bromide and N-bromosuccinimide, preferably N-bromosuccinimide, in a suitable solvent system, such as, for example, acetonitrile, in a temperature range from 0° C. to the boiling point of the respective solvent, preferably the reaction is carried out at room temperature, to furnish general formula (4-6). Similar examples for the bromination of pyrroles have been previously published using lactams (Aiello, E. et al., J. Heterocyclic Chem., 1982, 19, 977-979; Duranti, A. et al., Bioorg. Med. Chem., 2003, 11, 3965-3973).

Intermediates of general formula (4-6) can be reacted with a suitable primary amines, such as, for example, primary aromatic amines and primary amines, preferably primary aromatic amines, such as, for example aniline or 3-aminothiophene, in the presence of a base, such as, for example, lithium bis(trimethylsilyl)amide (LHMDS), in the presence of a catalyst, such as, for example a suitable ligand, preferably 2-(di-tert-butylphosphino)-2',4',6'-triisopropyl-3,6-dimethoxy-1,1-biphenyl (tBuBrettPhos) and in the presence of a pre-catalyst, such as, for example a palladium pre-catalyst, preferably chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct) in a suitable solvent system, such as, for example, tetrahydrofuran (THF), in a temperature range from 0° C. to the 200° C., preferably the reaction is carried out at 80° C., to furnish compounds of general formula (I').

Intermediates of general formula (I') are reacted with an alkylating agent which contain a suitable leaving group, such as, for example, Cl, Br, aryl sulfonates such as for example p-toluene sulfonate, or alkyl sulfonates such as for example methane sulfonate or trifluoromethane sulfonate, in the presence of a base, such as, for example sodium hydride, potassium carbonate, caesium carbonate, in a suitable solvent system, such as, for example, dimethylformamide, in a temperature range from 0° C. to the boiling point of the respective solvent, to furnish Intermediates of general formula (I).

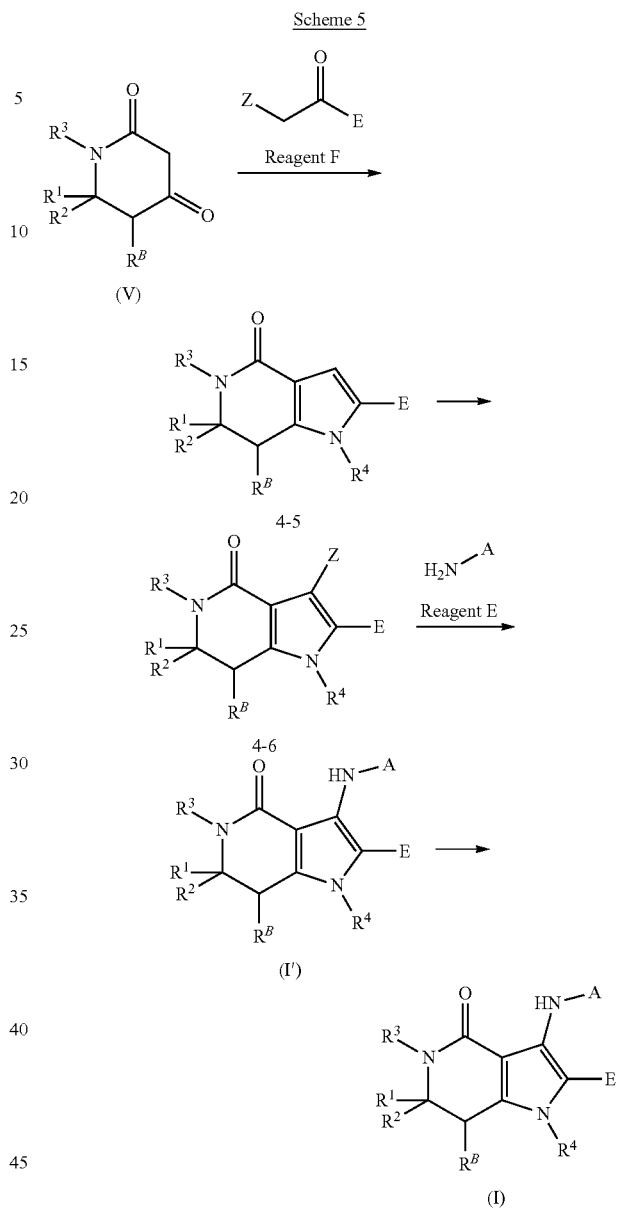

Scheme 5: Route for the preparation of compounds of general formula (I), wherein $R^1$, $R^2$, $R^3$, $R^4$, $R^5$, $R^B$, A and E have the meaning as given for general formula (I), supra. In addition, interconversion of any of the substituents, $R^1$, $R^2$, $R^3$, $R^4$, $R^5$, $R^B$, A and E can be achieved before and/or after the exemplified transformation. The substituent Z in intermediates of general formula 4-6 can be a suitable leaving group, such as, for example, Cl, Br, I, aryl sulfonates such as for example p-toluene sulfonate, or alkyl sulfonates such as for example methane sulfonate or trifluoromethane sulfonate. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Compounds of the formula (I) can also be prepared using the synthetic methods described in context of Scheme 3. Reagent E and reagent F are either commercially available or can be prepared according to procedures available from the public domain, as understandable to the person skilled in the art.

A suitably substituted 1,3-dicarbonyl of general formula (V) can be reacted with suitably substituted compounds of general formula (reagent F) where Z is a suitable leaving group, such as, for example, bromide, chloride, which in the presence of an ammonium salt, such as, for example, ammonium acetate can furnish intermediates of general formula (4-5). Similar examples for the formation of a pyrrole ring vl this manner have been previously published using lactams (Anderson, D. R. et al., J. Med. Chem., 2007, 50, 2647-2654; Amici, R. et al., J. Med. Chem., 2008, 51, 487-501; Bargiotti, A. et al., J. Med. Chem., 2009, 52, 293-307; Voss et al., WO 2015/022073 A1).

Intermediates of general formula (4-5) can be reacted with a suitable halogenating reagent, such as, for example, copper (I) bromide and N-bromosuccinimide, preferably N-bromosuccinimide, in a suitable solvent system, such as, for example, acetonitrile, in a temperature range from 0° C. to the boiling point of the respective solvent, preferably the reaction is carried out at room temperature, to furnish general formula (4-6). Similar examples for the bromination of pyrroles have been previously published using lactams (Aiello, E. et al., J. Heterocyclic Chem., 1982, 19, 977-979; Duranti, A. et al., Bioorg. Med. Chem., 2003, 11, 3965-3973).

Intermediates of general formula (4-6) can be reacted with a suitable primary amines, such as, for example, primary aromatic amines and primary amines, preferably primary aromatic amines, such as, for example aniline or 3-aminothiophene, in the presence of a base, such as, for example, lithium bis(trimethylsilyl)amide (LHMDS), in the presence of a catalyst, such as, for example a suitable ligand, preferably 2-(di-tert-butylphosphino)-2',4',6'-triisopropyl-3,6-dimethoxy-1,1-biphenyl (tBuBrettPhos) and in the presence of a pre-catalyst, such as, for example a palladium pre-catalyst, preferably chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct) in a suitable solvent system, such as, for example, tetrahydrofuran (THF), in a temperature range from 0° C. to the 200° C., preferably the reaction is carried out at 80° C., to furnish compounds of general formula (I').

Intermediates of general formula (I') are reacted with an alkylating agent which contain a suitable leaving group, such as, for example, Cl, Br, aryl sulfonates such as for example p-toluene sulfonate, or alkyl sulfonates such as for example methane sulfonate or trifluoromethane sulfonate, in the presence of a base, such as, for example sodium hydride, potassium carbonate, caesium carbonate, in a suitable solvent system, such as, for example, dimethylformamide, in a temperature range from 0° C. to the boiling point of the respective solvent, to furnish Intermediates of general formula (I).

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC may be applied. The compounds of the present invention which possess a sufficiently basic or acidic functionality, may result as a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of the compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, free acid, solvate, inclusion complex) of a compound of the present invention as isolated and described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis or by splitting up enantiomeric and diasteriomeric mixtures obtained in synthesis.

Enantiomeric and diastereomeric mixtures can be split up into the pure enantiomers and pure diastereomers by methods known to the person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids by formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-6 according to the examples as well as the intermediates used for their preparation.

Optionally, compounds of the formula (I) can be converted into their salts, or, optionally, salts of the compounds of the formula (I) can be converted into the free compounds. Corresponding processes are customary for the skilled person.

Commercial Utility

As mentioned supra, the compounds of the present invention have surprisingly been found to effectively inhibit Bub1 finally resulting in cell death e.g. apoptosis and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

A further aspect of the invention is the use of the compounds according to formula (I) for the treatment of cervical-, breast-, non-small cell lung-, prostate-, colon- and melanoma tumors and/or metastases thereof, especially preferred for the treatment thereof as well as a method of treatment of cervical-, breast-, non-small cell lung-, prostate-, colon- and melanoma tumors and/or metastases thereof comprising administering an effective amount of a compound of formula (I).

In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of cell death i.e apoptosis.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, especially the treatment, wherein the diseases are haematological tumours, solid tumours and/or metastases thereof.

Another aspect is the use of a compound of formula (I) for the prophylaxis and/or treatment of cervical-, breast-, non-small cell lung-, prostate-, colon- and melanoma tumors and/or metastases thereof, especially preferred for the treatment thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g. apoptosis. In an embodiment the disease is a haematological tumour, a solid tumour and/or metastases thereof. In another embodiment the disease is cervical-, breast-, non-small cell lung-, prostate-, colon- and melanoma tumor and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism.

A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death e.g. apoptosis of such cell types.

Preferably, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)—Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoa)l;

aerosol propellants (examples include but are not limited to carbon dioxide, $CCl_2F_2$, $F_2ClC—CClF_2$ and $CClF_3$)

air displacement agents—examples include but are not limited to nitrogen and argon;

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrilin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide); tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. Solution: A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilised Powder for i.v. Administration: A sterile preparation can be prepared with (i) 100-1000 mg of the desired compound of this invention as a lyophilised powder, (ii) 32-327 mg/ml sodium citrate, and (iii) 300-3000 mg Dextran 40. The formulation is reconstituted with sterile, injectable saline or dextrose 5% to a concentration of 10 to mg/ml, which is further diluted with saline or dextrose 5% to 0.2-0.4 mg/ml, and is administered either IV bolus or by IV infusion over 15-60 minutes.

Intramuscular suspension: The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL PART

The following table lists the abbreviations used in this paragraph and in the Intermediate Examples and Examples section as far as they are not explained within the text body.

| Abbreviation | Meaning |
|---|---|
| AcOH | acetic acid (ethanoic acid) |
| aq. | aqueous |
| Boc | t-butoxycarbonyl |
| BOP | (benzotriazol-1-yloxy)tris(dimethylamino)phosphonium hexafluorophosphate |
| br | broad |
| CI | chemical ionisation |
| $Cs_2CO_3$ | caesium carbonate |
| d | doublet |
| DAD | diode array detector |
| DBU | 1,8-diazabicyclo(5.4.0)undec-7-ene |
| DCC | N,N'-dicyclohexylcarbodiimide |
| DCM | dichloromethane |
| dd | double-doublet |
| DIC | N,N'-diisopropylcarbodiimide |
| DIPEA | diisopropylethylamine |
| DMA | Dimethylacetamide |
| DMF | N,N-dimethylformamide |
| DMSO | dimethyl sulfoxide |
| dt | double-triplet |
| EDC | 1-ethyl-3-(3-dimethylaminopropyl)carbodiimide |
| ELSD | Evaporative Light Scattering Detector |
| EtOAc | ethyl acetate |
| EtOH | ethanol |
| eq. | equivalent |
| ESI | electrospray (ES) ionisation |
| h | hour |
| HATU | 1-[bis(dimethylamino)methylene]-1H-1,2,3-triazolo[4,5-b]pyridinium 3-oxid hexafluorophosphate |
| HBTU | (o-benzotriazole-10yl)-N,N,N',N,-tetramethyluronium hexafluorophosphate |
| HCl | hydrochloric acid |
| HPLC | high performance liquid chromatography |
| $K_2CO_3$ | potassium carbonate |
| LC-MS | liquid chromatography mass spectrometry |
| m | multiplet |
| min | minute |
| MeCN | acetonitrile |
| MeOH | methanol |
| MS | mass spectrometry |
| NaCl | sodium chloride |
| $NaHCO_3$ | sodium hydrogen carbonate or sodium bicarbonate |
| NMR | nuclear magnetic resonance spectroscopy: chemical shifts (δ) are given in ppm. The chemical shifts were corrected by setting the DMSO signal to 2.50 ppm unless otherwise stated. |
| PDA | Photo Diode Array |
| Pd/C | palladium on activated charcoal |
| PyBOP | (benzotriazol-1-yloxy)tripyrrolidinophosphonium hexafluorophosphate |
| q | quartet |
| r.t. or rt or RT | room temperature |
| Rt | retention time (as measured either with HPLC or UPLC) in minutes |
| s | singlet |
| sat. | saturated |
| SIBX | stabilized 2-iodoxybenzoic acid |
| SM | starting material |
| SQD | Single-Quadrupole-Detector |
| T3P | propylphosphonic anhydride |
| t | triplet |
| td | triple-doublet |
| TEA | triethylamine |
| TFA | trifluoroacetic acid |
| THF | tetrahydrofuran |
| UPLC | ultra performance liquid chromatography |

Other abbreviations have their meanings customary per se to the skilled person.

The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered.

Reactions employing microwave irradiation may be run with a Biotage Initator® microwave oven optionally equipped with a robotic unit. The reported reaction times employing microwave heating are intended to be understood as fixed reaction times after reaching the indicated reaction temperature.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example pre-packed silica gel cartridges, e.g. from Separtis such as Isolute® Flash silica gel or Isolute® Flash $NH_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula and introduced into reaction vessels through rubber septa. Commercial grade reagents and solvents were used without further purification. The term "concentrated in vacuo" refers to the use of a Buchi rotary evaporator at a minimum pressure of approximately 15 mm of Hg. All temperatures are reported uncorrected in degrees Celsius (° c).

In order that this invention may be better understood, the following examples are set forth. These examples are for the purpose of illustration only, and are not to be construed as limiting the scope of the invention in any manner. All publications mentioned herein are incorporated by reference in their entirety.

Analytical LC-MS Conditions

LC-MS-data given in the subsequent specific experimental descriptions refer (unless otherwise noted) to the following conditions:

| | |
|---|---|
| System: | Waters Acquity UPLC-MS: Binary Solvent Manager, Sample Manager/Organizer, Column Manager, PDA, ELSD, SQD 3001 or ZQ4000 |
| Column: | Acquity UPLC BEH C18 1.7 50 × 2.1 mm |
| Solvent: | A1 = water + 0.1% vol. formic acid (99%) |
| | A2 = water + 0.2% vol. ammonia (32%) |
| | B1 = acetonitrile |
| Gradient: | 0-1.6 min 1-99% B, 1.6-2.0 min 99% B |
| Flow: | 0.8 ml/min |
| Temperature: | 60° C. |
| Injection: | 2.0 µl |
| Detection: | DAD scan range 210-400 nm -> Peaktable |
| | ELSD |
| Methods: | MS ESI+, ESI- Switch -> various scan ranges (Report Header) |
| | Method 1: A1 + B1 |
| | Method 2: A2 + B1 |

Preparative HPLC Conditions

"Purification by preparative HPLC" in the subsequent specific experimental descriptions refers to (unless otherwise noted) the following conditions:

Analytics (Pre- and Post Analytics: Method A):

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.1% vol. formic acid (99%) |
| | B = acetonitrile |
| Gradient: | 0-1.6 min 1-99% B, 1.6-2.0 min 99% B |
| Flow: | 0.8 ml/min |
| Temperature: | 60° C. |
| Injection: | 2.0 µl |
| Detection: | DAD scan range 210-400 nm |
| | MS ESI+, ESI-, scan range 160-1000 m/z |
| | ELSD |

Analytics (Pre- and Post Analytics: Method B):

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.2% vol. ammonia (32%) |
| | B = acetonitrile |
| Gradient: | 0-1.6 min 1-99% B, 1.6-2.0 min 99% B |
| Flow: | 0.8 ml/min |
| Temperature: | 60° C. |
| Injection: | 2.0 µl |
| Detection: | DAD scan range 210-400 nm |
| | MS ESI+, ESI-, scan range 160-1000 m/z |
| | ELSD |

Preparative HPLC (Method Acidic):

| | |
|---|---|
| System: | Waters Autopurificationsystem: Pump 2545, Sample Manager 2767, CFO, DAD 2996, ELSD 2424, SQD 3001 |
| Column: | XBridge C18 5 µm 100 × 30 mm |
| Solvent: | A = water + 0.1% vol. formic acid (99%) |
| | B = acetonitrile |
| Gradient: | 0-1 min 1% B, 1-8 min 1-99% B, 8-10 min 99% B |
| Flow: | 50 ml/min |
| Temperature: | RT |
| Solution: | max. 250 mg/2.5 ml dimethyl sufoxide or DMF |
| Injection: | 1 × 2.5 ml |
| Detection: | DAD scan range 210-400 nm |
| | MS ESI+, ESI-, scan range 160-1000 m/z |

Preparative HPLC (Method Basic):

| | |
|---|---|
| System: | Waters Autopurificationsystem: Pump 2545, Sample Manager 2767, CFO, DAD 2996, ELSD 2424, SQD 3001 |
| Column: | XBridge C18 5 µm 100 × 30 mm |
| Solvent: | A = water + 0.2% vol. ammonia (32%) |
| | B = acetonitrile |
| Gradient: | 0-1 min 1% B, 1-8 min 1-99% B, 8-10 min 99% B |
| Flow: | 50 ml/min |
| Temperature: | RT |
| Solution: | max. 250 mg/2.5 ml dimethyl sufoxide or DMF |
| Injection: | 1 × 2.5 ml |
| Detection: | DAD scan range 210-400 nm |
| | MS ESI+, ESI-, scan range 160-1000 m/z |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

EXAMPLES

Synthesis of Example 1

Intermediate 1-1-1 (4-hydroxy-6,6-dimethyl-2-oxo-N-phenyl-1,2,5,6-tetrahydropyridine-3-carbothioamide)

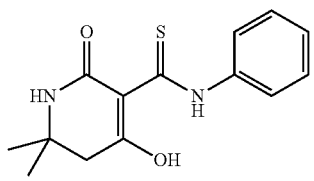 [SMILES: CC1(C)CC(O)=C(C(=S)Nc2ccccc2)C(=O)N1]

To a solution of 6,6-dimethyl-piperidin-2,4-dione (5 g, 35.4 mmol) and phenylisothiocyanate (4.79 g, 35.4 mmol) in MeCN (35 ml) cooled to 0° C. with an ice-bath was added slowly dropwise DBU (9 g, 8.8 mmol). The reaction was stirred for 16 h and then poured into ice-water containing conc. HCl (6 ml) and the resulting solid formed was collected and dried in vacuo at 90° C. The solid was recrystallized from EtOH to give the desired product (7.8 g, 80%).

Intermediate 1-2-1 (6,6-dimethyl-2-oxo-N-phenyl-4-[(pyridin-4-ylmethyl)amino]-1,2,5,6-tetrahydropyridine-3-carbothioamide)

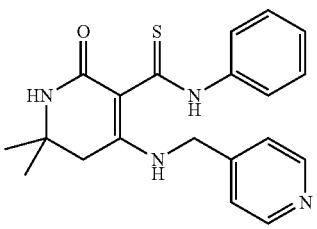 [SMILES: CC1(C)CC(NCc2ccncc2)=C(C(=S)Nc2ccccc2)C(=O)N1]

A solution of Intermediate 1-1-1 (13.14 g, 47.7 mmol) and 1-(pyridin-4-yl)methanamine in EtOH (40 ml) and EtOAc (40 ml) was heated at reflux for 60 h. On cooling, the product precipitated out and was collected by filtration (8 g, 46%).

$^1$H NMR (400 MHz, DMSO-d$_6$) δ ppm 1.15 (s, 6H), 2.69 (s, 2H), 4.77-4.83 (d, 2H), 7.16-7.22 (m, 1H), 7.31-7.40 (m, 4H), 7.42-7.49 (m, 2H), 7.64 (s, 1H), 8.56-8.60 (m, 2H), 14.02 (s, 1H), 14.96 (s, 1H)

Example 1 (6,6-dimethyl-3-(phenylamino)-2-(pyridin-4-yl)-1,5,6,7-tetrahydro-4H-pyrrolo[3,2-c]pyridin-4-one)

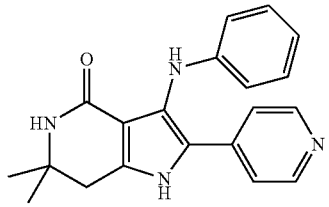 [SMILES: CC1(C)Cc2[nH]c(-c3ccncc3)c(Nc3ccccc3)c2C(=O)N1]

A mixture of Intermediate 1-2-1 (5.26 g, 14.4 mmol), hydrogen peroxide (34% in water, 2.5 ml, 28.7 mmol) in MeOH (20 ml) was heated at 100° C. for 4 h. Purification by silicagel chromatography (EtOAc:MeOH) gave the desired product (1.6 g, 32%).

$^1$H NMR (400 MHz, DMSO-d$_6$) δ ppm 1.28 (s, 6H), 2.86 (s, 2H), 6.62-6.76 (m, 3H), 7.09 (t, 2H), 7.19 (s, 1H), 7.55-7.61 (d, 2H), 7.68 (s, 1H), 8.40-8.47 (d, 2H), 12.11 (s, 1H).

Synthesis of Example 2

Intermediate 1-1-2

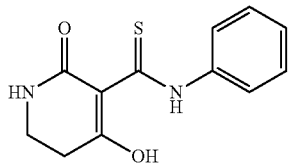 [SMILES: O=C1NCCC(O)=C1C(=S)Nc1ccccc1]

To a solution of piperidine-2,4-dione (5 g, 44 mmol) and phenylisothiocyanate (5.98 g, 44 mmol) in MeCN (40 ml) cooled to 0° C. with an ice-bath was added slowly dropwise DBU (11.24 g, 74 mmol). The reaction was stirred for 16 h and then poured into ice-water containing conc. HCl (6 ml) and the resulting solid formed was collected. The solid was purified using Biotage (SNAP silica 340 g (EtOAc:Hexane)) to give the desired product (1.75 g, 16%).

$^1$H NMR (400 MHz, DMSO-d$_6$) δ ppm 2.62 (t, 1 H) 2.76 (t, 1 H) 3.29 (td, 1 H) 3.42 (td, 1 H) 7.18-7.34 (m, 1 H) 7.34-7.56 (m, 4 H) 8.14 (br. s., 1 H) 14.58 (s, 1 H) 16.51 (br. s, 1 H)

Intermediate 1-2-2

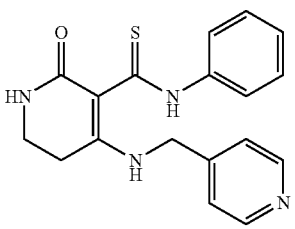 [SMILES: O=C1NCCC(NCc2ccncc2)=C1C(=S)Nc1ccccc1]

A solution of Intermediate 1-1-2 (1.7 g, 6.8 mmol) and 1-(pyridin-4-yl)methanamine (888 mg, 8.2 mmol) in EtOH (7.25 ml) and EtOAc (7.25 ml) was heated at reflux for 48 h. Concentrated and purified by silica chromatography (EtOAc:MeOH) to give the desired product (1.13 g, 49%).

$^1$H NMR (300 MHz, DMSO-d$_6$) δ ppm 2.65-2.77 (m, 2 H) 3.14 (dt, 2 H) 4.77 (d, 2 H) 7.14-7.26 (m, 1 H) 7.29-7.49 (m, 6 H) 7.70 (br. s., 1 H) 8.54-8.65 (m, 2 H) 13.77 (br. s., 1 H) 14.78 (s, 1 H)

Example 2 (3-(phenylamino)-2-(pyridin-4-yl)-1,5,6,7-tetrahydro-4H-pyrrolo[3,2-c]pyridin-4-one)

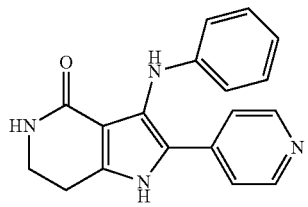 [SMILES: O=C1NCCc2[nH]c(-c3ccncc3)c(Nc3ccccc3)c21]

A mixture of Intermediate 1-2-2 (2.13 g, 6.8 mmol), hydrogen peroxide (34% in water, 3.47 ml, 34 mmol) in EtOH:DCM (2:1, 138 ml) was stirred at RT for 16 h. The solid was purified using Biotage (SNAP NH 28 g (EtOH:DCM)) to give the desired product (1.04 g, 50%).

$^1$H NMR (300 MHz, DMSO-d$_6$) δ ppm 2.85 (t, 2 H) 3.36-3.45 (m, 2 H) 6.53-6.68 (m, 3 H) 7.05 (t, 2 H) 7.13 (br. s., 1 H) 7.38 (s, 1 H) 7.40-7.49 (m, 2 H) 8.27-8.47 (m, 2 H) 11.78 (s, 1 H)

Synthesis of Example 3

Intermediate 1-2-3

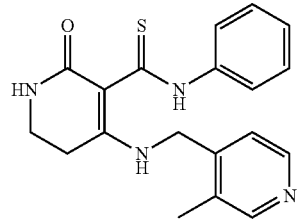 [SMILES: Cc1cnccc1CNC1=C(C(=S)Nc2ccccc2)C(=O)NCC1]

A solution of Intermediate 1-1-2 (450 mg, 1.8 mmol) and 1-(3-methylpyridin-4-yl)methanamine (310 mg, 2.5 mmol) in EtOH (2 ml) and EtOAc (2 ml) under Argon was heated in a sealed tube at 100° C. for 24 h. Another portion of 4-(methylamino)-3-methylpyridine (44 mg, 0.365 mmol) was added and the solution was heated at 100° C. for 16 h. The reaction was cooled and the solid collected by filtration and washed with EtOH, diethyl ether and hexane and dried in vacuo at 60° C. to give the desired product (258 mg, 40%).

$^1$H NMR (400 MHz, DMSO-d$_6$) δ ppm 2.28-2.34 (m, 3 H) 2.72 (t, 2 H) 3.15 (td, 2 H) 4.73 (d, 2 H) 7.15-7.22 (m, 1 H) 7.24 (d, 1 H) 7.32-7.40 (m, 2 H) 7.40-7.46 (m, 2 H) 7.70 (br. s., 1H) 8.39 (s, 1 H) 8.42 (d, 1 H) 13.72 (br. s., 1 H) 14.79 (s, 1 H)

Example 3 (2-(3-methylpyridin-4-yl)-3-(phenylamino)-1,5,6,7-tetrahydro-4H-pyrrolo[3,2-c]pyridin-4-one)

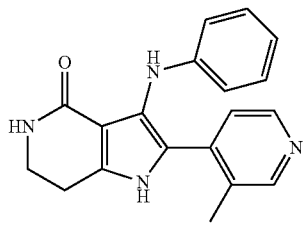 [SMILES: Cc1cnccc1-c1[nH]c2c(c1Nc1ccccc1)C(=O)NCC2]

A mixture of Intermediate 1-2-3 (123 mg, 0.35 mmol), hydrogen peroxide (34% in water, 71 µl, 0.7 mmol) in MeOH (1.3 ml) was stirred at 60° C. for 1 h. The reaction was quenched by the addition of sat. sodium thiosulfate (aq.). The organics were extracted with EtOAc and then concentrated. The solid was purified using Biotage (SNAP silica 2×25 g (MeOH:DCM)) to give the desired product (14 mg, 13%).

$^1$H NMR (300 MHz, DMSO-$d_6$) δ ppm 2.20 (s, 3 H) 2.82 (t, 2 H) 3.42 (td, 2 H) 6.39-6.55 (m, 3 H) 6.79-6.94 (m, 2 H) 7.06 (s, 1 H) 7.23 (d, 1 H) 7.34 (s, 1 H) 8.25-8.34 (m, 2 H) 11.30 (s, 1H)

Synthesis of Example 4

Example 4 (1-ethyl-6,6-dimethyl-3-(phenylamino)-2-(pyridin-4-yl)-1,5,6,7-tetrahydro-4H-pyrrolo[3,2-c]pyridin-4-one)

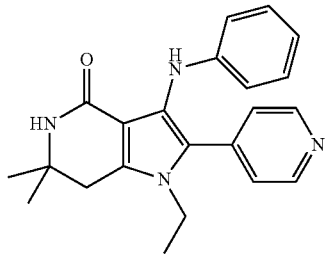 [SMILES: CCn1c2c(c(Nc3ccccc3)c1-c1ccncc1)C(=O)NC(C)(C)C2]

To a mixture of Example 1 (96 mg, 0.29 mmol), $K_2CO_3$ (135 mg, 0.87 mmol) in DMF (5 ml) at 0° C. was added iodoethane (120 mg, 0.87 mmol). The reaction was allowed to slowly warm to RT and stirred for 5 days. After 2 days an additional portion of iodoethane (24 mg, 0.15 mmol) was added. The reaction was diluted with water and extracted with EtOAc. The EtOAc layers were combined and washed with aqueous sat. NaCl solution and concentrated. Purification by Biotage (SNAP silica 25 g, (EtOAc:Hex) gave the desired product (14 mg, 13%).

$^1$H NMR (400 MHz, DMSO-$d_6$) δ ppm 1.11 (t, 3 H) 1.29 (s, 6 H) 2.52 (br. s., 2 H) 2.89 (s, 2 H) 3.99 (q, J2 H) 6.41-6.54 (m, 3 H) 6.86-6.96 (m, 2 H) 6.99 (s, 1 H) 7.12 (s, 1 H) 7.26-7.40 (m, 2 H) 8.38-8.46 (m, 2 H)

Synthesis of Example 5

Example 5 (1-ethyl-3-(phenylamino)-2-(pyridin-4-yl)-1,5,6,7-tetrahydro-4H-pyrrolo[3,2-c]pyridin-4-one)

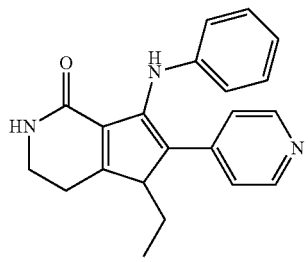 [SMILES: CCC1C2=C(C(=O)NCC2)C(Nc2ccccc2)=C1c1ccncc1]

To a mixture of Example 2 (450 mg, 1.5 mmol), $Cs_2CO_3$ (2.4 g, 7.4 mmol) in DMF (25 ml) at 0° C. was added iodoethane (692 mg, 4.4 mmol). The reaction was allowed to slowly warm to RT and stirred for 2 days. The reaction was diluted with water and extracted with EtOAc. The EtOAc layers were combined and washed with aqueous sat. NaCl solution and concentrated. Purification by Biotage (SNAP NH 28 g, (EtOH:DCM) gave the desired product (192 mg, 39%).

$^1$H NMR (400 MHz, DMSO-$d_6$) δ ppm 1.03-1.18 (t, 3 H) 2.90 (t, 2 H) 3.42 (td, 2 H) 4.00 (q, 2 H) 6.42-6.56 (m, 3 H) 6.85-6.96 (m, 2 H) 7.07 (br. s., 1 H) 7.11 (s, 1 H) 7.29-7.38 (m, 2 H) 8.34-8.59 (m, 2 H)

Synthesis of Example 6

Intermediate 1-1-3

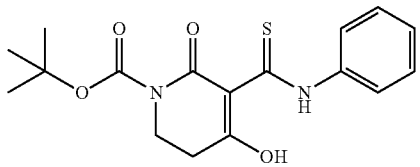 [SMILES: CC(C)(C)OC(=O)N1CCC(O)=C(C(=S)Nc2ccccc2)C1=O]

To a solution of N-tert-butoxycarbonyl-piperidine-2,4-dione (5 g, 23.4 mmol) and phenylisothiocyanate (3.33 g, 24.6 mmol) in MeCN (50 ml) cooled to −10° C. was added slowly dropwise DBU (5.36 g, 35.2 mmol). The reaction was stirred for 1 h at −10° C. and then at RT for 16 h. A precipitate formed and was collected by filtration and washed with MeCN and hexane. The solid was dissolved in diethyl ether:MeOH (95:5) and washed three times with half sat. $NH_4Cl$ (aq.), sat NaCl (aq.), filtered through a hydrophobic filter and concentrated to give the desired product (1.0 g, 11%).

$^1$H NMR (400 MHz, DMSO-$d_6$) δ ppm 1.42-1.54 (m, 9 H) 2.81 (t, 2 H) 3.77 (t, 2 H) 7.27-7.35 (m, 1 H) 7.40-7.50 (m, 2 H) 7.58 (d2 H) 12.82 (br. s., 1 H) 15.25 (br. s., 1 H)

Intermediate 1-2-4

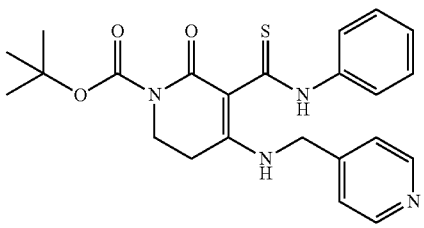 [SMILES: CC(C)(C)OC(=O)N1CCC(NCc2ccncc2)=C(C(=S)Nc2ccccc2)C1=O]

A solution of Intermediate 1-1-3 (1 g, 2.9 mmol) and 1-(pyridin-4-yl)methanamine (466 mg, 4.3 mmol) in EtOH (20 ml) and EtOAc (20 ml) under Argon was heated at reflux for 40 h. The reaction was filtered and diluted with DCM:MeOH (10:1), washed with half sat. $NH_4Cl$ (aq.) and concentrated. Purification by Biotage (SNAP silica 50 g, (EtOAc:Hex) gave the desired product (310 mg, 25%).

Example 6 (tert-butyl 4-oxo-3-(phenylamino)-2-(pyridin-4-yl)-1,4,6,7-tetrahydro-5H-pyrrolo[3,2-c]pyridine-5-carboxylate)

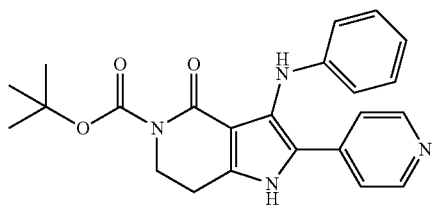 [SMILES: CC(C)(C)OC(=O)N1CCc2[nH]c(-c3ccncc3)c(Nc3ccccc3)c2C1=O]

A mixture of Intermediate 1-2-4 (300 mg, 0.68 mmol), hydrogen peroxide (34% in water, 349 μl, 3.4 mmol) in MeOH:DCM (1:2, 22.5 ml) was stirred at RT for 16 h. The reaction was quenched by the addition of sat. $NaHCO_3$ (aq.) and extracted with EtOAc. The organics were washed with sat. $NaHCO_3$ (aq.), sat. NaCl (aq.) and concentrated. The solid was purified using Biotage (SNAP silica 25 g (MeOH:DCM)) to give the desired product (30 mg, 11%).

$^1$H NMR (300 MHz, DMSO-$d_6$) δ ppm 1.44 (s, 9 H) 2.97 (t, 2 H) 3.96 (t, 2 H) 6.54-6.72 (m, 3 H) 7.05 (t, 2 H) 7.43 (s, 1 H) 7.47 (d2 H) 8.41 (d, 2 H) 12.01 (s, 1 H)

Synthesis of Example 7

Intermediate 1-1-4

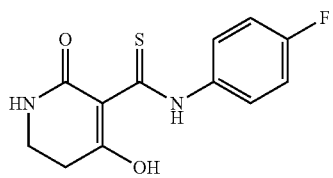 [SMILES: O=C1NCCC(O)=C1C(=S)Nc1ccc(F)cc1]

To a mixture of piperidine-2,4-dione (3.692 g, 32.6 mmol) and 4-fluorophenylisothiocyanate (5 g, 32.6 mmol) in MeCN (20 ml) was added TEA (231 mg, 0.32 mmol) and heated at reflux for 16 h. The reaction mixture was diluted with diethyl ether and washed three times with half sat. $NaHCO_3$ (aq.). The organics were passed through a 20 g SNAP silica cartridge and concentrated. The water layers were extracted with DCM:MeOH (10:1) and the organics were passed through a 10 g SNAP silica cartridge and combined with the other portion and concentrated. The solid was crystallized from EtOH twice to give the desired product (2.4 g, 28%).

$^1$H NMR (400 MHz, DMSO-$d_6$) δ ppm 2.61 (t, 1 H) 2.77 (t, 1 H) 3.22-3.31 (m, 1 H) 3.36-3.50 (m, 1 H) 6.83-7.01 (m, 1 H) 7.18-7.34 (m, 2 H) 7.37-7.51 (m, 2 H) 8.14 (br. s., 1H) 14.50 (s, 1 H)

Intermediate 1-2-5

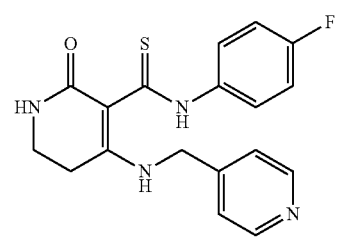 [SMILES: O=C1NCCC(NCc2ccncc2)=C1C(=S)Nc1ccc(F)cc1]

A solution of Intermediate 1-1-4 (0.8 g, 3.0 mmol) and 1-(pyridin-4-yl)methanamine (497 mg, 4.5 mmol) in EtOAc (40 ml) was heated at reflux with a trap containing molecular sieves (4 Å) for 16 h, allowed to cool and concentrated. Purification by Biotage (SNAP silica 50 g, (DCM:MeOH) gave a solid which was stirred with isopropanol. The solid was collected to give the desired product (470 mg, 44%).

$^1$H NMR (400 MHz, DMSO-$d_6$) δ ppm 2.67-2.77 (m, 2 H) 3.14 (td, 2 H) 4.77 (d2 H) 7.15-7.27 (m, 2 H) 7.30-7.38 (m, 2 H) 7.38-7.47 (m, 2 H) 7.69 (br. s., 1 H) 8.48-8.67 (m, 2 H) 13.73 (t, 1 H) 14.72 (s, 1 H)

Example 7 (3-[(4-fluorophenyl)amino]-2-(pyridin-4-yl)-1,5,6,7-tetrahydro-4H-pyrrolo[3,2-c]pyridin-4-one)

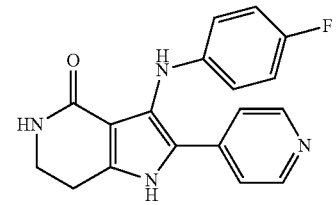 [SMILES: O=C1NCCc2[nH]c(-c3ccncc3)c(Nc3ccc(F)cc3)c21]

A mixture of Intermediate 1-2-5 (630 mg, 1.77 mmol), hydrogen peroxide (34% in water, 903 μl, 8.84 mmol) in MeOH:DCM (1:2, 30 ml) was stirred at RT for 60 h and then concentrated. The solid was purified using Biotage (SNAP NH 55 g (MeOH:DCM)) to give the desired product in a salt form. This solid was dissolved in EtOH and stirred with Amberlyst for 16 h, filtered and concentrated. Another Biotage purification (SNAP NH 28 g (MeOH:DCM)) gave the desired product (260 mg, 46%).

$^1$H NMR (300 MHz, DMSO-$d_6$) δ ppm 2.85 (t, 2 H) 3.40 (td, 2 H) 6.55-6.66 (m, 2 H) 6.83-6.93 (m, 2 H) 7.10 (s, 1 H) 7.31-7.38 (m, 1 H) 7.40-7.45 (m, 2 H) 8.31-8.41 (m, 2 H) 11.76 (br. s., 1 H)

Synthesis of Example 8

Intermediate 1-2-6

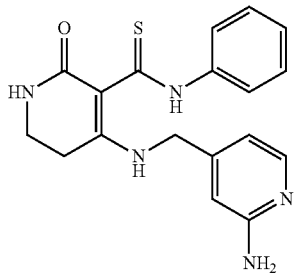 [SMILES: Nc1cc(CNC2=C(C(=S)Nc3ccccc3)C(=O)NCC2)ccn1]

A mixture of Intermediate 1-1-2 (1.35 g, 5.4 mmol) and (2-aminopyridin-4-yl)-methanamine (1.339 g, 10.9 mmol) in DMA (15.5 ml) was heated in a sealed tube at 120° C. for 90 min. The reaction was concentrated and purified using Biotage (SNAP silica 100 g (EtOH:DCM)) to give the desired product (778 mg, 40%).

$^1$H NMR (400 MHz, DMSO-$d_6$) δ ppm 2.68 (t, J=6.59 Hz, 2 H) 3.14 (td, 2 H) 4.56 (d, 2 H) 5.99 (s, 2 H) 6.34 (s, 1 H) 6.42 (dd1 H) 7.15-7.23 (m, 1 H) 7.31-7.41 (m, 2 H) 7.41-7.47 (m, 2 H) 7.68 (br. s., 1 H) 7.87 (d, 1 H) 13.64-13.80 (m, 1 H) 14.78 (s, 1 H)

Example 8 (2-(2-aminopyridin-4-yl)-3-(phenylamino)-1,5,6,7-tetrahydro-4H-pyrrolo[3,2-c]pyridin-4-one)

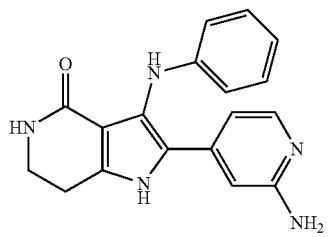 [SMILES: Nc1cc(-c2[nH]c3c(c2Nc2ccccc2)C(=O)NCC3)ccn1]

To a solution of Intermediate 1-2-6 (774 mg, 2.19 mmol) in DMA (45 ml) and TFA (250 mg, 2.19 mmol) under Argon was added palladium on charcoal (10%, 2.33 g, 2.19 mmol) and heated at 120° C. for 4 h. TEA (0.5 ml) was added and the mixture diluted with DCM and filtered. The solid was washed with DMA and DCM/MeOH. The filtrate was concentrated. Purification using Biotage (SNAP NH 28 g (EtOH:DCM)) gave the desired product (230 mg, 33%).

$^1$H NMR (400 MHz, DMSO-$d_6$) δ ppm 2.81 (t, 2 H) 3.34-3.42 (m, 2 H) 5.63 (s, 2 H) 6.53-6.65 (m, 4H) 6.68 (dd, 1 H) 6.97-7.08 (m, 3 H) 7.17 (s, 1 H) 7.73 (d, 1 H) 11.52 (s, 1 H)

Synthesis of Example 9

Example 9 (1-(2-methoxyethyl)-3-(phenylamino)-2-(pyridin-4-yl)-1,5,6,7-tetrahydro-4H-pyrrolo[3,2-c]pyridin-4-one)

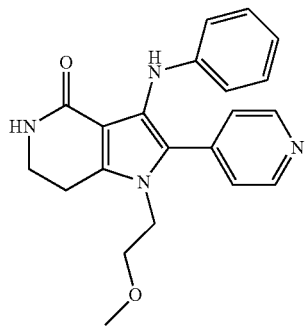 [SMILES: COCCn1c2c(c(Nc3ccccc3)c1-c1ccncc1)C(=O)NCC2]

To a mixture of Example 2 (100 mg, 0.33 mmol), $K_2CO_3$ (454 mg, 3.3 mmol) in DMF (6 ml) at 0° C. was added 2-chloroethyl methyl ether (15 5 mg, 1.6 mmol). The reaction was allowed to slowly warm to RT and stirred for 16 h. The reaction was then heated at 100° C. for 1 h. Additional 2-chloroethyl methyl ether (78 mg, 0.8 mmol) and $K_2CO_3$ (227 mg, 1.6 mmol) were added and the reaction was heated using a microwave at 120° C. for 2 h. The reaction was allowed to cool, diluted with water and extracted with EtOAc. The EtOAc layers were combined and washed with aqueous sat. NaCl solution and concentrated. Purification by Biotage (SNAP silica 10 g, (EtOH:DCM) gave the desired product (21 mg, 18%).

$^1$H NMR (400 MHz, DMSO-$d_6$) δ ppm 2.90 (t, 2 H) 3.11 (s, 3 H) 3.33-3.46 (m, 4 H) 4.15 (t, 2 H) 6.44-6.56 (m, 3 H) 6.86-6.96 (m, 2 H) 7.06 (s, 1 H) 7.10 (s, 1 H) 7.31-7.40 (m, 2 H) 8.39-8.60 (m, 2 H) Synthesis of Example 10

Example 10 (2-methyl-N-{4-[5-(2-methylpropanoyl)-4-oxo-3-(phenylamino)-4,5,6,7-tetrahydro-1H-pyrrolo[3,2-c]pyridin-2-yl]pyridin-2-yl}propanamide)

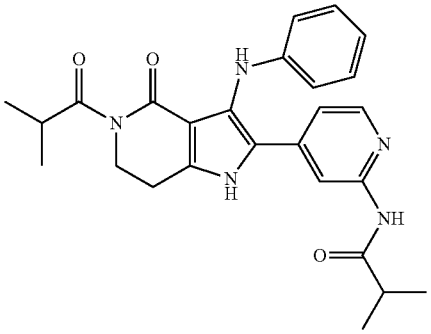 [SMILES: CC(C)C(=O)Nc1cc(-c2[nH]c3c(c2Nc2ccccc2)C(=O)N(C(=O)C(C)C)CC3)ccn1]

To a solution of Example 8 (37 mg, 0.12 mmol) and pyridine (161 μl, 1.16 mmol) in THF (3.3 ml) at RT was added isopropionyl chloride (62 mg, 0.58 mmol) and the solution stirred for 30 min. Another portion of isopropionyl chloride (44 mg, 0.56 mmol) was added and the solution stirred for 16 h at RT. The reaction was quenched by the addition of MeOH and toluene and concentrated. Purification by preparative TLC (silica, (MeOH:DCM) gave the desired product (3 mg, 5%).

$^1$H NMR (300 MHz, DMSO-$d_6$) δ ppm 1.07 (dd, 12 H) 2.74 (m, 1 H) 2.93 (t, 2 H) 3.53 (m, 1 H) 4.07 (t, 2 H) 6.55-6.65 (m, 3 H) 6.99-7.06 (m, 2 H) 7.19 (dd, 1 H) 7.39 (s, 1 H) 8.08 (d, 1H) 8.26-8.32 (m, 1 H) 10.29 (s, 1 H) 12.13 (br. s., 1 H)

Synthesis of Example 11

Example 11 (1-ethyl-3-[(4-fluorophenyl)amino]-2-(pyridin-4-yl)-1,5,6,7-tetrahydro-4H-pyrrolo[3,2-c]pyridin-4-one)

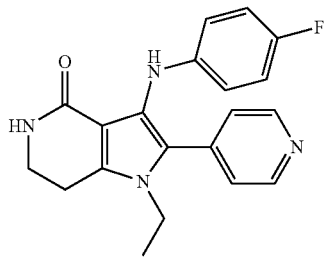 [SMILES: CCn1c2c(c(Nc3ccc(F)cc3)c1-c1ccncc1)C(=O)NCC2]

To a mixture of Example 7 (260 mg, 0.8 mmol), K$_2$CO$_3$ (669 mg, 4.8 mmol) in DMF (10 ml) was added iodoethane (503 mg, 3.2 mmol) and stirred at RT for 16 h. The reaction was concentrated, water was added and the mixture extracted with DCM:MeOH (100:1). The organic layers were combined and concentrated. Purification by Biotage (SNAP NH 28 g, (MeOH:DCM) followed by a Biotage (SNAP silica 25 g, (MeOH:DCM)) gave the desired product (80 mg, 28%).

$^1$H NMR (400 MHz, DMSO-$d_6$) δ ppm 1.11 (t, 3 H) 2.90 (t, 2 H) 3.42 (td, 2 H) 3.99 (q, 2 H) 6.41-6.59 (m, 2 H) 6.70-6.84 (m, 2 H) 7.00-7.16 (m, 2 H) 7.25-7.39 (m, 2 H) 8.44-8.63 (m, 2 H)

Synthesis of Example 12

Intermediate 1-2-7

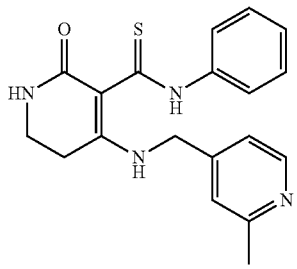 [SMILES: Cc1cc(CNC2=C(C(=S)Nc3ccccc3)C(=O)NCC2)ccn1]

A solution of Intermediate 1-1-2 (500 mg, 2 mmol) and 1-(2-methylpyridin-4-yl)methanamine (1.13 g, 9.1 mmol) in EtOAc (50 ml) under Argon was heated at reflux for 5 days. The reaction was cooled and concentrated. Purification by Biotage (SNAP silica 50 g, (MeOH:DCM) gave the desired product (380 mg, 53%).

$^1$H NMR (400 MHz, DMSO-$d_6$) δ ppm 2.46 (s, 3 H) 2.65-2.74 (m, 2 H) 3.13 (td, 2 H) 4.71 (d, 2 H) 7.10-7.22 (m, 2 H) 7.31-7.39 (m, 2 H) 7.39-7.45 (m, 2 H) 7.67 (br. s., 1 H) 8.25-8.39 (m, 1 H) 8.42 (d, 1 H) 13.75 (br. s., 1 H) 14.77 (s, 1 H)

Example 12 (2-(2-methylpyridin-4-yl)-3-(phenylamino)-1,5,6,7-tetrahydro-4H-pyrrolo[3,2-c]pyridin-4-one)

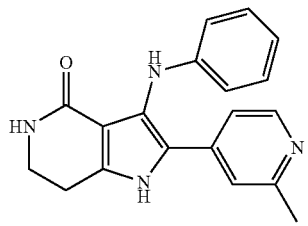 [SMILES: Cc1cc(-c2[nH]c3c(c2Nc2ccccc2)C(=O)NCC3)ccn1]

A mixture of Intermediate 1-2-7 (375 mg, 1.06 mmol), hydrogen peroxide (34% in water, 543 μl, 5.32 mmol) in MeOH:DCM (1:2, 21 ml) was stirred at RT for 16 h. The reaction was diluted with EtOAc and washed with sat. NaHCO$_3$ (aq.) and then concentrated. The solid was stirred with EtOH:DCM and filtered to give the desired product (120 mg, 35%).

$^1$H NMR (300 MHz, DMSO-$d_6$) δ ppm 2.32 (s, 3 H) 2.85 (t, 2 H) 3.36-3.45 (m, 2 H) 6.59 (d, 2 H) 6.64 (t, 1 H) 7.05 (dd, 2 H) 7.09 (s, 1 H) 7.24 (dd, 1 H) 7.32 (s, 1 H) 7.36 (s, 1 H) 8.22 (d, 1 H) 11.71 (s, 1 H)

Synthesis of Example 13

Example 13 (1-ethyl-2-(2-methylpyridin-4-yl)-3-(phenylamino)-1,5,6,7-tetrahydro-4H-pyrrolo[3,2-c]pyridin-4-one)

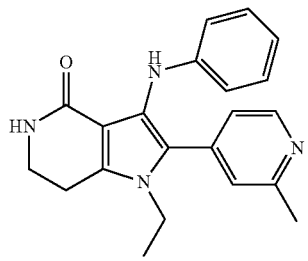 [SMILES: CCn1c2c(c(Nc3ccccc3)c1-c1ccnc(C)c1)C(=O)NCC2]

To a mixture of Example 12 (75 mg, 0.24 mmol), Cs$_2$CO$_3$ (384 mg, 1.18 mmol) in DMF (4 ml) at 0° C. was added iodoethane (110 mg, 0.71 mmol). The reaction was allowed to slowly warm to RT and stirred for 16 h. Purification by Biotage (SNAP silica 10 g, (MeOH:DCM) gave the desired product (28 mg, 34%).

$^1$H NMR (300 MHz, DMSO-$d_6$) δ ppm 1.02-1.15 (m, 3 H) 2.34-2.42 (m, 3 H) 2.89 (t, 2 H) 3.41 (td, 2 H) 3.90-4.10 (m, 2 H) 6.36-6.56 (m, 3 H) 6.91 (t, 2 H) 7.00-7.09 (m, 2 H) 7.13 (d, 1 H) 7.18 (s, 1 H) 8.35 (d, 1 H)

Synthesis of Example 14

Example 14 (N-{4-[4-oxo-3-(phenylamino)-4,5,6,7-tetrahydro-1H-pyrrolo[3,2-c]pyridin-2-yl]pyridin-2-yl}acetamide)

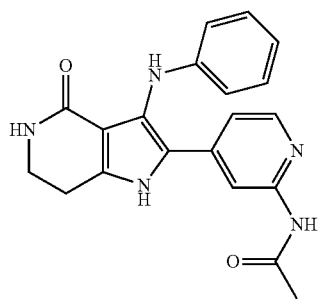 [SMILES: CC(=O)Nc1cc(-c2[nH]c3c(c2Nc2ccccc2)C(=O)NCC3)ccn1]

To a solution of Example 8 (150 mg, 0.47 mmol) in pyridine (10 ml) at 0° C. was added acetyl chloride (44 mg, 0.56 mmol) and the solution stirred for 30 min. Another portion of acetyl chloride (44 mg, 0.56 mmol) was added and the solution stirred for 1 h at 0° C. Another portion of acetyl chloride (44 mg, 0.56 mmol) was added and the solution stirred for 1 h at 0° C. Another portion of acetyl chloride (44 mg, 0.56 mmol) was added and the solution stirred for 1 h at 0° C. Another portion of acetyl chloride (88 mg, 1.1 mmol) was added and the solution stirred for 1 h at RT. Another portion of acetyl chloride (88 mg, 1.1 mmol) was added and the solution stirred for 1 h at RT. The reaction was diluted with DCM:MeOH and washed with half sat. NaHCO$_3$ (aq.) and concentrated. Purification by Biotage (SNAP silica 10 g, (MeOH:DCM) followed by another Biotage purification (SNAP NH 28 g, (MeOH:DCM)) gave the desired product (100 mg, 59%).

$^1$H NMR (300 MHz, DMSO-d$_6$) δ ppm 2.01-2.13 (m, 3 H) 2.78-2.88 (m, 2 H) 3.34-3.45 (m, 2 H) 6.53-6.65 (m, 3 H) 7.02 (t, 2 H) 7.06-7.15 (m, 2 H) 7.30 (s, 1 H) 8.03 (d1 H) 8.19 (s, 1 H) 10.29 (s, 1 H) 11.75 (s, 1 H)

Synthesis of Example 15

Example 15 (N-{4-[1-ethyl-4-oxo-3-(phenylamino)-4,5,6,7-tetrahydro-1H-pyrrolo[3,2-c]pyridin-2-yl]pyridin-2-yl}acetamide)

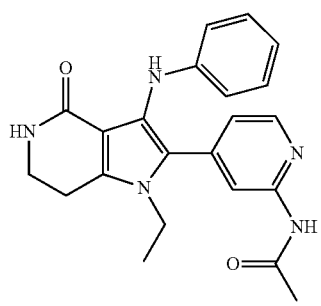 [SMILES: CCn1c2c(c(Nc3ccccc3)c1-c1ccnc(NC(C)=O)c1)C(=O)NCC2]

To a mixture of Example 14 (85 mg, 0.24 mmol), Cs$_2$CO$_3$ (307 mg, 0.94 mmol) in DMF (3 ml) at RT was added iodoethane (55 mg, 0.35 mmol) and the mixture stirred at RT for 1 h. Another portion of iodoethane (28 mg, 0.18 mmol) was added and the mixture stirred at RT for 1 h. The reaction was diluted with water and extracted with DCM:MeOH (100:1). The organic layers were combined, concentrated and purified by Biotage (SNAP NH 28 g, (MeOH:DCM)). The isolated solid was stirred in hot EtOH and filtered to give the desired product (60 mg, 66%).

$^1$H NMR (400 MHz, DMSO-d$_6$) δ ppm 1.18 (t, 3 H) 2.08 (s, 3 H) 2.90 (t, 2 H) 3.43 (td, 2 H) 4.00 (q, 2 H) 6.44-6.56 (m, 3 H) 6.88-6.96 (m, 2 H) 7.01 (dd, 1 H) 7.05 (br. s., 1 H) 7.08 (s, 1 H) 8.10 (s, 1 H) 8.15 (d, 1 H) 10.45 (s, 1 H)

Synthesis of Example 16

Intermediate 1-2-8

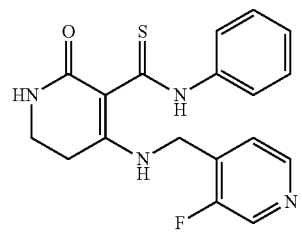 [SMILES: O=C1NCCC(NCc2ccncc2F)=C1C(=S)Nc1ccccc1]

A mixture of Intermediate 1-1-2 (200 mg, 0.8 mmol) and 3-fluoropyridin-4-ylmethanamine (203 mg, 1.6 mmol) in DMA (2.5 ml) was heated in a sealed tube at 120° C. for 90 min. The reaction was concentrated and purified using Biotage (SNAP silica 25 g (EtOH:DCM)) to give the desired product (124 mg, 43%).

$^1$H NMR (400 MHz, DMSO-d$_6$) δ ppm 2.74 (t, 2 H) 3.12-3.19 (m, 2 H) 4.84 (d, 2 H) 7.15-7.22 (m, 1 H) 7.32-7.40 (m, 2 H) 7.40-7.48 (m, 3 H) 7.72 (br. s., 1 H) 8.47 (dd, 1 H) 8.58 (d, 1H) 13.64-13.84 (m, 1 H) 14.77 (s, 1 H)

Example 16 (2-(3-fluoropyridin-4-yl)-3-(phenylamino)-1,5-dihydro-4H-pyrrolo[3,2-c]pyridin-4-one)

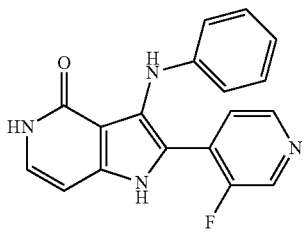 [SMILES: O=c1[nH]ccc2[nH]c(-c3ccncc3F)c(Nc3ccccc3)c12]

To a solution of Intermediate 1-2-8 (121 mg, 0.34 mmol) in DMA (7 ml) in a sealed tube under Argon was added TFA (26.1 µl, 38.7 mg, 0.34 mmol) followed by 10% Pd/C (361 mg, 0.34 mmol). The reaction was heated at 120° C. for 5 h. The reaction was allowed to cool, diluted with DCM and filtered. The catalyst was washed with MeOH:DCM and the organics were concentrated. Purification by Biotage (SNAP NH 11 g, (EtOH:DCM)), followed by preparative TLC (silicagel, 20×20 cm, MeOH:DCM 5:95) gave the desired product (10 mg, 9%).

$^1$H NMR (400 MHz, DMSO-d$_6$) δ ppm 6.43 (d, 1 H) 6.54-6.63 (m, 3 H) 6.95-7.09 (m, 3 H) 7.47-7.64 (m, 2 H) 8.19-8.30 (m, 1 H) 8.55 (d, 1 H) 10.79 (d, 1 H) 11.59 (br. s., 1 H)

Synthesis of Example 17

Intermediate 1-2-9

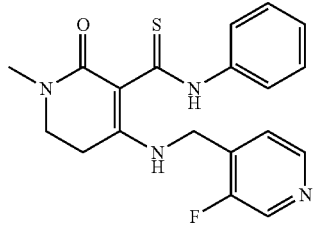 [SMILES: CN1CCC(NCc2ccncc2F)=C(C(=S)Nc2ccccc2)C1=O]

A solution of Intermediate 1-1-5 (250 mg, 0.95 mmol) and (3-fluoropyridin-4-yl)methanamine (240 mg, 1.91 mmol) in DMA (2.5 ml) was heated using a microwave at 130° C. for 30 mins. The mixture was filtered and purified by preparative HPLC (basic method) to give the desired product (126 mg, 34%).

$^1$H NMR (400 MHz, DMSO-d$_6$) δ ppm 2.79 (t, 2 H) 2.94 (s, 3 H) 3.31-3.35 (m, 2 H) 4.84 (d, 2 H) 7.14-7.24 (m, 1 H) 7.33-7.40 (m, 2 H) 7.40-7.48 (m, 3 H) 8.47 (m, 1 H) 8.58 (d, 1 H) 13.59 (br. s., 1 H) 14.68 (s, 1 H)

Example 17 (2-(3-fluoropyridin-4-yl)-5-methyl-3-(phenylamino)-1,5,6,7-tetrahydro-4H-pyrrolo[3,2-c]pyridin-4-one))

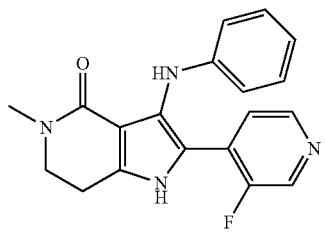 [SMILES: CN1CCc2[nH]c(-c3ccncc3F)c(Nc3ccccc3)c2C1=O]

A mixture of Intermediate 1-2-9 (124 mg, 0.34 mmol), hydrogen peroxide (34% in water, 60.5 μl, 0.67 mmol) in EtOH (5 ml) was heated at 90° C. for 2 h. Purification by preparative HPLC (basic method) gave the desired product (50 mg, 44%).

$^1$H NMR (400 MHz, DMSO-d$_6$) δ ppm 2.84-2.91 (m, 3 H) 2.95 (t, 2 H) 3.56 (t, 2 H) 6.56 (d, 2 H) 6.61 (t, 1 H) 7.00 (m, 2 H) 7.40 (m, m 1 H) 7.54 (s, 1 H) 8.18 (m, 1 H) 8.48 (d, 1 H) 11.43 (s, 1 H)

Synthesis of Example 18

Example 18 (2-(3-fluoropyridin-4-yl)-3-(phenylamino)-1,5,6,7-tetrahydro-4H-pyrrolo[3,2-c]pyridin-4-one)

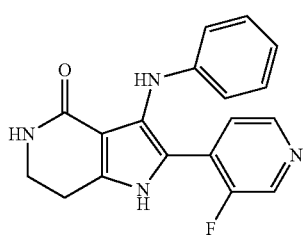 [SMILES: O=C1NCCc2[nH]c(-c3ccncc3F)c(Nc3ccccc3)c21]

To a solution of Intermediate 1-2-9 (121 mg, 0.34 mmol) in DMA (7 ml) in a sealed tube under Argon was added TFA (26.1 μl, 38.7 mg, 0.34 mmol) followed by 10% Pd/C (361 mg, 0.34 mmol). The reaction was heated at 120° C. for 5 h. The reaction was allowed to cool, diluted with DCM and filtered. The catalyst was washed with MeOH:DCM and the organics were concentrated. Purification by Biotage (SNAP NH 11 g, (EtOH:DCM)), followed by preparative TLC (silicagel, 20×20 cm, MeOH:DCM 5:95) gave the desired product (16 mg, 13%).

$^1$H NMR (400 MHz, DMSO-d$_6$) δ ppm 2.86 (t, 2 H) 3.40 (td, 2 H) 6.50-6.65 (m, 3 H) 7.00 (t, 2 H) 7.14 (br. s., 1 H) 7.40 (dd, 1 H) 7.45-7.52 (m, 1 H) 8.18 (d, 1 H) 8.48 (d, 1 H) 11.45 (br. s., 1 H)

Synthesis of Example 19

Example 19 (1-ethyl-3-{4-[4-oxo-3-(phenylamino)-4,5,6,7-tetrahydro-1H-pyrrolo[3,2-c]pyridin-2-yl]pyridin-2-yl}urea)

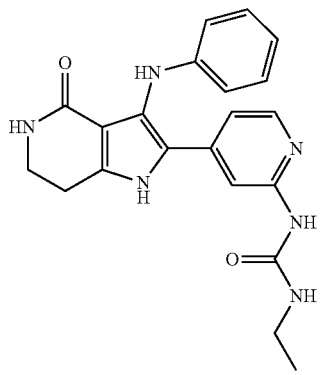 [SMILES: CCNC(=O)Nc1cc(-c2[nH]c3c(c2Nc2ccccc2)C(=O)NCC3)ccn1]

To a solution of Example 8 (45 mg, 141 μmol) in pyridine (1 ml) was added ethyl isocyanate (30 mg, 423 μmol). The mixture was stirred at RT for 16 h and concentrated. Purification by preparative HPLC (basic method) gave the desired product (30 mg, 51%).

$^1$H NMR (400 MHz, DMSO-d$_6$) δ ppm 1.07 (t, 3 H) 2.83 (t, 2 H) 3.09-3.22 (m, 2 H) 3.39 (td, 2 H) 5.76 (s, 1 H) 6.53-6.59 (m, 2 H) 6.62 (t, 1 H) 6.97-7.06 (m, 3 H) 7.08 (s, 1 H) 7.27 (s, 1 H) 7.42 (s, 1 H) 7.94 (d, 1 H) 8.10 (br. s., 1 H) 9.02 (s, 1 H) 11.69 (br. s., 1 H)

Synthesis of Example 20

Intermediate 1-1-5

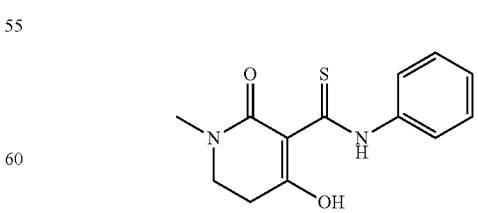

To an ice-cooled mixture of N-methyl-piperidine-2,4-dione (1.408 mg, 11.1 mmol) and phenylisothiocyanate (1.497 g, 11.1 mmol) in MeCN (15 ml) was added DBU (2.697 g, 17.7 mmol) slowly dropwise and the mixture stirred for 16 h. The reaction was poured into ice-water containing concentrated HCl (2.6 ml). The mixture was extracted with EtOAc. The organic layers were washed with sat. NaCl, filtered through a hydrophobic filter and concentrated. Purification using Biotage (SNAP silica 340 g (EtOAc:Hexane)) gave the desired product (1.68 g, 55%).

¹H NMR (400 MHz, DMSO-$d_6$) δ ppm 2.82 (t, 2 H) 2.96 (s, 3 H) 3.47 (t, 2 H) 7.22-7.35 (m, 1 H) 7.36-7.51 (m, 4 H) 14.57 (br. s., 1 H) 16.48 (br. s., 1 H)

Intermediate 1-2-10

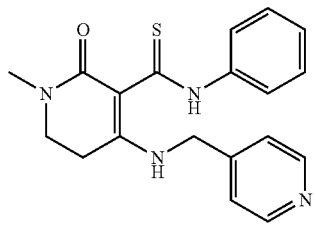 [SMILES: CN1CCC(NCc2ccncc2)=C(C(=S)Nc2ccccc2)C1=O]

A solution of Intermediate 1-1-5 (860 mg, 3.3 mmol) and 1-(pyridin-4-yl)methanamine (709 mg, 6.6 mmol) in EtOH (25 ml) and EtOAc (25 ml) was heated at reflux with a trap containing molecular sieves (4 Å) for 16 h. The mixture was allowed to cool, concentrated and purified by preparative HPLC (Method: Waters XBridge C18 5µ 100×30 mm; Solvent A: water+0.2% Vol. ammonium hydroxide (32%), Solvent B: Acetonitrile; Gradient: 0.00-0.50 min 20% B (25 to 70 ml/min), 0.51-5.50 min 20-80% B; Flow: 70 ml/min) to give the desired product (322 mg, 28%).

¹H NMR (400 MHz, DMSO-$d_6$) δ ppm 2.75 (t, 2 H) 2.93 (s, 3 H) 3.32-3.37 (m, 2 H) 4.77 (d, 2 H) 7.16-7.22 (m, 1 H) 7.32-7.39 (m, 4 H) 7.41-7.47 (m, 2 H) 8.50-8.64 (m, 2 H) 13.66 (br. s., 1 H) 14.68 (s, 1 H)

Example 20 (5-methyl-3-(phenylamino)-2-(pyridin-4-yl)-1,5,6,7-tetrahydro-4H-pyrrolo[3,2-c]pyridin-4-one)

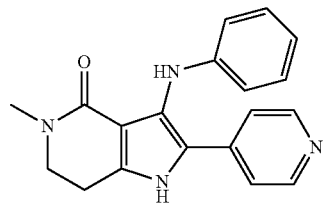 [SMILES: CN1CCc2[nH]c(-c3ccncc3)c(Nc3ccccc3)c2C1=O]

A mixture of Intermediate 1-2-10 (17 mg, 48 µmol), hydrogen peroxide (34% in water, 9 µl, 96 µmol) in EtOH (1 ml) was heated in a sealed tube at 80° C. for 1 h. Purification by preparative HPLC (basic method) gave the desired product (9 mg, 58%).

¹H NMR (400 MHz, DMSO-$d_6$) δ ppm 2.87 (s, 3 H) 2.95 (t, 2 H) 3.55 (t, 2 H) 6.54-6.68 (m, 3 H) 7.05 (dd, 2 H) 7.38-7.46 (m, 3 H) 8.33-8.41 (m, 2 H) 11.76 (br. s., 1 H)

Synthesis of Example 21

Intermediate 1-2-11

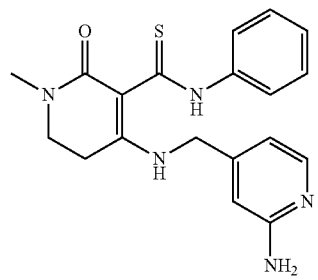 [SMILES: CN1CCC(NCc2ccnc(N)c2)=C(C(=S)Nc2ccccc2)C1=O]

A solution of Intermediate 1-1-5 (860 mg, 3.3 mmol) and 4-(aminomethyl)pyridin-2-amine (807 mg, 6.6 mmol) in EtOH (25 ml) and EtOAc (25 ml) was heated at reflux with a trap containing molecular sieves (4 Å) for 16 h. The mixture was allowed to cool, concentrated and purified by preparative HPLC (Method: Waters XBridge C18 5µ 100× 30 mm; Solvent A: Water+0.2% Vol. Ammonium hydroxide (32%), Solvent B: Acetonitrile; Gradient: 0.00-0.50 min 27% B (25 to 70 ml/min), 0.51-5.50 min 27-77% B; Flow: 70 ml/min) to give the desired product (230 mg, 19%).

¹H NMR (400 MHz, DMSO-$d_6$) δ ppm 2.74 (t, 2 H) 2.94 (s, 3 H) 3.27-3.38 (m, 2 H) 4.56 (d, 2 H) 5.98 (s, 2 H) 6.34 (s, 1 H) 6.41 (dd, 1 H) 7.15-7.22 (m, 1 H) 7.32-7.39 (m, 2 H) 7.41-7.46 (m, 2 H) 7.87 (d, 1 H) 13.63 (br. s., 1 H) 14.69 (s, 1 H)

Example 21 (2-(2-aminopyridin-4-yl)-5-methyl-3-(phenylamino)-1,5,6,7-tetrahydro-4H-pyrrolo[3,2-c]pyridin-4-one)

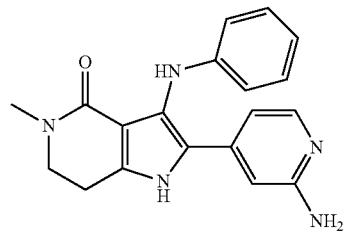 [SMILES: CN1CCc2[nH]c(-c3ccnc(N)c3)c(Nc3ccccc3)c2C1=O]

A mixture of Intermediate 1-2-11 (11 mg, 30 µmol), hydrogen peroxide (34% in water, 5 µl, 60 µmol) in EtOH (1 ml) was heated in a sealed tube at 80° C. for 1 h. Purification by preparative HPLC (basic method) gave the desired product (5 mg, 51%).

¹H NMR (400 MHz, DMSO-$d_6$) δ ppm 2.85 (s, 3H) 2.90 (t, 2 H) 3.53 (t, 2 H) 5.64 (s, 2 H) 6.53-6.59 (m, 3 H) 6.62 (t, 1 H) 6.68 (dd, 1 H) 7.02 (dd, 2 H) 7.22 (s, 1 H) 7.73 (d, 1 H) 11.51 (s, 1 H)

Synthesis of Example 22—2-(3-methoxypyridin-4-yl)-5-methyl-3-(phenylamino)-1,5,6,7-tetrahydro-4H-pyrrolo[3,2-c]pyridin-4-one Intermediate 1-2-12

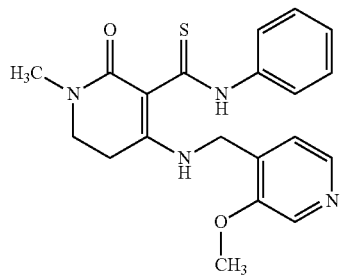 [SMILES: COc1cnccc1CNC1=C(C(=S)Nc2ccccc2)C(=O)N(C)CC1]

A solution of Intermediate 1-1-5 (250 mg, 0.95 mmol) and 1-(3-methoxypyridin-4-yl)methanamine (263 mg, 1.9 mmol) in DMA (2.5 mL) was heated in a sealed tube at 130° C. using a microwave for 30 mins. Allowed to cool. Purified by preparative HPLC (basic method) to give the desired product (135 mg, 37%).

1H-NMR (400 MHz, DMSO-d6), δ [ppm]=2.53-2.58 (2H), 2.79 (2H), 2.94 (3H), 3.31-3.36 (8H), 3.94 (3H), 4.65 (2H), 7.16-7.22 (1H), 7.28-7.46 (5H), 8.25 (1H), 8.39 (1H), 13.58 (1H), 14.68 (1H).

Example 22

2-(3-methoxypyridin-4-yl)-5-methyl-3-(phenylamino)-1,5,6,7-tetrahydro-4H-pyrrolo[3,2-c]pyridin-4-one

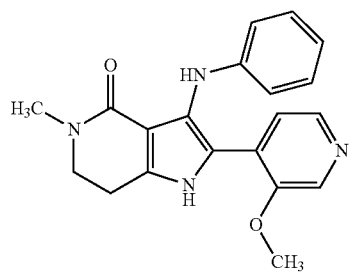 [SMILES: COc1cnccc1-c1[nH]c2c(c1Nc1ccccc1)C(=O)N(C)CC2]

A mixture of Intermediate 1-2-12 (133 mg, 348 μmol), hydrogen peroxide (34% in water, 63 μl, 695 μmol) in MeOH (10 mL) was heated at 90° C. for 1 h. Purification by preparative HPLC (Method: Waters XBridge C18 15μ 100× 30 mm; Solvent A: Water+0.2% Vol. Ammonium hydroxide (32%), Solvent B: Acetonitrile; Gradient: 0.00-0.50 min 26% B (25 to 70 mL/min), 0.51-5.50 min 26-40% B; Flow: 70 mL/min) gave the desired product (27.5 mg, 23%).

1H-NMR (400 MHz, DMSO-d6), Shift [ppm]=2.88 (3H), 2.96 (2H), 3.55 (2H), 3.93-3.97 (3H), 6.52-6.63 (3H), 7.00 (2H), 7.35 (1H), 7.48 (1H), 7.95 (1H), 8.33 (1H), 11.12 (1H).

Example 23—N-{4-[5-methyl-4-oxo-3-(phenylamino)-4,5,6,7-tetrahydro-1H-pyrrolo[3,2-c]pyridin-2-yl]pyridin-2-yl}acetamide

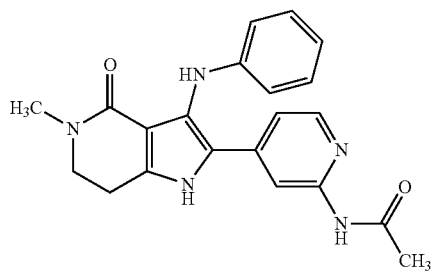 [SMILES: CC(=O)Nc1cc(-c2[nH]c3c(c2Nc2ccccc2)C(=O)N(C)CC3)ccn1]

To a solution of Example 21 (50 mg, 150 μmol) in pyridine (2 ml) was added acetyl chloride (23.5 mg, 300 μmol). The reaction was stirred at RT for 16 h and concentrated. The residue was purified by preparative HPLC (basic method) to give the desired product (15 mg, 25%).

1H-NMR (400 MHz, DMSO-d6), Shift [ppm]=2.04-2.10 (3H), 2.84-2.96 (6H), 3.55 (2H), 6.55-6.70 (4H), 7.02 (2H), 7.13 (1H), 7.34 (1H), 8.04 (1H), 8.20 (1H), 10.29 (1H), 11.74 (1H).

Example 24—N-{4-[5-methyl-4-oxo-3-(phenylamino)-4,5,6,7-tetrahydro-1H-pyrrolo[3,2-c]pyridin-2-yl]pyridin-2-yl}cyclopropanecarboxamide

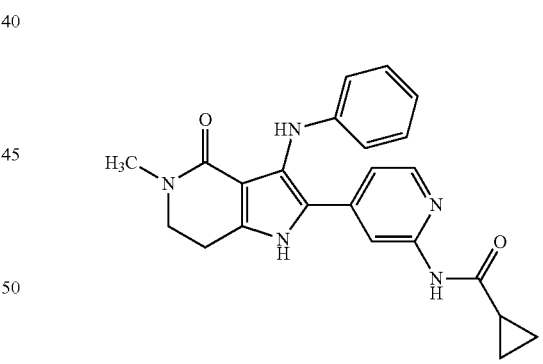

To a solution of Example 21 (50 mg, 150 μmol) in pyridine (2 ml) was added cyclopropanoyl chloride (31.4 mg, 300 μmol). The reaction was stirred at RT for 16 h and concentrated. The residue was purified by preparative HPLC (basic method) to give the desired product (15 mg, 25%).

1H-NMR (400 MHz, DMSO-d6), Shift [ppm]=0.80 (4H), 1.99 (1H), 2.84-2.95 (5H), 3.54 (2H), 6.54-6.65 (3H), 7.02 (2H), 7.12 (1H), 7.34 (1H), 8.04 (1H), 8.20 (1H), 10.61 (1H), 11.72 (1H).

Example 25—rel-(1R,2R)-2-fluoro-N-{4-[5-methyl-4-oxo-3-(phenylamino)-4,5,6,7-tetrahydro-1H-pyrrolo[3,2-c]pyridin-2-yl]pyridin-2-yl}cyclopropanecarboxamide

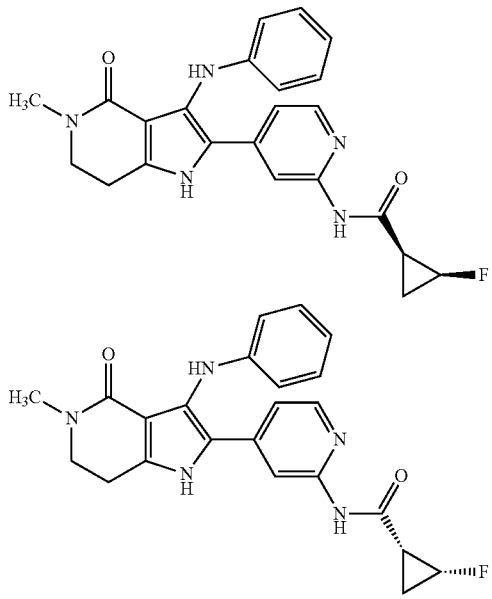

To a solution of cis-2-fluorocyclopropanecarboxylic acid (20.3 mg, 195 μmol) in DMF (0.5 ml) was added HATU (74 mg, 195 μmol) followed by DIPEA (25.2 mg, 195 μmol) and stirred at RT for 10 min. To this solution was added a solution of Example 21 (50 mg, 150 μmol) in DMF (1.5 ml) and the reaction was stirred at RT for 16 h. To the reaction was added a solution of cis-2-fluorocyclopropanecarboxylic acid (20.3 mg, 195 μmol), HATU (74 mg, 195 μmol) and DIPEA (25.2 mg, 195 μmol) in DMF (0.5 ml) and stirred at RT for 24 h. The reaction was heated at 50° C. for 24 h. The reaction mixture was purified by preparative HPLC (basic method) to give the desired product (22 mg, 31%).

1H-NMR (400 MHz, DMSO-d6), Shift [ppm]=1.07-1.28 (1H), 1.57-1.70 (1H), 2.16-2.23 (1H), 2.52-2.55 (1H), 2.85-2.98 (5H), 3.54 (2H), 4.74-5.14 (1H), 4.85 (1H), 5.01 (1H), 6.55-6.65 (3H), 7.03 (2H), 7.13 (1H), 7.30-7.39 (1H), 8.05 (1H), 8.24 (1H), 10.69 (1H), 11.79 (1H).

Synthesis of Example 26—2-[3-(2-hydroxyethoxy)pyridin-4-yl]-5-methyl-3-(phenylamino)-1,5,6,7-tetrahydro-4H-pyrrolo[3,2-c]pyridin-4-one Intermediate 1-2-13

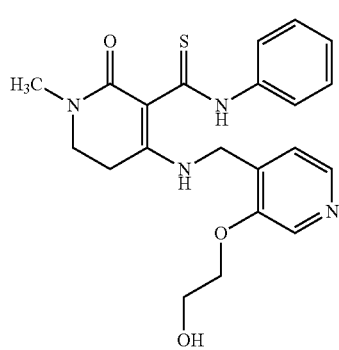 [SMILES: CN1CCC(NCc2ccncc2OCCO)=C(C(=S)Nc2ccccc2)C1=O]

A solution of Intermediate 1-1-5 (250 mg, 0.95 mmol) and 2-{[4-(aminomethyl)pyridin-3-yl]oxy}ethanol (192 mg, 1.14 mmol) in DMA (2.5 mL) was heated in a sealed tube at 130° C. using a microwave for 3 h. Allowed to cool. Purified by preparative HPLC (acidic method) to give the desired product (73 mg, 17%).

1H-NMR (400 MHz, DMSO-d6), Shift [ppm]=2.75-2.84 (2H), 2.89-2.99 (3H), 3.27-3.33 (2H), 3.72-3.80 (2H), 4.18 (2H), 4.69 (2H), 4.92 (1H), 7.17-7.45 (7H), 8.23 (1H), 8.38 (1H), 13.60 (1H), 14.69 (1H).

Example 26

2-[3-(2-hydroxyethoxy)pyridin-4-yl]-5-methyl-3-(phenylamino)-1,5,6,7-tetrahydro-4H-pyrrolo[3,2-c]pyridin-4-one

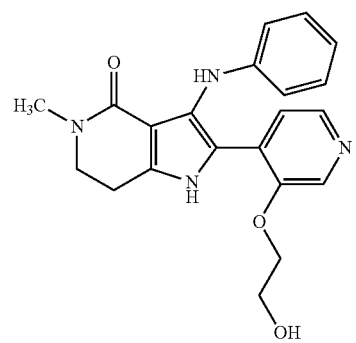 [SMILES: CN1CCc2[nH]c(-c3ccncc3OCCO)c(Nc3ccccc3)c2C1=O]

A mixture of Intermediate 1-2-13 (70 mg, 170 μmol), hydrogen peroxide (34% in water, 30.6 μl, 339 μmol) in MeOH (1 mL) was heated at 90° C. for 24 h. Purification by silica chromatography gave the desired product (7 mg, 10%).

1H-NMR (400 MHz, DMSO-d6), Shift [ppm]=2.82-2.97 (5H), 3.38-3.45 (2H), 3.51-3.61 (2H), 3.87 (2H), 4.21-4.33 (2H), 5.57-5.61 (1H), 6.54-6.64 (3H), 6.97-7.08 (2H), 7.23-7.43 (2H), 7.45-7.58 (1H), 7.96 (1H), 8.40 (1H), 11.33 (1H).

Synthesis of Example 27—2-[3-(cyclopropylmethoxy)pyridin-4-yl]-5-methyl-3-(phenylamino)-1,5,6,7-tetrahydro-4H-pyrrolo[3,2-c]pyridin-4-one Intermediate 1-2-14

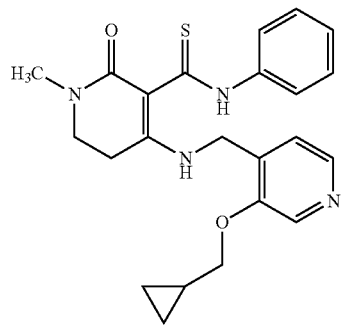 [SMILES: CN1CCC(NCc2ccncc2OCC2CC2)=C(C(=S)Nc2ccccc2)C1=O]

A solution of Intermediate 1-1-5 (126 mg, 0.468 mmol) and 1-[3-(cyclopropylmethoxy)pyridin-4-yl]methanamine (100 mg, 0.561 mmol) in DMA (2 mL) was heated in a sealed tube at 130° C. using a microwave for 3 h. Allowed to cool. Purified by preparative HPLC (acidic method) to give the desired product (31 mg, 15%).

1H-NMR (400 MHz, DMSO-d6), Shift [ppm]=0.34-0.42 (2H), 0.52-0.61 (2H), 1.23-1.33 (1H), 2.83 (2H), 2.94 (3H), 3.29-3.32 (2H), 4.02 (2H), 4.67 (2H), 7.07-7.22 (1H), 7.26-7.49 (5H), 8.22 (1H), 8.35 (1H), 13.57 (1H), 14.68 (1H).

Example 27

2-[3-(cyclopropylmethoxy)pyridin-4-yl]-5-methyl-3-(phenylamino)-1,5,6,7-tetrahydro-4H-pyrrolo[3,2-c]pyridin-4-one

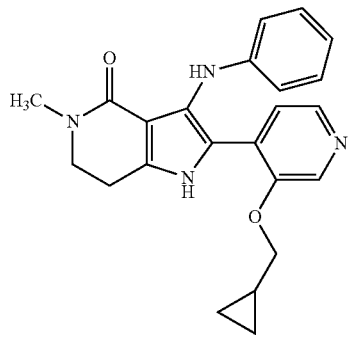 [SMILES: CN1CCc2[nH]c(-c3ccncc3OCC3CC3)c(Nc3ccccc3)c2C1=O]

A mixture of Intermediate 1-2-14 (29 mg, 69 µmol), hydrogen peroxide (34% in water, 12.4 µl, 137 µmol) in MeOH (1 mL) was heated at 90° C. for 24 h. Purification by preparative HPLC (basic method) gave the desired product (9 mg, 30%).

1H-NMR (400 MHz, DMSO-d6), Shift [ppm]=0.27-0.44 (2H), 0.51-0.63 (2H), 1.28-1.39 (1H), 2.87-3.00 (5H), 3.50-3.61 (2H), 3.87-4.04 (2H), 6.52-6.61 (3H), 6.98 (2H), 7.22-7.38 (1H), 7.38-7.54 (1H), 7.98 (1H), 8.31 (1H), 11.01 (1H).

Synthesis of Example 28—5-methyl-3-(phenylamino)-2-(3-propoxypyridin-4-yl)-1,5,6,7-tetrahydro-4H-pyrrolo[3,2-c]pyridin-4-one Intermediate 1-2-15

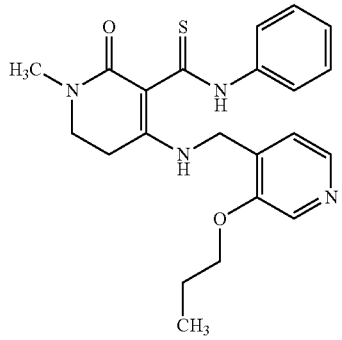 [SMILES: CCCOc1cnccc1CNC1=C(C(=S)Nc2ccccc2)C(=O)N(C)CC1]

A solution of Intermediate 1-1-5 (250 mg, 0.952 mmol) and 1-[3-(propyloxy)pyridin-4-yl]methanamine (190 mg, 1.14 mmol) in DMA (2.5 mL) was heated in a sealed tube at 130° C. for 3 h. Allowed to cool. Purified by preparative HPLC (acidic method) to give the desired product (58 mg, 13%).

1H-NMR (400 MHz, DMSO-d6), Shift [ppm]=1.01 (3H), 1.79 (2H), 2.75-2.85 (2H), 2.94 (3H), 3.30-3.33 (2H), 4.12 (2H), 4.65 (2H), 7.05-7.21 (1H), 7.24-7.49 (5H), 8.22 (1H), 8.37 (1H), 13.57 (1H), 14.68 (1H).

Example 28

5-methyl-3-(phenylamino)-2-(3-propoxypyridin-4-yl)-1,5,6,7-tetrahydro-4H-pyrrolo[3,2-c]pyridin-4-one

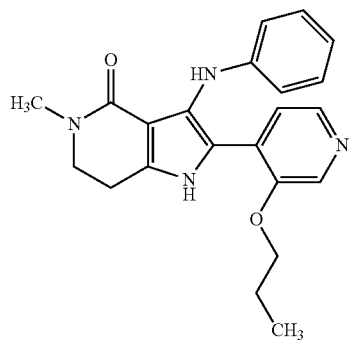 [SMILES: CCCOc1cnccc1-c1[nH]c2c(c1Nc1ccccc1)C(=O)N(C)CC2]

A mixture of Intermediate 1-2-15 (56 mg, 136 µmol), hydrogen peroxide (34% in water, 24.6 µl, 273 µmol) in MeOH (1 mL) was heated at 90° C. for 24 h. Purification by preparative HPLC (basic method) gave the desired product (14 mg, 26%).

1H-NMR (400 MHz, DMSO-d6), Shift [ppm]=0.96 (4H), 1.81 (2H), 2.86-3.05 (5H), 3.48-3.62 (2H), 3.97-4.13 (2H), 6.50-6.60 (3H), 6.97 (2H), 7.30 (1H), 7.41-7.49 (1H), 7.98 (1H), 8.32 (1H), 10.99 (1H).

Synthesis of Example 29—2-[3-(2,2-difluoroethoxy)pyridin-4-yl]-5-methyl-3-(phenylamino)-1,5,6,7-tetrahydro-4H-pyrrolo[3,2-c]pyridin-4-one Intermediate 1-2-16

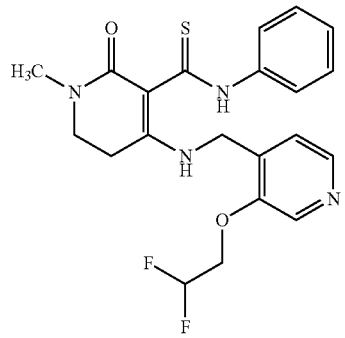 [SMILES: CN1CCC(NCc2ccncc2OCC(F)F)=C(C(=S)Nc2ccccc2)C1=O]

A solution of Intermediate 1-1-5 (250 mg, 0.952 mmol) and 1-[3-(2,2-difluoroethoxy)pyridin-4-yl]methanamine (215 mg, 1.14 mmol) in DMA (2.5 mL) was heated in a sealed tube at 130° C. for 3 h. Allowed to cool. Purified by preparative HPLC (acidic method) to give the desired product (69 mg, 16%).

1H-NMR (400 MHz, DMSO-d6), Shift [ppm]=2.78 (2H), 2.94 (3H), 3.25-3.31 (2H), 4.55 (2H), 4.69 (2H), 6.44 (1H), 7.07-7.22 (1H), 7.26-7.50 (5H), 7.28 (1H), 8.30 (1H), 8.46 (1H), 13.58 (1H), 14.69 (1H).

Example 29

2-[3-(2,2-difluoroethoxy)pyridin-4-yl]-5-methyl-3-(phenylamino)-1,5,6,7-tetrahydro-4H-pyrrolo[3,2-c]pyridin-4-one

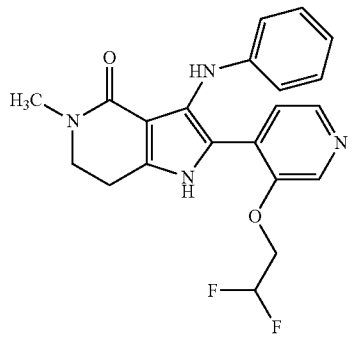 [SMILES: CN1CCc2[nH]c(-c3ccncc3OCC(F)F)c(Nc3ccccc3)c2C1=O]

A mixture of Intermediate 1-2-16 (68 mg, 157 µmol), hydrogen peroxide (34% in water, 28.3 µl, 314 µmol) in MeOH (1 mL) was heated at 90° C. for 24 h. Purification by preparative HPLC (basic method) gave the desired product (21 mg, 30%).

1H-NMR (400 MHz, DMSO-d6), Shift [ppm]=2.52-2.55 (2H), 2.86-3.00 (5H), 3.57 (2H), 4.33-4.47 (2H), 6.45 (1H), 6.41-6.61 (4H), 6.97 (2H), 7.44-7.55 (1H), 8.06 (1H), 8.37 (1H), 11.03 (1H).

Synthesis of Example 30—5-methyl-3-(phenylamino)-2-[3-(2,2,2-trifluoroethoxy)pyridin-4-yl]-1,5,6,7-tetrahydro-4H-pyrrolo[3,2-c]pyridin-4-one Intermediate 1-2-17

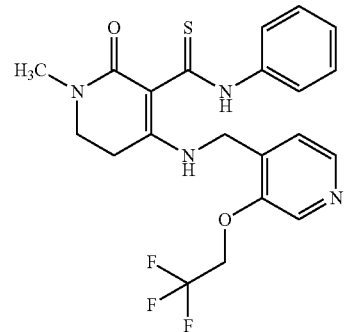 [SMILES: CN1CCC(NCc2ccncc2OCC(F)(F)F)=C(C(=S)Nc2ccccc2)C1=O]

A solution of Intermediate 1-1-5 (250 mg, 0.952 mmol) and 1-[3-(2,2,2-trifluoroethoxy)pyridin-4-yl]methanamine (236 mg, 1.14 mmol) in DMA (2.5 mL) was heated in a sealed tube at 130° C. for 3 h. Allowed to cool. Purified by preparative HPLC (acidic method) to give the desired product (76 mg, 17%).

1H-NMR (400 MHz, DMSO-d6), Shift [ppm]=2.77 (2H), 2.94 (3H), 3.29-3.33 (2H), 4.70 (2H), 5.00 (2H), 7.17-7.22 (1H), 7.33-7.46 (5H), 8.34 (1H), 8.50 (1H), 13.57 (1H), 14.68 (1H).

Example 30

5-methyl-3-(phenylamino)-2-[3-(2,2,2-trifluoroethoxy)pyridin-4-yl]-1,5,6,7-tetrahydro-4H-pyrrolo[3,2-c]pyridin-4-one

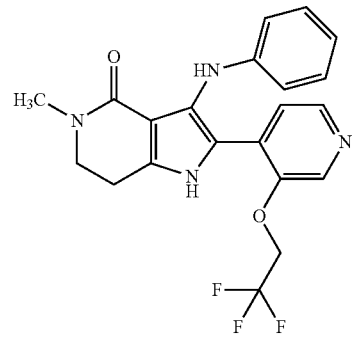 [SMILES: CN1CCc2[nH]c(-c3ccncc3OCC(F)(F)F)c(Nc3ccccc3)c2C1=O]

A mixture of Intermediate 1-2-17 (75 mg, 166 µmol), hydrogen peroxide (34% in water, 30 µl, 333 µmol) in MeOH (1 mL) was heated at 90° C. for 24 h. Purification by preparative HPLC (basic method) gave the desired product (24 mg, 33%).

1H-NMR (400 MHz, DMSO-d6), Shift [ppm]=2.88 (3H) 2.93 (2H), 3.56 (2H), 4.84 (2H), 6.49-6.60 (3H), 6.96 (2H), 7.24-7.51 (3H), 8.10 (1H), 8.44 (1H), 11.06 (1H).

Synthesis of Example 31—2-[3-(2-methoxyethoxy)pyridin-4-yl]-5-methyl-3-(phenylamino)-1,5,6,7-tetrahydro-4H-pyrrolo[3,2-c]pyridin-4-one Intermediate 1-2-18

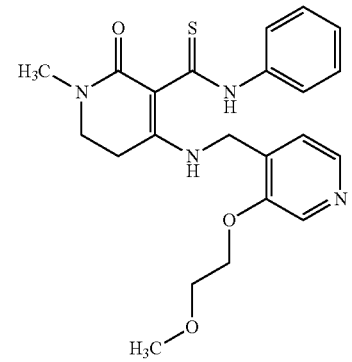 [SMILES: COCCOc1cnccc1CNC1=C(C(=S)Nc2ccccc2)C(=O)N(C)CC1]

A solution of Intermediate 1-1-5 (864 mg, 3.29 mmol) and 1-[3-(2-methoxyethoxy)pyridin-4-yl]methanamine (500 mg, 2.74 mmol) in DMA (10 mL) was heated in a sealed tube at 130° C. for 60 min. Allowed to cool. Purified by silica chromatography (DCM:MeOH) to give the desired product (507 mg, 43%).

1H-NMR (400 MHz, DMSO-d6), Shift [ppm]=2.75-2.84 (2H), 2.90-2.97 (3H), 3.32-3.34 (5H), 3.69-3.74 (2H), 4.26-

4.32 (2H), 4.65 (2H), 7.13-7.22 (1H), 7.30-7.46 (5H), 8.18-8.26 (1H), 8.37-8.43 (1H), 13.58 (1H), 14.68 (1H).

Example 31

2-[3-(2-methoxyethoxy)pyridin-4-yl]-5-methyl-3-(phenylamino)-1,5,6,7-tetrahydro-4H-pyrrolo[3,2-c]pyridin-4-one

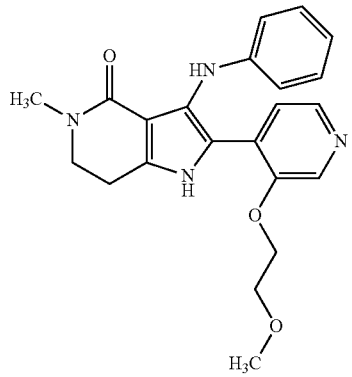 [SMILES: COCCOc1cnccc1-c1[nH]c2c(c1Nc1ccccc1)C(=O)N(C)CC2]

A mixture of Intermediate 1-2-18 (507 mg, 1.19 mmol), hydrogen peroxide (34% in water, 214.3 µl, 2.38 mmol) in MeOH (9 mL) was heated at 90° C. for 3 h. Purification by silica chromatography (DCM:MeOH) and crystallization from MeOH gave the desired product (70 mg, 15%).

1H-NMR (400 MHz, DMSO-d6), Shift [ppm]=2.86-2.96 (5H), 3.39-3.42 (3H), 3.56 (2H), 3.79 (2H), 4.30-4.35 (2H), 6.54-6.63 (3H), 7.00 (2H), 7.33 (1H), 7.49 (1H), 7.97 (1H), 8.38 (1H), 10.94 (1H).

Synthesis of Example 32—2-[3-(benzyloxy)pyridin-4-yl]-5-methyl-3-(phenylamino)-1,5,6,7-tetrahydro-4H-pyrrolo[3,2-c]pyridin-4-one Intermediate 1-2-19

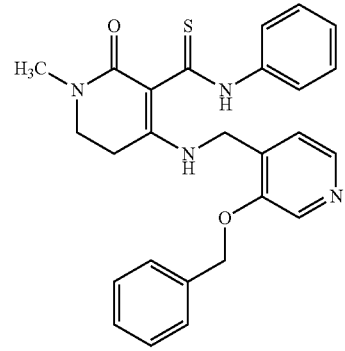 [SMILES: CN1CCC(NCc2ccncc2OCc2ccccc2)=C(C(=S)Nc2ccccc2)C1=O]

A solution of Intermediate 1-1-5 (250 mg, 0.953 mmol) and 1-[3-(benzyloxy)pyridin-4-yl]methanamine (204 mg, 0.953 mmol) in DMA (1 mL) was heated in a sealed tube at 120° C. for 90 min. Allowed to cool. Purified by preparative HPLC (basic method) to give the desired product (116 mg, 25%).

1H-NMR (400 MHz, DMSO-d6), Shift [ppm]=2.67-2.77 (2H), 2.88-2.95 (3H), 3.27 (2H), 4.72 (2H), 5.32 (2H), 7.19 (1H), 7.30-7.45 (8H), 7.52 (2H), 8.24 (1H), 8.44 (1H), 13.58 (1H), 14.70 (1H).

Example 32

2-[3-(benzyloxy)pyridin-4-yl]-5-methyl-3-(phenylamino)-1,5,6,7-tetrahydro-4H-pyrrolo[3,2-c]pyridin-4-one

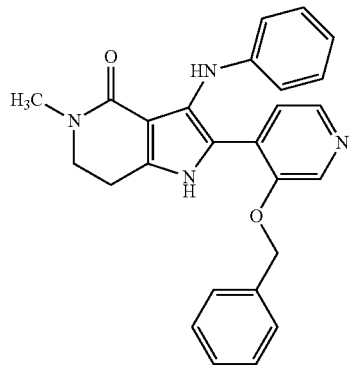 [SMILES: CN1CCc2[nH]c(-c3ccncc3OCc3ccccc3)c(Nc3ccccc3)c2C1=O]

A mixture of Intermediate 1-2-19 (116 mg, 0.253 mmol), hydrogen peroxide (34% in water, 45.6 µl, 0.51 mmol) in MeOH (4 mL) was heated at 90° C. for 3 h. Purification by preparative HPLC (basic method) gave the desired product (24 mg, 21%).

1H-NMR (400 MHz, DMSO-d6), Shift [ppm]=2.88 (3H), 2.95 (2H), 3.37-3.59 (2H), 5.36 (2H), 6.50 (2H), 6.58 (1H), 6.96 (2H), 7.30-7.49 (8H), 7.94 (1H), 8.31 (1H), 11.17 (1H).

Synthesis of Example 33—5-methyl-3-(phenylamino)-2-[3-(3,3,3-trifluoropropoxy)pyridin-4-yl]-1,5,6,7-tetrahydro-4H-pyrrolo[3,2-c]pyridin-4-one Intermediate 1-20

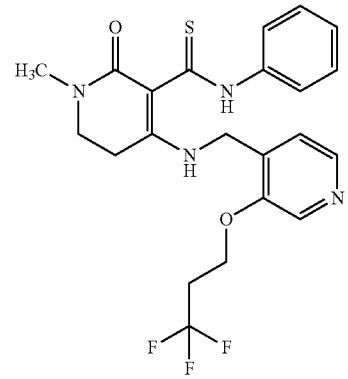 [SMILES: CN1CCC(NCc2ccncc2OCCC(F)(F)F)=C(C(=S)Nc2ccccc2)C1=O]

A solution of Intermediate 1-1-5 (250 mg, 0.953 mmol) and 1-[3-(3,3,3-trifluoropropoxy)pyridin-4-yl]methanamine (210 mg, 0.953 mmol) in DMA (1 mL) was heated in a sealed tube at 120° C. for 90 min. Allowed to cool. Purified by preparative HPLC (basic method) to give the desired product (111 mg, 24%).

1H-NMR (400 MHz, DMSO-d6), Shift [ppm]=2.74-2.95 (7H), 3.31-3.35 (2H), 4.42 (2H), 4.63 (2H), 7.19 (1H), 7.31-7.45 (5H), 8.27 (1H), 8.44 (1H), 13.57 (1H), 14.68 (1H).

Example 33

5-methyl-3-(phenylamino)-2-[3-(3,3,3-trifluoropropoxy)pyridin-4-yl]-1,5,6,7-tetrahydro-4H-pyrrolo[3,2-c]pyridin-4-one

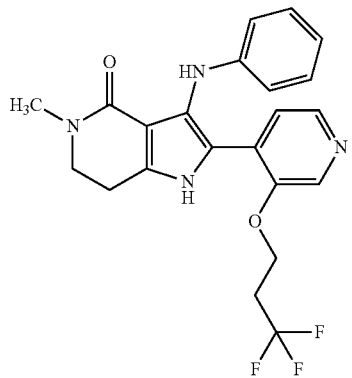 [SMILES: CN1CCc2[nH]c(-c3ccncc3OCCC(F)(F)F)c(Nc3ccccc3)c2C1=O]

A mixture of Intermediate 1-2-20 (111 mg, 0.239 mmol), hydrogen peroxide (34% in water, 43.1 µl, 0.48 mmol) in MeOH (4 mL) was heated at 90° C. for 16 h. Purification by preparative HPLC (basic method) gave the desired product (32 mg, 30%).

1H-NMR (400 MHz, DMSO-d6), Shift [ppm]=2.86-3.00 (7H), 3.56 (2H), 4.31 (2H), 6.51-6.61 (3H), 6.97 (2H), 7.33 (1H), 7.51 (1H), 8.02 (1H), 8.36 (1H), 10.93 (1H).

Synthesis of Example 34—5-methyl-3-(phenylamino)-2-{3-[(3S)-tetrahydrofuran-3-ylmethoxy]pyridin-4-yl}-1,5,6,7-tetrahydro-4H-pyrrolo[3,2-c]pyridin-4-one Intermediate 1-2-21

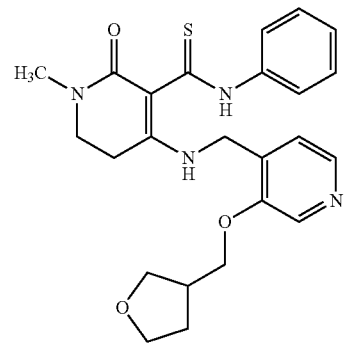 [SMILES: CN1CCC(NCc2ccncc2OCC2CCOC2)=C(C(=S)Nc2ccccc2)C1=O]

A solution of Intermediate 1-1-5 (250 mg, 0.953 mmol) and [3-(tetrahydrofuran-3-ylmethoxy)-4-pyridyl]methanamine (198 mg, 0.953 mmol) in DMA (3.5 mL) was heated in a sealed tube at 130° C. for 60 min. Allowed to cool. Purified by preparative HPLC (basic method) to give the desired product (40 mg, 9%).

1H-NMR (400 MHz, DMSO-d6), Shift [ppm]=1.67-1.75 (1H), 1.99-2.08 (1H), 2.66-2.82 (3H), 2.89-2.95 (3H), 3.31-3.38 (2H), 3.58-3.69 (2H), 3.74-3.84 (2H), 4.05-4.17 (2H), 4.65 (2H), 7.19 (1H), 7.29-7.44 (5H), 8.24 (1H), 8.39 (1H), 13.55 (1H), 14.68 (1H).

Example 34

5-methyl-3-(phenylamino)-2-{3-[(3S)-tetrahydrofuran-3-ylmethoxy]pyridin-4-yl}-1,5,6,7-tetrahydro-4H-pyrrolo[3,2-c]pyridin-4-one

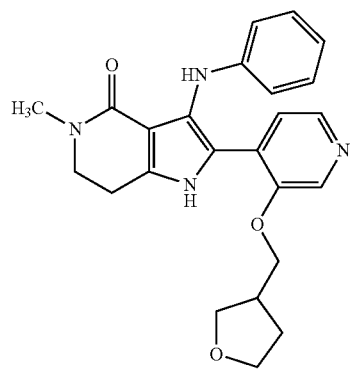 [SMILES: CN1CCc2[nH]c(-c3ccncc3OCC3CCOC3)c(Nc3ccccc3)c2C1=O]

A mixture of Intermediate 1-2-21 (40 mg, 88 µmol), hydrogen peroxide (34% in water, 65 µl, 160 µmol) in MeOH (0.65 mL) was heated at 90° C. for 16 h. Purification by preparative HPLC (basic method) gave the desired product (10 mg, 27%).

1H-NMR (400 MHz, DMSO-d6), Shift [ppm]=1.74 (1H), 2.07 (1H), 2.71-2.82 (1H), 2.85-2.95 (4H), 3.51-3.77 (5H), 3.87 (1H), 4.03-4.21 (2H), 6.51-6.62 (3H), 6.99 (2H), 7.36 (1H), 7.46 (1H), 7.97 (1H), 8.33 (1H), 11.03 (1H).

Synthesis of Example 35—2-[3-(3,3-dimethylbutoxy)pyridin-4-yl]-5-methyl-3-(phenylamino)-1,5,6,7-tetrahydro-4H-pyrrolo[3,2-c]pyridin-4-one Intermediate 1-2-22

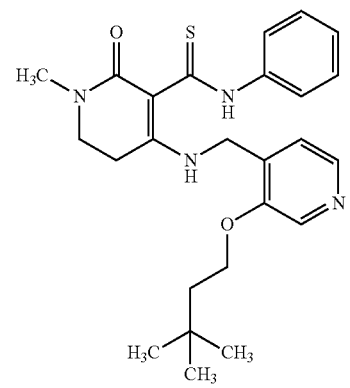 [SMILES: CN1CCC(NCc2ccncc2OCCC(C)(C)C)=C(C(=S)Nc2ccccc2)C1=O]

A solution of Intermediate 1-1-5 (250 mg, 0.953 mmol) and 1-[3-(3,3-dimethylbutoxy)pyridin-4-yl]methanamine (198 mg, 0.953 mmol) in DMA (3.5 mL) was heated in a sealed tube at 130° C. for 60 min. Allowed to cool. Purified by preparative HPLC (basic method) to give the desired product (45 mg, 11%).

1H-NMR (400 MHz, DMSO-d6), Shift [ppm]=0.96-1.05 (9H), 1.74 (2H), 2.78 (2H), 2.94 (3H), 3.31-3.35 (2H), 4.21 (2H), 4.62 (2H), 7.19 (1H), 7.29-7.45 (5H), 8.22 (1H), 8.42 (1H), 13.54 (1H), 14.68 (1H).

Example 35

2-[3-(3,3-dimethylbutoxy)pyridin-4-yl]-5-methyl-3-(phenylamino)-1,5,6,7-tetrahydro-4H-pyrrolo[3,2-c]pyridin-4-one

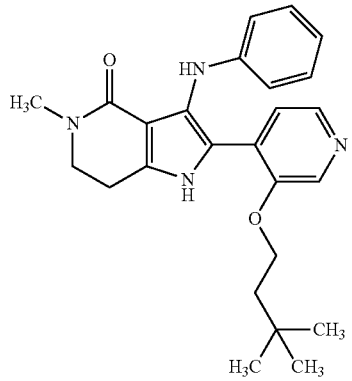 [SMILES: CN1CCc2[nH]c(-c3ccncc3OCCC(C)(C)C)c(Nc3ccccc3)c2C1=O]

A mixture of Intermediate 1-2-22 (43 mg, 95 μmol), hydrogen peroxide (34% in water, 70 μl, 172 μmol) in MeOH (0.7 mL) was heated at 90° C. for 16 h. Purification by preparative HPLC (basic method) gave the desired product (20 mg, 50%).

1H-NMR (400 MHz, DMSO-d6), Shift [ppm]=0.84-1.03 (9H), 1.74 (2H), 2.85-2.94 (5H), 3.54 (2H), 4.12 (2H), 6.48-6.58 (3H), 6.89-7.01 (2H), 7.29 (1H), 7.44 (1H), 7.97 (1H), 8.33 (1H), 10.99 (1H).

Synthesis of Example 36—2-(3H-imidazo[4,5-b]pyridin-7-yl)-5-methyl-3-(phenylamino)-1,5,6,7-tetrahydro-4H-pyrrolo[3,2-c]pyridin-4-one Intermediate 1-2-23

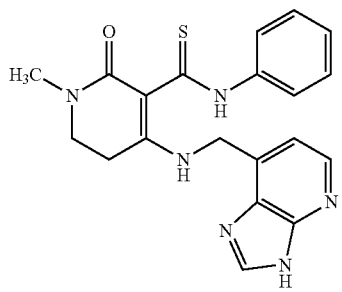 [SMILES: CN1CCC(NCc2ccnc3[nH]cnc23)=C(C(=S)Nc2ccccc2)C1=O]

A solution of Intermediate 1-1-5 (250 mg, 0.953 mmol) and 1-(3H-imidazo[4,5-b]pyridin-7-yl)methanamine (141 mg, 0.953 mmol) in DMA (1.1 mL) was heated in a sealed tube at 120° C. for 90 min. Allowed to cool. Purified by preparative HPLC (basic method) to give the desired product (22 mg, 5%).

1H-NMR (400 MHz, DMSO-d6), Shift [ppm]=2.85-2.96 (5H), 3.29-3.32 (2H), 5.08 (2H), 7.16-7.24 (2H), 7.33-7.46 (4H), 8.37 (1H), 8.48 (1H), 13.15 (1H), 13.73 (1H), 14.70 (1H).

Example 36

2-(3H-imidazo[4,5-b]pyridin-7-yl)-5-methyl-3-(phenylamino)-1,5,6,7-tetrahydro-4H-pyrrolo[3,2-c]pyridin-4-one

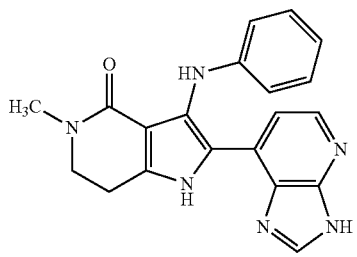 [SMILES: CN1CCc2[nH]c(-c3ccnc4[nH]cnc34)c(Nc3ccccc3)c2C1=O]

A mixture of Intermediate 1-2-23 (18 mg, 46 μmol), urea hydrogen peroxide (6.4 mg, 69 μmol) in MeOH (1.8 mL) was heated at 50° C. for 16 h. Purification by preparative HPLC (acidic method) gave the desired product (2.5 mg, 15%).

1H-NMR (400 MHz, DMSO-d6), Shift [ppm]=2.89 (3H), 2.99-3.12 (2H), 3.58 (2H), 6.59-6.71 (3H), 6.99-7.15 (3H), 7.98 (1H), 8.09 (1H), 8.54 (1H), 11.84 (1H), 13.27 (1H).

Synthesis of Example 37—2-[3-(cyclopropylmethoxy)pyridin-4-yl]-3-[(3,4-difluorophenyl)amino]-1,5,6,7-tetrahydro-4H-pyrrolo[3,2-c]pyridin-4-one Intermediate 1-1-6

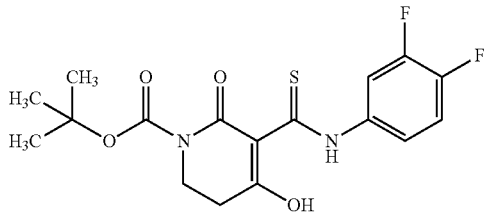 [SMILES: CC(C)(C)OC(=O)N1CCC(O)=C(C(=S)Nc2ccc(F)c(F)c2)C1=O]

To a mixture of N-tert-butoxycarbonyl-2,4-piperidindione (7.48 g, 35.1 mmol) and 3,4-difluorophenylisothiocyanate (6.19 g, 35.1 mmol) in MeCN (35 mL) cooled to 0° C. under Argon was added slowly dropwise DBU (6.67 g, 43.8 mmol). Solid formed and additional MeCN (10 mL) added and the reaction was stirred at RT for 16 h. The reaction was poured onto ice-water containing concentrated HCL (5 mL). The precipitate formed and was collected by filtration, dried in vacuo to give the desired product (11.36 g, 84%).

1H NMR (400 MHz, CDCl3-d6) ∟ ppm 1.56 (9 H), 2.80-2.84 (2 H), 3.83-3.87 (2 H), 7.11-7.14 (1 H), 7.14-7.26 (1 H), 7.37-7.42 (1 H), 13.61 (1 H).

Intermediate 1-1-7

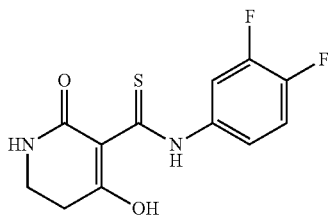 [SMILES: O=C1NCCC(O)=C1C(=S)Nc1ccc(F)c(F)c1]

To a solution of Intermediate 1-1-6 (11.35 g, 29.5 mmol) in DCM (60 mL) was added TFA (13.6 mL, 177 mmol) and stirred at RT for 3 h. The reaction mixture was concentrated and the residue was crystallized from EtOAc to give the desired product (7.48 g, 89%).

1H NMR (400 MHz, DMSO-d6) ppm 2.62-2.77 (2 H), 3.27-3.43 (2 H), 7.22 (1 H), 7.44-7.64 (2 H), 9.15 (0.5 H), 9.34 (0.5 H), 14.26 (0.5 H), 14.61 (0.5 H), 16.36 (1 H).

Intermediate 1-2-24

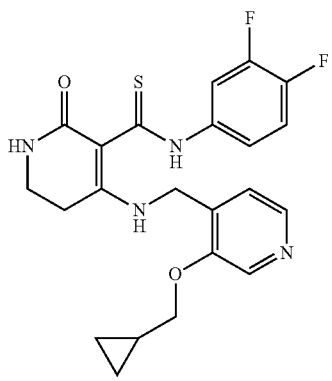 [SMILES: O=C1NCCC(NCc2ccncc2OCC2CC2)=C1C(=S)Nc1ccc(F)c(F)c1]

A solution of Intermediate 1-1-7 (250 mg, 0.879 mmol) and 1-[3-(cyclopropylmethoxy)pyridin-4-yl]methanamine (188 mg, 1.06 mmol) in DMA (2.6 mL) was heated in a sealed tube at 130° C. for 60 min. Allowed to cool. Purified by preparative HPLC (basic method) to give the desired product (70 mg, 18%).

1H-NMR (400 MHz, DMSO-d6), Shift [ppm]=0.31-0.42 (2H), 0.52-0.62 (2H), 1.22-1.32 (1H), 2.78 (2H), 3.12-3.31 (2H), 4.02 (2H), 4.67 (2H), 7.14 (1H), 7.30 (1H), 7.41 (1H), 7.64-7.77 (2H), 8.21 (1H), 8.34 (1H), 13.61 (1H), 14.88 (1H).

Example 37

2-[3-(cyclopropylmethoxy)pyridin-4-yl]-3-[(3,4-difluorophenyl)amino]-1,5,6,7-tetrahydro-4H-pyrrolo[3,2-c]pyridin-4-one

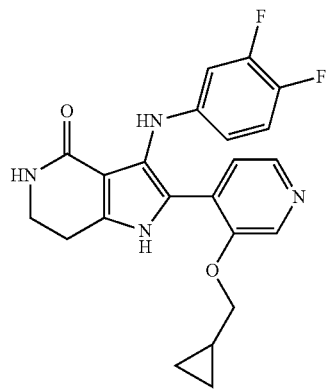 [SMILES: O=C1NCCc2[nH]c(-c3ccncc3OCC3CC3)c(Nc3ccc(F)c(F)c3)c21]

A mixture of Intermediate 1-2-24 (130 mg, 292 μmol), hydrogen peroxide (34% in water, 52.7 μl, 585 μmol) in MeOH (9.9 mL) was heated at 90° C. for 16 h. Purification by preparative HPLC (basic method) gave the desired product (40 mg, 33%).

1H-NMR (400 MHz, DMSO-d6), Shift [ppm]=0.25-0.40 (2H), 0.48-0.61 (2H), 1.22-1.33 (1H), 2.84 (2H), 3.36-3.44 (2H), 3.96 (2H), 6.32-6.45 (2H), 6.98-7.10 (2H), 7.29 (1H), 7.48 (1H), 8.05 (1H), 8.33 (1H), 11.16 (1H).

Synthesis of Example 38—2-[3-(cyclopropylmethoxy)pyridin-4-yl]-3-[(4-fluorophenyl)amino]-1,5,6,7-tetrahydro-4H-pyrrolo[3,2-c]pyridin-4-one Intermediate 1-2-25

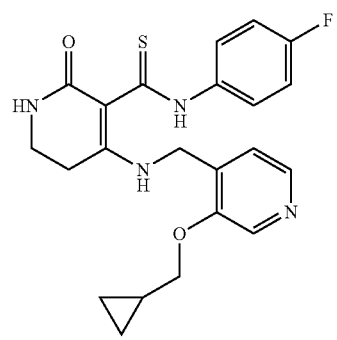 [SMILES: O=C1NCCC(NCc2ccncc2OCC2CC2)=C1C(=S)Nc1ccc(F)cc1]

A solution of Intermediate 1-1-7 (250 mg, 0.879 mmol) and 1-[3-(cyclopropylmethoxy)pyridin-4-yl]methanamine (201 mg, 1.13 mmol) in DMA (2.8 mL) was heated in a sealed tube at 130° C. for 60 min. Allowed to cool. Purified by preparative HPLC (basic method) to give the desired product (50 mg, 12%).

1H-NMR (400 MHz, DMSO-d6), Shift [ppm]=0.30-0.42 (2H), 0.51-0.62 (2H), 1.22-1.32 (1H), 2.77 (2H), 3.12-3.31 (2H), 3.96-4.08 (2H), 4.66 (2H), 7.19 (2H), 7.28-7.42 (3H), 7.69 (1H), 8.11-8.35 (2H), 13.64 (1H), 14.70 (1H).

Example 38

2-[3-(cyclopropylmethoxy)pyridin-4-yl]-3-[(4-fluorophenyl)amino]-1,5,6,7-tetrahydro-4H-pyrrolo[3,2-c]pyridin-4-one

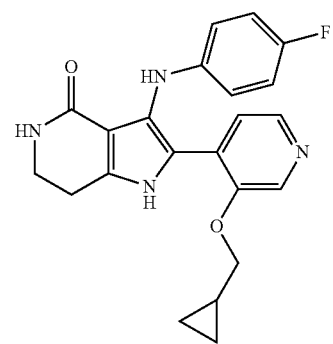 [SMILES: O=C1NCCc2[nH]c(-c3ccncc3OCC3CC3)c(Nc3ccc(F)cc3)c21]

A mixture of Intermediate 1-2-25 (60 mg, 141 μmol), hydrogen peroxide (34% in water, 25.4 μl, 281 μmol) in MeOH (4.8 mL) was heated at 90° C. for 16 h. Purification by preparative HPLC (basic method) gave the desired product (30 mg, 54%).

1H-NMR (400 MHz, DMSO-d6), Shift [ppm]=0.29-0.42 (3H), 0.51-0.61 (3H), 1.22-1.38 (1H), 2.84 (2H), 3.36-3.43 (2H), 3.94-4.01 (3H), 6.51-6.57 (2H), 6.82 (2H), 7.07 (1H), 7.28 (1H), 7.33 (1H), 7.99 (1H), 8.31 (1H), 11.04 (1H).

Synthesis of Example 39—2-[3-(cyclopropylmethoxy)pyridin-4-yl]-3-[(3-fluorophenyl)amino]-1,5,6,7-tetrahydro-4H-pyrrolo[3,2-c]pyridin-4-one Intermediate 1-1-8

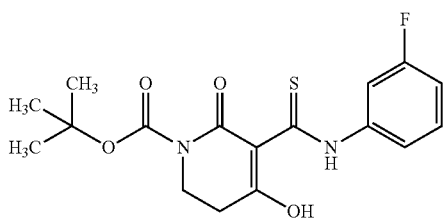 [SMILES: CC(C)(C)OC(=O)N1CCC(O)=C(C(=S)Nc2cccc(F)c2)C1=O]

To a mixture of N-tert-butoxycarbonyl-2,4-piperidindione (7 g, 32.8 mmol) and 3-fluorophenylisothiocyanate (5.03 g, 32.8 mmol) in MeCN (37 mL) cooled to 0° C. under Argon was added slowly dropwise DBU (6.31 g, 41.5 mmol) and then stirred at RT for 16 h. The reaction was poured onto ice-water containing concentrated HCL (5 mL). The precipitate formed and was collected by filtration, dried in vacuo to give the desired product (11.99 g, 99%).

Intermediate 1-1-9

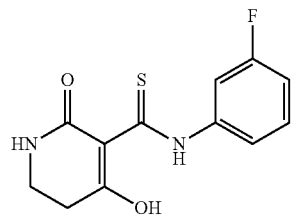 [SMILES: O=C1NCCC(O)=C1C(=S)Nc1cccc(F)c1]

To a solution of Intermediate 1-1-8 (11.9 g, 32.5 mmol) in DCM (80 mL) was added TFA (20 mL) and stirred at RT for 3 h. The reaction mixture was concentrated and the residue was crystallized from EtOAc to give the desired product (5.1 g, 59%).

1H NMR (400 MHz, CDCl3) ∟ ppm 2.81-2.84 (2 H), 3.43-3.48 (2 H), 5.67 (1 H), 6.98-7.01 (1 H), 7.32-7.40 (2 H), 14.10 (1 H).

Intermediate 1-2-26

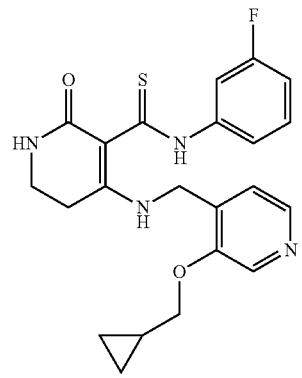 [SMILES: O=C1NCCC(NCc2ccncc2OCC2CC2)=C1C(=S)Nc1cccc(F)c1]

A solution of Intermediate 1-1-9 (250 mg, 0.939 mmol) and 1-[3-(cyclopropylmethoxy)pyridin-4-yl]methanamine (201 mg, 1.13 mmol) in DMA (2.8 mL) was heated in a sealed tube at 130° C. for 60 min. Allowed to cool. Purified by preparative HPLC (basic method) to give the desired product (60 mg, 15%).

1H-NMR (400 MHz, DMSO-d6), Shift [ppm]=0.31-0.43 (2H), 0.52-0.61 (2H), 1.22-1.33 (1H), 2.78 (2H), 3.12-3.31 (2H), 4.02 (2H), 4.68 (2H), 7.02 (1H), 7.16 (1H), 7.29-7.42 (2H), 7.53 (1H), 7.74 (1H), 8.22 (1H), 8.35 (1H), 13.64 (1H), 14.97 (1H).

Example 39

2-[3-(cyclopropylmethoxy)pyridin-4-yl]-3-[(3-fluorophenyl)amino]-1,5,6,7-tetrahydro-4H-pyrrolo[3,2-c]pyridin-4-one

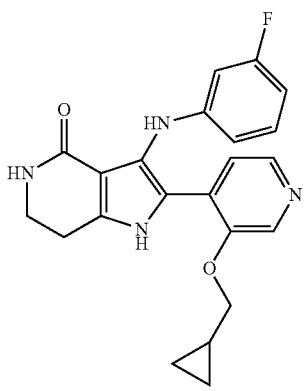 [SMILES: O=C1NCCc2[nH]c(-c3ccncc3OCC3CC3)c(Nc3cccc(F)c3)c21]

A mixture of Intermediate 1-2-26 (100 mg, 234 μmol), hydrogen peroxide (34% in water, 42.3 μl, 469 μmol) in MeOH (8 mL) was heated at 90° C. for 16 h. Purification by preparative HPLC (basic method) gave the desired product (30 mg, 33%).

1H-NMR (400 MHz, DMSO-d6), Shift [ppm]=0.28-0.39 (2H), 0.50-0.60 (2H), 1.22-1.34 (1H), 2.84 (2H), 3.35-3.44 (2H), 3.93-4.01 (2H), 6.21 (1H), 6.30 (1H), 6.40 (1H), 6.95-7.09 (2H), 7.31 (1H), 7.55 (1H), 8.04 (1H), 8.33 (1H), 11.15 (1H).

Example 40—(1S,2S)-2-fluoro-N-{4-[5-methyl-4-oxo-3-(phenylamino)-4,5,6,7-tetrahydro-1H-pyrrolo[3,2-c]pyridin-2-yl]pyridin-2-yl}cyclopropanecarboxamide

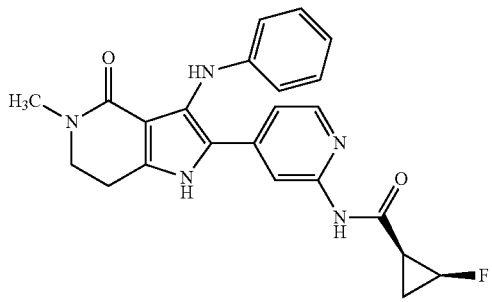 [SMILES: CN1CCc2[nH]c(-c3ccnc(NC(=O)[C@@H]4C[C@@H]4F)c3)c(Nc3ccccc3)c2C1=O]

To a solution of (1S,2S)-2-fluorocyclopropanecarboxylic acid (71.8 mg, 690 µmol) in DMF (0.5 ml) was added HATU (262 mg, 690 µmol) followed by DIPEA (167 mg, 1.29 mmol) and stirred at RT for 10 min. To this solution was added a solution of Example 21 (100 mg, 300 µmol) in DMF (1.5 ml) and the reaction was stirred at 50° C. for 16 h. The reaction mixture was purified by preparative HPLC (basic method) and silica chromatography (MeOH:DCM+0.1% NH3) to give the desired product (45 mg, 34%).

1H-NMR (400 MHz, DMSO-d6), Shift [ppm]=1.10-1.29 (1H), 1.57-1.69 (1H), 2.15-2.23 (1H), 2.52-2.54 (1H), 2.84-2.95 (5H), 3.54 (2H), 4.73-5.17 (1H), 4.84 (1H), 5.00 (1H), 6.55-6.64 (3H), 7.02 (2H), 7.13 (1H), 7.35 (1H), 8.04 (1H), 8.23 (1H), 10.68 (1H), 11.78 (1H).

Synthesis of Example 41—2-[3-(2,2-difluoroethoxy)pyridin-4-yl]-3-[(3-fluorophenyl)amino]-1,5,6,7-tetrahydro-4H-pyrrolo[3,2-c]pyridin-4-one Intermediate 1-2-27

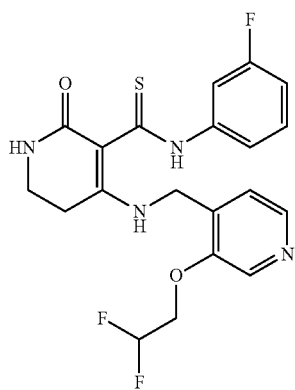 [SMILES: O=C1NCCC(NCc2ccncc2OCC(F)F)=C1C(=S)Nc1cccc(F)c1]

A solution of Intermediate 1-1-9 (250 mg, 0.939 mmol) and 1-[3-(2,2-difluoroethoxy)pyridin-4-yl]methanamine (201 mg, 1.13 mmol) in DMA (2.8 mL) was heated in a sealed tube at 130° C. for 60 min. Allowed to cool. Purified by preparative HPLC (basic method) to give the desired product (100 mg, 24%).

1H-NMR (400 MHz, DMSO-d6), Shift [ppm]=2.53-2.76 (1H), 2.69-2.80 (1H), 3.11-3.31 (2H), 4.46-4.63 (2H), 4.69 (2H), 6.43 (1H), 7.02 (1H), 7.16 (1H), 7.30-7.42 (2H), 7.54 (1H), 7.76 (1H), 8.30 (1H), 8.46 (1H), 13.65 (1H), 14.97 (1H).

Example 41

2-[3-(2,2-difluoroethoxy)pyridin-4-yl]-3-[(3-fluorophenyl)amino]-1,5,6,7-tetrahydro-4H-pyrrolo[3,2-c]pyridin-4-one

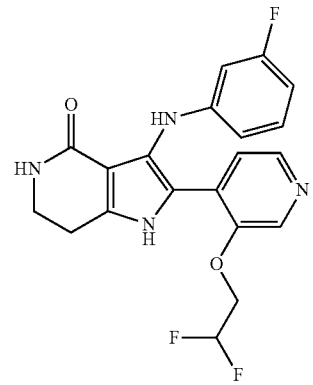 [SMILES: O=C1NCCc2[nH]c(-c3ccncc3OCC(F)F)c(Nc3cccc(F)c3)c21]

A mixture of Intermediate 1-2-27 (120 mg, 275 µmol), hydrogen peroxide (34% in water, 49.6 µl, 550 µmol) in MeOH (9.3 mL) was heated at 90° C. for 16 h. Purification by preparative HPLC (basic method) gave the desired product (30 mg, 27%).

1H-NMR (400 MHz, DMSO-d6), Shift [ppm]=2.84 (2H), 3.35-3.43 (2H), 4.39 (2H), 6.19-6.42 (3H), 6.41 (1H), 6.94-7.01 (1H), 7.07 (1H), 7.33 (1H), 7.60 (1H), 8.12 (1H), 8.39 (1H), 11.18 (1H).

Synthesis of Example 42—2-[3-(2,2-difluoroethoxy)pyridin-4-yl]-3-[(4-fluorophenyl)amino]-1,5,6,7-tetrahydro-4H-pyrrolo[3,2-c]pyridin-4-one Intermediate 1-2-28

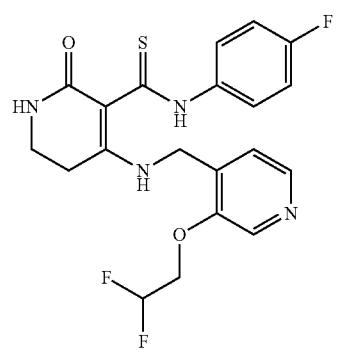 [SMILES: O=C1NCCC(NCc2ccncc2OCC(F)F)=C1C(=S)Nc1ccc(F)cc1]

A solution of Intermediate 1-1-4 (250 mg, 0.939 mmol) and 1-[3-(2,2-difluoroethoxy)pyridin-4-yl]methanamine (212 mg, 1.13 mmol) in DMA (2.8 mL) was heated in a sealed tube at 130° C. for 60 min. Allowed to cool. Purified by preparative HPLC (basic method) to give the desired product (100 mg, 22%).

1H-NMR (400 MHz, DMSO-d6), Shift [ppm]=2.64-2.78 (2H), 3.10-3.31 (2H), 4.46-4.62 (2H), 4.68 (2H), 6.43 (1H), 7.19 (2H), 7.32 (1H), 7.37-7.43 (2H), 7.71 (1H), 8.30 (1H), 8.46 (1H), 13.65 (1H), 14.71 (1H).

Example 42

2-[3-(2,2-difluoroethoxy)pyridin-4-yl]-3-[(4-fluorophenyl)amino]-1,5,6,7-tetrahydro-4H-pyrrolo[3,2-c]pyridin-4-one

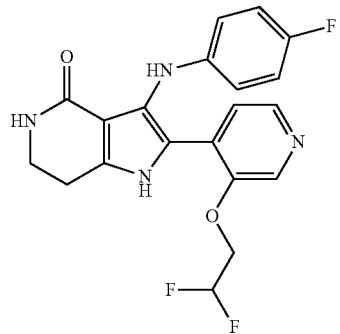 [SMILES: O=C1NCCc2[nH]c(-c3ccncc3OCC(F)F)c(Nc3ccc(F)cc3)c21]

A mixture of Intermediate 1-2-28 (110 mg, 252 µmol), hydrogen peroxide (34% in water, 45.4 µl, 504 µmol) in MeOH (8.6 mL) was heated at 90° C. for 16 h. Purification by preparative HPLC (basic method) gave the desired product (40 mg, 39%).

1H-NMR (400 MHz, DMSO-d6), Shift [ppm]=2.84 (2H), 3.35-3.43 (2H), 4.40 (2H), 6.46 (1H), 6.44-6.60 (2H), 6.80 (2H), 7.00-7.19 (1H), 7.30 (1H), 7.38 (1H), 8.07 (1H), 8.37 (1H), 11.06 (1H).

Synthesis of Example 43—2-[3-(2,2-difluoroethoxy)pyridin-4-yl]-3-[(3,4-difluorophenyl)amino]-1,5,6,7-tetrahydro-4H-pyrrolo[3,2-c]pyridin-4-one Intermediate 1-2-29

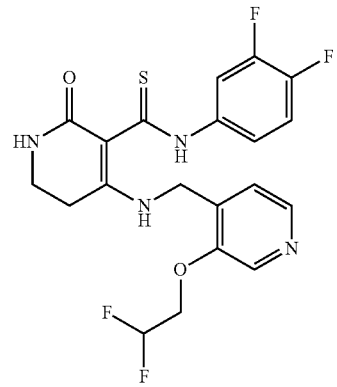 [SMILES: O=C1NCCC(NCc2ccncc2OCC(F)F)=C1C(=S)Nc1ccc(F)c(F)c1]

A solution of Intermediate 1-1-7 (250 mg, 0.879 mmol) and 1-[3-(2,2-difluoroethoxy)pyridin-4-yl]methanamine (199 mg, 1.06 mmol) in DMA (2.6 mL) was heated in a sealed tube at 130° C. for 60 min. Allowed to cool. Purified by preparative HPLC (basic method) to give the desired product (90 mg, 18%).

1H-NMR (400 MHz, DMSO-d6), Shift [ppm]=2.66-2.77 (2H), 3.11-3.31 (2H), 4.55 (2H), 4.69 (2H), 6.43 (1H), 7.11-7.18 (1H), 7.32 (1H), 7.42 (1H), 7.67 (1H), 7.76 (1H), 8.30 (1H), 8.46 (1H), 13.62 (1H), 14.88 (1H).

Example 43

2-[3-(2,2-difluoroethoxy)pyridin-4-yl]-3-[(3,4-difluorophenyl)amino]-1,5,6,7-tetrahydro-4H-pyrrolo[3,2-c]pyridin-4-one

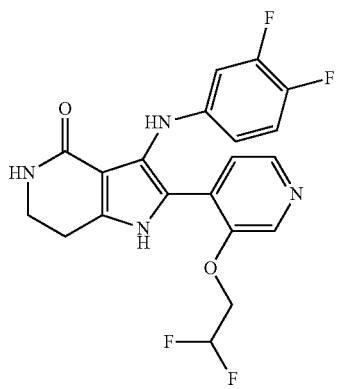 [SMILES: O=C1NCCc2[nH]c(-c3ccncc3OCC(F)F)c(Nc3ccc(F)c(F)c3)c21]

A mixture of Intermediate 1-2-29 (140 mg, 308 µmol), hydrogen peroxide (34% in water, 55.5 µl, 616 µmol) in MeOH (10.5 mL) was heated at 90° C. for 16 h. Purification by preparative HPLC (basic method) gave the desired product (30 mg, 23%).

1H-NMR (400 MHz, DMSO-d6), Shift [ppm]=2.82-2.88 (2H), 3.36-3.44 (2H), 4.41 (2H), 6.29-6.45 (3H), 6.97-7.10 (2H), 7.32 (1H), 7.52 (1H), 8.13 (1H), 8.40 (1H), 11.19 (1H).

Synthesis of Example 44—2-{3-[2-(dimethylamino)ethoxy]pyridin-4-yl}-3-[(4-fluorophenyl)amino]-1,5,6,7-tetrahydro-4H-pyrrolo[3,2-c]pyridin-4-one Intermediate 1-2-30

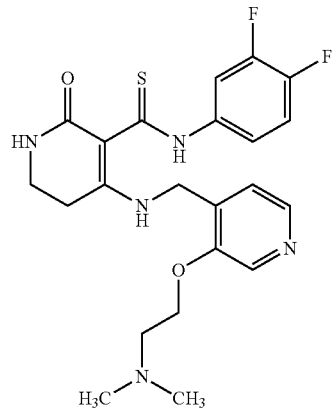 [SMILES: CN(C)CCOc1cnccc1CNC1=C(C(=S)Nc2ccc(F)c(F)c2)C(=O)NCC1]

A solution of Intermediate 1-1-4 (250 mg, 0.939 mmol) and 2-{[4-(aminomethyl)pyridin-3-yl]oxy}-N,N-dimethylethanamine (220 mg, 1.13 mmol) in DMA (2.8 mL) was heated in a sealed tube at 130° C. for 60 min. Allowed to cool. Purified by preparative HPLC (basic method) to give the desired product (60 mg, 14%).

1H-NMR (400 MHz, DMSO-d6), Shift [ppm]=2.22 (6H), 2.64-2.77 (4H), 3.10-3.29 (2H), 4.23 (2H), 4.64 (2H), 7.14-7.24 (2H), 7.29 (1H), 7.40 (2H), 7.69 (1H), 8.22 (1H), 8.40 (1H), 13.62 (1H), 14.70 (1H).

Example 44

2-{3-[2-(dimethylamino)ethoxy]pyridin-4-yl}-3-[(4-fluorophenyl)amino]-1,5,6,7-tetrahydro-4H-pyrrolo[3,2-c]pyridin-4-one

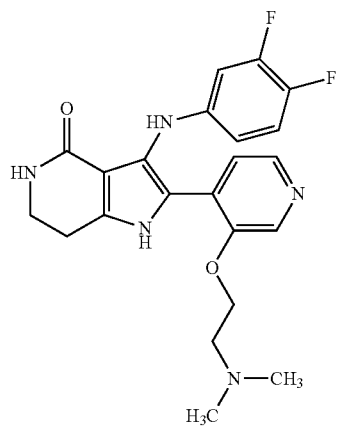 [SMILES: CN(C)CCOc1cnccc1-c1[nH]c2c(c1Nc1ccc(F)c(F)c1)C(=O)NCC2]

A mixture of Intermediate 1-2-30 (110 mg, 248 µmol), hydrogen peroxide (34% in water, 44.7 µl, 496 µmol) in MeOH (8.4 mL) was heated at 90° C. for 16 h. Purification by preparative HPLC (basic method) gave the desired product (4 mg, 4%).

1H-NMR (400 MHz, DMSO-d6), Shift [ppm]=2.32 (6H), 2.73 (2H), 2.85 (2H) 3.32-3.34 (2H), 4.39 (2H), 6.59 (2H), 6.78-6.94 (2H), 7.02-7.20 (2H), 7.33-7.37 (1H), 7.45 (1H), 7.94 (1H), 8.41 (1H), 12.18 (1H)

Synthesis of Example 45—3-[(3,4-difluorophenyl)amino]-2-[3-(2-methoxyethoxy)pyridin-4-yl]-1,5,6,7-tetrahydro-4H-pyrrolo[3,2-c]pyridin-4-one Intermediate 1-2-31

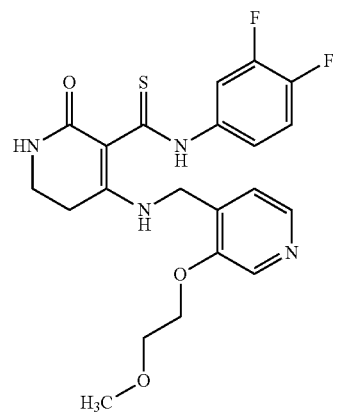 [SMILES: COCCOc1cnccc1CNC1=C(C(=S)Nc2ccc(F)c(F)c2)C(=O)NCC1]

A solution of Intermediate 1-1-7 (250 mg, 0.879 mmol) and 1-[3-(2-methoxyethoxy)pyridin-4-yl]methanamine (192 mg, 1.06 mmol) in DMA (2.6 mL) was heated in a sealed tube at 130° C. for 60 min. Allowed to cool. Purified by preparative HPLC (basic method) to give the desired product (90 mg, 23%).

1H-NMR (400 MHz, DMSO-d6), Shift [ppm]=2.76 (2H), 3.14 (2H), 3.31 (3H), 3.71 (2H), 4.30 (2H), 4.66 (2H), 7.12-7.17 (1H), 7.30 (1H), 7.41 (1H), 7.64-7.77 (2H), 8.24 (1H), 8.40 (1H), 13.61 (1H), 14.88 (1H).

Example 45

3-[(3,4-difluorophenyl)amino]-2-[3-(2-methoxyethoxy)pyridin-4-yl]-1,5,6,7-tetrahydro-4H-pyrrolo[3,2-c]pyridin-4-one

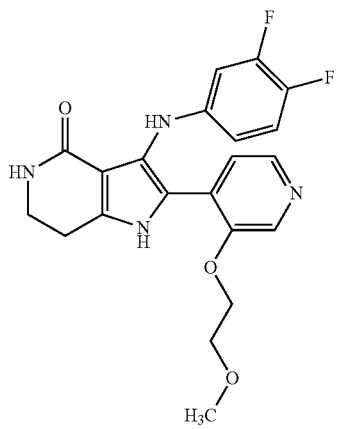 [SMILES: COCCOc1cnccc1-c1[nH]c2c(c1Nc1ccc(F)c(F)c1)C(=O)NCC2]

A mixture of Intermediate 1-2-31 (120 mg, 268 µmol), hydrogen peroxide (34% in water, 44.2 µl, 535 µmol) in MeOH (9.1 mL) was heated at 90° C. for 16 h. Purification by preparative HPLC (basic method) gave the desired product (30 mg, 27%).

1H-NMR (400 MHz, DMSO-d6), Shift [ppm]=2.84 (2H), 3.35-3.43 (5H), 3.72-3.78 (2H), 4.27-4.35 (2H), 6.31-6.38 (1H), 6.42-6.48 (1H), 6.99-7.13 (2H), 7.34 (1H), 7.51 (1H), 8.06 (1H), 8.40 (1H), 11.08 (1H).

Synthesis of Example 46—3-[(4-fluorophenyl)amino]-2-[3-(2-methoxyethoxy)pyridin-4-yl]-1,5,6,7-tetrahydro-4H-pyrrolo[3,2-c]pyridin-4-one Intermediate 1-2-32

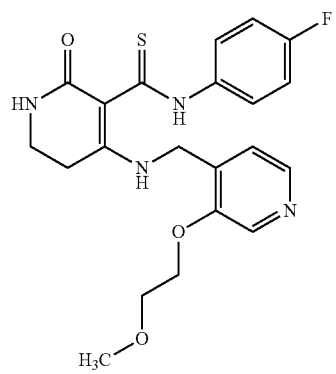 [SMILES: COCCOc1cnccc1CNC1=C(C(=S)Nc2ccc(F)cc2)C(=O)NCC1]

A solution of Intermediate 1-1-4 (250 mg, 0.939 mmol) and 1-[3-(2-methoxyethoxy)pyridin-4-yl]methanamine (205 mg, 1.13 mmol) in DMA (2.8 mL) was heated in a sealed tube at 130° C. for 60 min. Allowed to cool. Purified by preparative HPLC (basic method) to give the desired product (80 mg, 20%).

1H-NMR (400 MHz, DMSO-d6), Shift [ppm]=2.66-2.77 (2H), 3.14 (2H), 3.32 (3H), 3.68-3.73 (2H), 4.27-4.32 (2H), 4.65 (2H), 7.19 (2H), 7.30 (1H), 7.37-7.43 (2H), 7.69 (1H), 8.23 (1H), 8.39 (1H), 13.64 (1H), 14.70 (1H).

Example 46

3-[(4-fluorophenyl)amino]-2-[3-(2-methoxyethoxy)pyridin-4-yl]-1,5,6,7-tetrahydro-4H-pyrrolo[3,2-c]pyridin-4-one

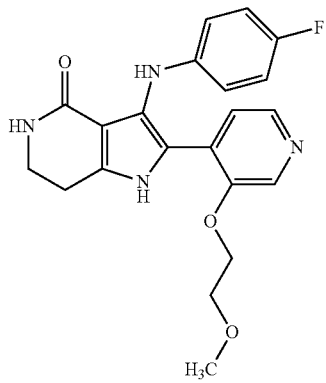 [SMILES: COCCOc1cnccc1-c1[nH]c2c(c1Nc1ccc(F)cc1)C(=O)NCC2]

A mixture of Intermediate 1-2-32 (120 mg, 279 μmol), hydrogen peroxide (34% in water, 50.2 μl, 557 μmol) in MeOH (9.4 mL) was heated at 90° C. for 16 h. Purification by preparative HPLC (basic method) gave the desired product (30 mg, 27%).

1H-NMR (400 MHz, DMSO-d6), Shift [ppm]=2.84 (2H), 3.36-3.45 (5H), 3.73-3.82 (2H), 4.26-4.36 (2H), 6.54-6.56 (1H), 6.58 (1H), 6.84 (2H), 7.11 (1H), 7.31 (1H), 7.36-7.45 (1H), 8.00 (1H), 8.38 (1H), 10.97 (1H).

Synthesis of Example 47—3-[(3-fluorophenyl)amino]-2-[3-(2-methoxyethoxy)pyridin-4-yl]-1,5,6,7-tetrahydro-4H-pyrrolo[3,2-c]pyridin-4-one Intermediate 1-2-33

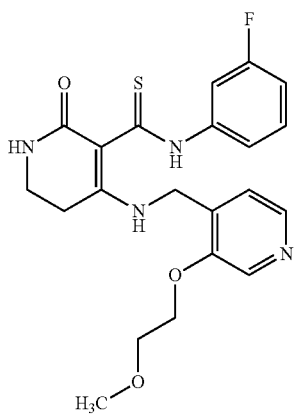 [SMILES: COCCOc1cnccc1CNC1=C(C(=S)Nc2cccc(F)c2)C(=O)NCC1]

A solution of Intermediate 1-1-9 (250 mg, 0.939 mmol) and 1-[3-(2-methoxyethoxy)pyridin-4-yl]methanamine (205 mg, 1.13 mmol) in DMA (2.8 mL) was heated in a sealed tube at 130° C. for 60 min. Allowed to cool. Purified by preparative HPLC (basic method) to give the desired product (80 mg, 20%).

1H-NMR (400 MHz, DMSO-d6), Shift [ppm]=2.76 (2H), 3.14 (2H), 3.32 (3H), 3.69-3.73 (2H), 4.28-4.32 (2H), 4.66 (2H), 7.02 (1H), 7.16 (1H), 7.29-7.42 (2H), 7.54 (1H), 7.74 (1H), 8.24 (1H), 8.40 (1H), 13.64 (1H), 14.97 (1H).

Example 47

3-[(3-fluorophenyl)amino]-2-[3-(2-methoxyethoxy)pyridin-4-yl]-1,5,6,7-tetrahydro-4H-pyrrolo[3,2-c]pyridin-4-one

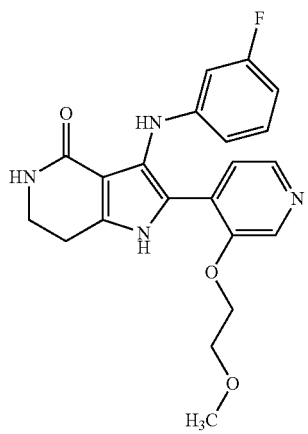 [SMILES: COCCOc1cnccc1-c1[nH]c2c(c1Nc1cccc(F)c1)C(=O)NCC2]

A mixture of Intermediate 1-2-33 (140 mg, 325 μmol), hydrogen peroxide (34% in water, 58.6 μl, 650 μmol) in MeOH (11 mL) was heated at 90° C. for 16 h. Purification by preparative HPLC (basic method) and silica chromatography gave the desired product (mg, 16%).

1H-NMR (400 MHz, DMSO-d6), Shift [ppm]=2.85 (2H), 3.36-3.43 (5H), 3.74-3.78 (2H), 4.31 (2H), 6.24 (1H), 6.30-6.42 (2H), 6.97-7.09 (2H), 7.36 (1H), 7.59 (1H), 8.04 (1H), 8.40 (1H), 11.08 (1H).

Biological Investigations

The following assays can be used to illustrate the commercial utility of the compounds according to the present invention.

Examples were tested in selected biological assays one or more times. When tested more than once, data are reported as either average values or as median values, wherein
- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG (C-terminus in amide form), purchased from e.g. Biosyntan (Berlin, Germany) by the (recombinant) catalytic domain of human Bub1 (amino acids 704-1085), expressed in Hi5 insect cells with an N-terminal His6-tag and purified by affinity- (Ni-NTA) and size exclusion chromatography.

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nl of compounds were transferred into a black low volume test microtiter plate from the same supplier. Subsequently, 2 µl of Bub1 (the final concentration of Bub1 was adjusted depending on the activity of the enzyme lot in order to be within the linear dynamic range of the assay: typically ~200 ng/ml were used) in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added to the compounds in the test plate and the mixture was incubated for 15 min at 22° C. to allow pre-equilibration of the putative enzyme-inhibitor complexes before the start of the kinase reaction, which was initiated by the addition of 3 µl 1.67-fold concentrated solution (in assay buffer) of adenosine-tri-phosphate (ATP, 10 µM final concentration) and peptide substrate (1 µM final concentration). The resulting mixture (5 µl final volume) was incubated at 22° C. during 60 min., and the reaction was stopped by the addition of 5 µl of an aqueous EDTA-solution (50 mM EDTA, in 100 mM HEPES pH 7.5 and 0.2% (w/v) bovine serum albumin) which also contained the TR-FRET detection reagents (0.2 µM streptavidin-XL665 [Cisbio Bioassays, Codolet, France] and 1 nM anti-phosho-Serine antibody [Merck Millipore, cat. #35-002] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antibody complex recognizing the Phosphoserine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of control wells for high- (=enzyme reaction without inhibitor=0%=Minimum inhibition) and low- (=all assay components without enzyme=100%=Maximum inhibition) Bub1 activity. $IC_{50}$ values were calculated by fitting the normalized inhibition data to a 4-parameter logistic equation (Minimum, Maximum, $IC_{50}$, Hill; Y=Max+(Min−Max)/(1+(X/$IC_{50}$)Hill)).

| Example Nr. | Bub1 kinase assay median $IC_{50}$ [mol/l] |
|---|---|
| 1 | 1.16E−8 |
| 2 | 7.89E−9 |
| 3 | 2.44E−7 |
| 4 | 1.46E−8 |
| 5 | 3.51E−8 |
| 6 | 1.09E−8 |
| 7 | 1.98E−8 |
| 8 | 1.38E−7 |
| 9 | 3.54E−7 |
| 10 | 3.19E−7 |
| 11 | 6.45E−8 |
| 12 | 1.54E−8 |
| 13 | 9.72E−7 |
| 14 | 1.83E−8 |
| 15 | 7.90E−8 |
| 16 | 1.91E−8 |
| 17 | 8.70E−9 |
| 18 | 1.15E−8 |
| 19 | 1.95E−8 |
| 20 | 1.34E−8 |
| 21 | 1.70E−7 |
| 22 | 2.69E−8 |
| 23 | 2.32E−8 |
| 24 | 1.53E−8 |
| 25 | 1.71E−8 |
| 26 | 4.76E−8 |
| 27 | 2.17E−8 |
| 28 | 5.16E−8 |
| 29 | 7.08E−8 |
| 30 | 8.43E−8 |
| 31 | 9.93E−9 |
| 32 | 4.16E−8 |
| 33 | 5.18E−8 |
| 34 | 2.25E−8 |
| 35 | 8.59E−8 |
| 36 | 3.48E−8 |
| 37 | 5.98E−8 |
| 38 | 5.61E−8 |
| 39 | 2.41E−8 |
| 40 | 2.81E−8 |
| 41 | 3.68E−8 |
| 42 | 1.11E−7 |
| 43 | 1.36E−7 |
| 44 | 6.99E−8 |
| 45 | 2.80E−8 |
| 46 | 3.28E−8 |
| 47 | 1.94E−8 |

The invention claimed is:

1. A compound of formula (I)

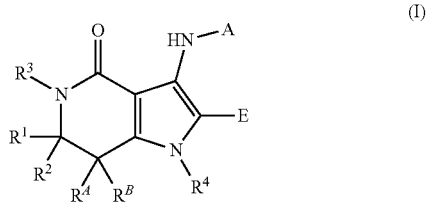

wherein:
R¹ is hydrogen, $C_1$-$C_6$-alkyl or $C_1$-$C_6$-haloalkyl;
R² is hydrogen, $C_1$-$C_6$-alkyl or $C_1$-$C_6$-haloalkyl;
or
R¹ and R² are taken together with the carbon atom to which they are attached to form a 3- to 6-membered cycloalkyl ring;
R³ is hydrogen, $C_1$-$C_4$-alkyl, $C_1$-$C_4$-haloalkyl, R¹¹—C(O)—, R¹¹O—C(O)— or phenyl-$C_1$-$C_3$-alkyl-,
wherein said phenyl group is optionally independently substituted, one or more times, with R⁵;
R⁴ is hydrogen, $C_1$-$C_4$-alkyl or $C_1$-$C_4$-alkoxy-$C_2$-$C_4$-alkyl-;
$R^A$ is hydrogen, hydroxy or $C_1$-$C_4$-alkyl;
$R^B$ is hydrogen;
or
$R^B$ and R² are taken together to form an additional bond;
A is a group selected from the group consisting of:

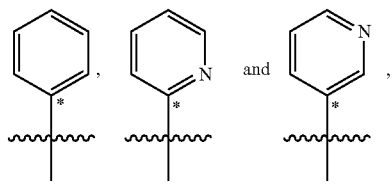

wherein * indicates the point of attachment of said group with the rest of the molecule, and said group is optionally independently substituted, one or more times, with R⁵;
R⁵ is hydroxy, halogen, cyano, $C_1$-$C_4$-alkyl, $C_1$-$C_4$-alkoxy, $C_1$-$C_4$-haloalkyl or C1-C4-haloalkoxy;
E is a group selected from the group consisting of:

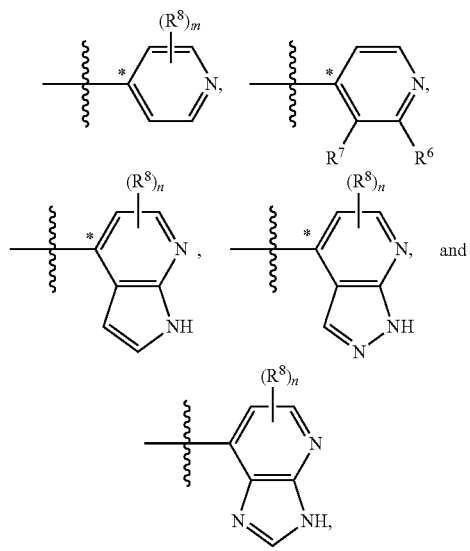

wherein * indicates the point of attachment of said group with the rest of the molecule;
R⁶ and R⁷ are independently hydrogen, halogen, hydroxy, cyano, $C_1$-$C_4$-alkyl, $C_1$-$C_6$-alkoxy, $C_3$-$C_6$-cycloalkyl, or $C_3$-$C_6$-halocycloalkyl,
wherein said $C_1$-$C_6$-alkoxy is optionally independently substituted one, two or three times, with halogen or is optionally substituted one time with hydroxy, $C_1$-$C_4$-alkoxy, R⁹R¹⁰N—, $C_3$-$C_6$-cycloalkyl, 5- to 6-membered heterocycloalkyl or phenyl, which is optionally independently substituted, one or more times, with R⁵;
each R⁸ is independently halogen, hydroxy, nitro, cyano, $C_1$-$C_4$-alkyl, $C_1$-$C_4$-haloalkyl, $C_1$-$C_6$-alkoxy, $C_3$-$C_6$-cycloalkyl, or $C_3$-$C_6$-halocycloalkyl,
wherein said $C_1$-$C_6$-alkoxy is optionally independently substituted one, two or three times, with halogen and is optionally substituted one time with hydroxy, $C_1$-$C_4$-alkoxy, R⁹R¹⁰N—, $C_3$-$C_6$-cycloalkyl, 4- to 7-membered heterocycloalkyl or phenyl, which is optionally independently substituted one or more times, with R⁵;
each R⁹ and R¹⁰ is independently hydrogen, $C_1$-$C_4$-alkyl, $C_3$-$C_6$-cycloalkyl, $C_1$-$C_4$-haloalkyl, $C_3$-$C_6$-halocycloalkyl or phenyl,
wherein said phenyl group is optionally independently substituted, one or more times, with R⁵;
or
R⁹ and R¹⁰ are taken together with the nitrogen atom to which they are attached to form a 3- to 6-membered nitrogen containing heterocyclic ring, optionally containing one additional heteroatom or heteroatom containing group selected from the group consisting of O, NH, and S, and which is optionally independently substituted, one or more times, with R⁵;
each R¹¹ is independently $C_1$-$C_4$-alkyl, $C_3$-$C_6$-cycloalkyl, $C_1$-$C_4$-haloalkyl or $C_3$-$C_6$-halocycloalkyl;
m is 0, 1, 2, or 3; and
n is 0, 1, or 2,
or an N-oxide, a salt, a tautomer or a stereoisomer of said compound, or a salt of said N-oxide, tautomer or stereoisomer.

2. The compound of formula (I) according to claim 1, wherein:
R¹ is hydrogen, $C_1$-$C_4$-alkyl or $C_1$-$C_4$-haloalkyl;
R² is hydrogen, $C_1$-$C_4$-alkyl or $C_1$-$C_4$-haloalkyl;
or
R¹ and R² are taken together with the carbon atom to which they are attached to form a 3- to 6-membered cycloalkyl ring;
R³ is hydrogen, $C_1$-$C_4$-alkyl, $C_1$-$C_4$-haloalkyl, R¹¹—C(O)— or R¹¹O—C(O)—;
R⁴ is hydrogen, $C_1$-$C_4$-alkyl or $C_1$-$C_4$-alkoxy-$C_2$-$C_4$-alkyl-;
$R^A$ is hydrogen, hydroxy or $C_1$-$C_4$-alkyl;
$R^B$ is hydrogen;
or
$R^B$ and R² are taken together to form an additional bond;
A is a group

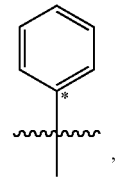 [SMILES: *c1ccccc1]

wherein * indicates the point of attachment of said group with the rest of the molecule, and said group is optionally independently substituted, one or more times, with R⁵;

$R^5$ is hydroxy, halogen, cyano, $C_1$-$C_4$-alkyl, $C_1$-$C_4$-alkoxy, $C_1$-$C_4$-haloalkyl or $C_1$-$C_4$-haloalkoxy;

E is a group selected from the group consisting of:

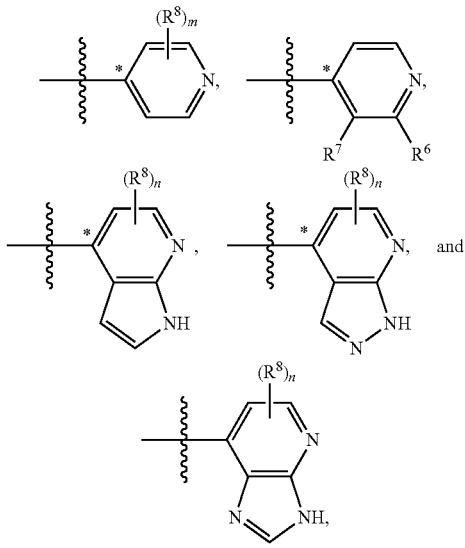

wherein * indicates the point of attachment of said group with the rest of the molecule;

$R^6$ and $R^7$ are independently hydrogen, halogen, hydroxy, cyano, $C_1$-$C_4$-alkyl, $C_1$-$C_6$-alkoxy, $C_3$-$C_6$-cycloalkyl, or $C_3$-$C_6$-halocycloalkyl, wherein said $C_1$-$C_6$-alkoxy is optionally independently substituted one, two or three times, with halogen or is optionally substituted one time with hydroxy, $C_1$-$C_4$-alkoxy, $R^9R^{10}N$—, $C_3$-$C_6$-cycloalkyl, 5- to 6-membered heterocycloalkyl or phenyl, which is optionally independently substituted, one or more times, with $R^5$;

each $R^8$ is independently halogen, hydroxy, nitro, cyano, $C_1$-$C_4$-alkyl, $C_1$-$C_4$-haloalkyl, $C_1$-$C_6$-alkoxy, $C_3$-$C_6$-cycloalkyl, or $C_3$-$C_6$-halocycloalkyl, wherein said $C_1$-$C_6$-alkoxy is optionally independently substituted one, two or three times, with halogen or is optionally substituted one time with hydroxy, $C_1$-$C_4$-alkoxy, $R^9R^{10}N$—, $C_3$-$C_6$-cycloalkyl, 4- to 7-membered heterocycloalkyl or phenyl, which is optionally independently substituted one or more times, with $R^5$;

each $R^9$ and $R^{10}$ is independently hydrogen, $C_1$-$C_4$-alkyl, $C_3$-$C_6$-cycloalkyl, $C_1$-$C_4$-haloalkyl, $C_3$-$C_6$-halocycloalkyl or phenyl, wherein said phenyl group is optionally independently substituted, one or more times, with $R^5$;

or $R^9$ and $R^{10}$ are taken together with the nitrogen atom to which they are attached to form a 3- to 6-membered nitrogen containing heterocyclic ring, optionally containing one additional heteroatom or heteroatom containing group selected from the group consisting of O, NH, and S, and which is optionally independently substituted, one or more times, with $R^5$;

each $R^{11}$ is independently $C_1$-$C_4$-alkyl, $C_3$-$C_6$-cycloalkyl, $C_1$-$C_4$-haloalkyl or $C_3$-$C_6$-halocycloalkyl;

m is 0, 1, 2, or 3; and n is 0 or 1, or an N-oxide, a salt, a tautomer or a stereoisomer of said compound, or a salt of said N-oxide, tautomer or stereoisomer.

3. The compound of formula (I) according to claim 1, wherein:

$R^1$ is hydrogen, $C_1$-$C_4$-alkyl or $C_1$-$C_4$-haloalkyl;

$R^2$ is hydrogen, $C_1$-$C_4$-alkyl or $C_1$-$C_4$-haloalkyl;

or $R^1$ and $R^2$ are taken together with the carbon atom to which they are attached to form a 3- to 6-membered cycloalkyl ring;

$R^3$ is hydrogen, $C_1$-$C_4$-alkyl, $C_1$-$C_4$-haloalkyl, $R^{11}$—C(O)— or $R^{11}$O—C(O)—;

$R^4$ is hydrogen, $C_1$-$C_4$-alkyl or $C_1$-$C_4$-alkoxy-$C_2$-$C_4$-alkyl;

$R^A$ is hydrogen, hydroxy or $C_1$-$C_4$-alkyl;

$R^B$ is hydrogen;

or $R^B$ and $R^2$ are taken together to form an additional bond;

A is a group

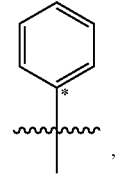 [SMILES: *c1ccccc1]

wherein * indicates the point of attachment of said group with the rest of the molecule, and said group is optionally independently substituted, one or more times, with $R^5$;

$R^5$ is hydroxy, halogen, cyano, $C_1$-$C_4$-alkyl, $C_1$-$C_4$-alkoxy, $C_1$-$C_4$-haloalkyl or $C_1$-$C_4$-haloalkoxy;

E is a group selected from the group consisting of:

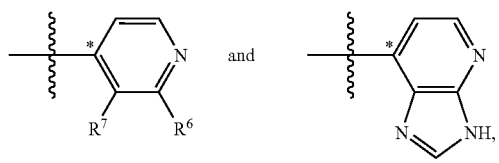

wherein * indicates the point of attachment of said group with the rest of the molecule;

$R^6$ and $R^7$ are independently hydrogen, halogen, hydroxy, cyano, $C_1$-$C_4$-alkyl, $C_1$-$C_6$-alkoxy, $C_3$-$C_6$-cycloalkyl, or $C_3$-$C_6$-halocycloalkyl, wherein said $C_1$-$C_6$-alkoxy is optionally independently substituted one, two or three times, with halogen or is optionally substituted one time with hydroxy, $C_1$-$C_4$-alkoxy, $R^9R^{10}N$—, $C_3$-$C_6$-cycloalkyl, 5- to 6-membered heterocycloalkyl or phenyl, which is optionally independently substituted, one or more times, with $R^5$;

each $R^9$ and $R^{10}$ is independently hydrogen or $C_1$-$C_4$-alkyl; and each $R^{11}$ is independently $C_1$-$C_4$-alkyl, $C_3$-$C_6$-cycloalkyl or $C_3$-$C_6$-halocycloalkyl, or an N-oxide, a salt, a tautomer or a stereoisomer of said compound, or a salt of said N-oxide, tautomer or stereoisomer.

4. The compound of formula (I) according to claim 1, wherein:
$R^1$ is hydrogen or $C_1$-$C_4$-alkyl;
$R^2$ is hydrogen or $C_1$-$C_4$-alkyl;
or
$R^1$ and $R^2$ are taken together with the carbon atom to which they are attached to form a 3- to 6-membered cycloalkyl ring;
$R^3$ is hydrogen, $C_1$-$C_4$-alkyl, $R^{11}$—C(O)— or $R^{11}$O—C(O)—;
$R^4$ is hydrogen, $C_1$-$C_4$-alkyl or $C_1$-$C_4$-alkoxy-$C_2$-$C_4$-alkyl;
$R^A$ is hydrogen;
$R^B$ is hydrogen;
or
$R^B$ and $R^2$ are taken together to form an additional bond;
A is a group

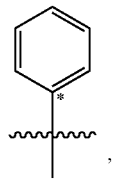 [SMILES: *c1ccccc1]

, wherein * indicates the point of attachment of said group with the rest of the molecule, and said group is optionally independently substituted, one or more times, with $R^5$;
$R^5$ is halogen;
E is a group selected from the group consisting of:

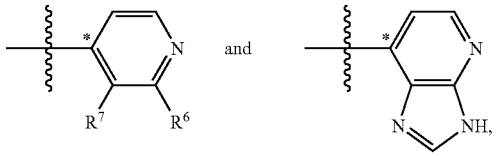

wherein * indicates the point of attachment of said group with the rest of the molecule;
$R^6$ and $R^7$ are independently hydrogen, halogen, $C_1$-$C_4$-alkyl, or $C_1$-$C_6$-alkoxy,
wherein said $C_1$-$C_6$-alkoxy is optionally independently substituted one, two or three times, with halogen or is optionally substituted one time with hydroxy, methoxy, $(CH_3)_2N$—, cyclopropyl, 5-membered heterocycloalkyl or phenyl, which is optionally substituted once with $R^5$;
each $R^9$ and $R^{10}$ is independently hydrogen or $C_1$-$C_4$-alkyl; and
each $R^{11}$ is independently $C_1$-$C_4$-alkyl, $C_3$-$C_6$-cycloalkyl or $C_3$-$C_6$-halocycloalkyl,
or an N-oxide, a salt, a tautomer or a stereoisomer of said compound, or a salt of said N-oxide, tautomer or stereoisomer.

5. The compound of formula (I) according to claim 1, wherein:
$R^1$ is hydrogen or methyl;
$R^2$ is hydrogen or methyl;
$R^3$ is hydrogen, methyl, iso-propyl-C(O)— or tert-butyl-O—C(O)—;
$R^4$ is hydrogen, ethyl or 2-methoxy-ethyl;
$R^A$ is hydrogen;
$R^B$ is hydrogen;
or
$R^B$ and $R^2$ are taken together to form an additional bond;
A is phenyl optionally substituted with one or two fluorine atoms;
E is a group selected from the group consisting of:

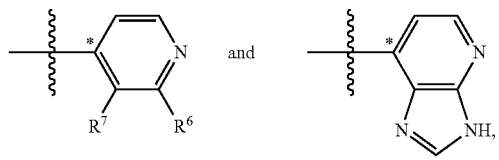

wherein * indicates the point of attachment of said group with the rest of the molecule;
$R^6$ is hydrogen or methyl;
$R^7$ is hydrogen, fluoro, methyl, methoxy, cyclopropylmethoxy, tetrahydrofuran-3-ylmethoxy, 2-hydroxyethoxy, 2-methoxyethoxy, 2,2-difluoroethoxy, 2,2,2-trifluoroethoxy, 2-(dimethylamino)ethoxy, propoxy, 3,3,3-trifluoropropoxy, butoxy, 3,3-dimethylbutoxy or benzyloxy;
each $R^9$ and $R^{10}$ is independently hydrogen or ethyl; and
each $R^{11}$ is independently methyl, iso-propyl, tert-butyl, cyclopropyl or fluorocyclopropyl,
or an N-oxide, a salt, a tautomer or a stereoisomer of said compound, or a salt of said N-oxide, tautomer or stereoisomer.

6. The compound of formula (I) according to claim 1, which is selected from the group consisting of:
6,6-dimethyl-3-(phenylamino)-2-(pyridin-4-yl)-1,5,6,7-tetrahydro-4H-pyrrolo[3,2-c]pyridin-4-one;
3-(phenylamino)-2-(pyridin-4-yl)-1,5,6,7-tetrahydro-4H-pyrrolo[3,2-c]pyridin-4-one;
2-(3-methylpyridin-4-yl)-3-(phenylamino)-1,5,6,7-tetrahydro-4H-pyrrolo[3,2-c]pyridin-4-one;
1-ethyl-6,6-dimethyl-3-(phenylamino)-2-(pyridin-4-yl)-1,5,6,7-tetrahydro-4H-pyrrolo[3,2-c]pyridin-4-one;
1-ethyl-3-(phenylamino)-2-(pyridin-4-yl)-1,5,6,7-tetrahydro-4H-pyrrolo[3,2-c]pyridin-4-one;
tert-butyl 4-oxo-3-(phenylamino)-2-(pyridin-4-yl)-1,4,6,7-tetrahydro-5H-pyrrolo[3,2-c]pyridine-5-carboxylate;
3-[(4-fluorophenyl)amino]-2-(pyridin-4-yl)-1,5,6,7-tetrahydro-4H-pyrrolo[3,2-c]pyridin-4-one;
1-(2-methoxyethyl)-3-(phenylamino)-2-(pyridin-4-yl)-1,5,6,7-tetrahydro-4H-pyrrolo[3,2-c]pyridin-4-one;
1-ethyl-3-[(4-fluorophenyl)amino]-2-(pyridin-4-yl)-1,5,6,7-tetrahydro-4H-pyrrolo[3,2-c]pyridin-4-one;
2-(2-methylpyridin-4-yl)-3-(phenylamino)-1,5,6,7-tetrahydro-4H-pyrrolo[3,2-c]pyridin-4-one;
1-ethyl-2-(2-methylpyridin-4-yl)-3-(phenylamino)-1,5,6,7-tetrahydro-4H-pyrrolo[3,2-c]pyridin-4-one;
2-(3-fluoropyridin-4-yl)-3-(phenylamino)-1,5-dihydro-4H-pyrrolo[3,2-c]pyridin-4-one;
2-(3-fluoropyridin-4-yl)-3-(phenylamino)-1,5,6,7-tetrahydro-4H-pyrrolo[3,2-c]pyridin-4-one;
5-methyl-3-(phenylamino)-2-(pyridin-4-yl)-1,5,6,7-tetrahydro-4H-pyrrolo[3,2-c]pyridin-4-one;
2-(3-fluoropyridin-4-yl)-5-methyl-3-(phenylamino)-1,5,6,7-tetrahydro-4H-pyrrolo[3,2-c]pyridin-4-one;
2-(3-methoxypyridin-4-yl)-5-methyl-3-(phenylamino)-1,5,6,7-tetrahydro-4H-pyrrolo[3,2-c]pyridin-4-one;

2-[3-(2-hydroxyethoxy)pyridin-4-yl]-5-methyl-3-(phenylamino)-1,5,6,7-tetrahydro-4H-pyrrolo[3,2-c]pyridin-4-one;
2-[3-(cyclopropylmethoxy)pyridin-4-yl]-5-methyl-3-(phenylamino)-1,5,6,7-tetrahydro-4H-pyrrolo[3,2-c]pyridin-4-one;
5-methyl-3-(phenylamino)-2-(3-propoxypyridin-4-yl)-1,5,6,7-tetrahydro-4H-pyrrolo[3,2-c]pyridin-4-one;
2-[3-(2,2-difluoroethoxy)pyridin-4-yl]-5-methyl-3-(phenylamino)-1,5,6,7-tetrahydro-4H-pyrrolo[3,2-c]pyridin-4-one;
5-methyl-3-(phenylamino)-2-[3-(2,2,2-trifluoroethoxy)pyridin-4-yl]-1,5,6,7-tetrahydro-4H-pyrrolo[3,2-c]pyridin-4-one;
2-[3-(2-methoxyethoxy)pyridin-4-yl]-5-methyl-3-(phenylamino)-1,5,6,7-tetrahydro-4H-pyrrolo[3,2-c]pyridin-4-one;
2-[3-(benzyloxy)pyridin-4-yl]-5-methyl-3-(phenylamino)-1,5,6,7-tetrahydro-4H-pyrrolo[3,2-c]pyridin-4-one;
5-methyl-3-(phenylamino)-2-[3-(3,3,3-trifluoropropoxy)pyridin-4-yl]-1,5,6,7-tetrahydro-4H-pyrrolo[3,2-c]pyridin-4-one;
5-methyl-3-(phenylamino)-2-{3-[(3S)-tetrahydrofuran-3-ylmethoxy]pyridin-4-yl}-1,5,6,7-tetrahydro-4H-pyrrolo[3,2-c]pyridin-4-one;
2-[3-(3,3-dimethylbutoxy)pyridin-4-yl]-5-methyl-3-(phenylamino)-1,5,6,7-tetrahydro-4H-pyrrolo[3,2-c]pyridin-4-one;
2-(3H-imidazo[4,5-b]pyridin-7-yl)-5-methyl-3-(phenylamino)-1,5,6,7-tetrahydro-4H-pyrrolo[3,2-c]pyridin-4-one;
2-[3-(cyclopropylmethoxy)pyridin-4-yl]-3-[(3,4-difluorophenyl)amino]-1,5,6,7-tetrahydro-4H-pyrrolo[3,2-c]pyridin-4-one;
2-[3-(cyclopropylmethoxy)pyridin-4-yl]-3-[(4-fluorophenyl)amino]-1,5,6,7-tetrahydro-4H-pyrrolo[3,2-c]pyridin-4-one;
2-[3-(cyclopropylmethoxy)pyridin-4-yl]-3-[(3-fluorophenyl)amino]-1,5,6,7-tetrahydro-4H-pyrrolo[3,2-c]pyridin-4-one;
2-[3-(2,2-difluoroethoxy)pyridin-4-yl]-3-[(3-fluorophenyl)amino]-1,5,6,7-tetrahydro-4H-pyrrolo[3,2-c]pyridin-4-one;
2-[3-(2,2-difluoroethoxy)pyridin-4-yl]-3-[(4-fluorophenyl)amino]-1,5,6,7-tetrahydro-4H-pyrrolo[3,2-c]pyridin-4-one;
2-[3-(2,2-difluoroethoxy)pyridin-4-yl]-3-[(3,4-difluorophenyl)amino]-1,5,6,7-tetrahydro-4H-pyrrolo[3,2-c]pyridin-4-one;
2-{3-[2-(dimethylamino)ethoxy]pyridin-4-yl}-3-[(4-fluorophenyl)amino]-1,5,6,7-tetrahydro-4H-pyrrolo[3,2-c]pyridin-4-one;
3-[(3,4-difluorophenyl)amino]-2-[3-(2-methoxyethoxy)pyridin-4-yl]-1,5,6,7-tetrahydro-4H-pyrrolo[3,2-c]pyridin-4-one;
3-[(4-fluorophenyl)amino]-2-[3-(2-methoxyethoxy)pyridin-4-yl]-1,5,6,7-tetrahydro-4H-pyrrolo[3,2-c]pyridin-4-one; and
3-[(3-fluorophenyl)amino]-2-[3-(2-methoxyethoxy)pyridin-4-yl]-1,5,6,7-tetrahydro-4H-pyrrolo[3,2-c]pyridin-4-one,
or an N-oxide, a salt, a tautomer or a stereoisomer of said compound, or a salt of said N-oxide, tautomer or stereoisomer.

7. A pharmaceutical composition comprising at least one compound of formula (I) according to claim 1, or an N-oxide, a salt, a tautomer or a stereoisomer of said compound, or a salt of said N-oxide, tautomer or stereoisomer, together with at least one pharmaceutically acceptable auxiliary.

8. A combination comprising one or more first active ingredients selected from the compound of formula (I) according to claim 1, or an N-oxide, a salt, a tautomer or a stereoisomer of said compound, or a salt of said N-oxide, tautomer or stereoisomer, and one or more second active ingredients selected from the group consisting of a chemotherapeutic anti-cancer agent and a target-specific anti-cancer agent.

9. A compound of formula 1-2:

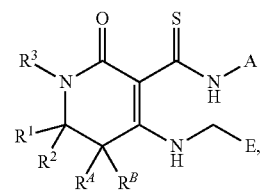

wherein $R^1$, $R^2$, $R^3$, $R^A$, $R^B$, A and E are as defined in claim 1.

10. A process for preparing the compound of formula (I) according to claim 1, comprising reacting a compound of formula 1-2:

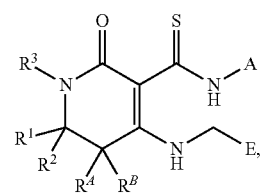

wherein $R^1$, $R^2$, $R^3$, $R^A$, $R^B$, A and E are as defined in claim 1,
with a base and/or oxidizing reagent, followed by an alkylation agent,
to provide the compound of formula (I) according to claim 1,
and optionally converting the compound of formula (I) to an N-oxide, a salt, a tautomer or a stereoisomer thereof, or a salt of said N-oxide, tautomer or stereoisomer.

11. The compound of claim 1 or a salt thereof.
12. The compound of claim 6 or a salt thereof.
13. The pharmaceutical composition of claim 7, comprising the compound of formula (I) or a salt thereof.
14. The combination of claim 8, comprising the compound of formula (I) or a salt thereof.
15. A compound which is selected from the group consisting of:
  6,6-dimethyl-3-(phenylamino)-2-(pyridin-4-yl)-1,5,6,7-tetrahydro-4H-pyrrolo[3,2-c]pyridin-4-one;
  3-(phenylamino)-2-(pyridin-4-yl)-1,5,6,7-tetrahydro-4H-pyrrolo[3,2-c]pyridin-4-one;
  2-(3-methylpyridin-4-yl)-3-(phenylamino)-1,5,6,7-tetrahydro-4H-pyrrolo[3,2-c]pyridin-4-one;
  1-ethyl-6,6-dimethyl-3-(phenylamino)-2-(pyridin-4-yl)-1,5,6,7-tetrahydro-4H-pyrrolo[3,2-c]pyridin-4-one;
  and 1-ethyl-3-(phenylamino)-2-(pyridin-4-yl)-1,5,6,7-tetra-hydro-4H-pyrrolo[3,2-c]pyridin-4-one,
or an N-oxide, a salt, a tautomer or a stereoisomer of said compound, or a salt of said N-oxide, tautomer or stereoisomer.

* * * * *